US012758160B2

(12) United States Patent
Capodilupo et al.

(10) Patent No.: US 12,758,160 B2
(45) Date of Patent: Oct. 13, 2026

(54) COACHING BASED ON REPRODUCTIVE PHASES

(71) Applicant: Whoop, Inc., Boston, MA (US)

(72) Inventors: Emily Rachel Capodilupo, Boston, MA (US); Summer Rose Jasinski, Cambridge, MA (US)

(73) Assignee: Whoop, Inc., Boston, MA (US)

( * ) Notice: Subject to any disclaimer, the term of this patent is extended or adjusted under 35 U.S.C. 154(b) by 300 days.

(21) Appl. No.: 18/463,096

(22) Filed: Sep. 7, 2023

(65) Prior Publication Data

US 2024/0074709 A1 Mar. 7, 2024

Related U.S. Application Data

(60) Provisional application No. 63/404,247, filed on Sep. 7, 2022.

(51) Int. Cl.

| | |
|---|---|
| ***A61B 5/00*** | (2006.01) |
| ***A61B 5/024*** | (2006.01) |
| ***A61B 10/00*** | (2006.01) |
| ***G16H 50/30*** | (2018.01) |

(52) U.S. Cl.

CPC ........ *A61B 5/7275* (2013.01); *A61B 5/02405* (2013.01); *A61B 5/02416* (2013.01); *A61B 5/02438* (2013.01); *A61B 5/6824* (2013.01); *A61B 5/6831* (2013.01); *A61B 5/7264* (2013.01); *A61B 5/7282* (2013.01); *A61B 5/742* (2013.01); *A61B 10/0012* (2013.01); *G16H 50/30* (2018.01); *A61B 2010/0019* (2013.01); *A61B 2010/0029* (2013.01)

(58) Field of Classification Search

None

See application file for complete search history.

(56) References Cited

U.S. PATENT DOCUMENTS

| | | | |
|---|---|---|---|
| 2002/0124295 A1 | 9/2002 | Fenwick et al. |
| 2010/0292599 A1 | 11/2010 | Oleson et al. |
| 2014/0180019 A1 | 6/2014 | Martinez et al. |
| 2016/0135743 A1 | 5/2016 | Cobbett et al. |

(Continued)

FOREIGN PATENT DOCUMENTS

| | | |
|---|---|---|
| CN | 114678119 | 6/2022 |
| EP | 3332698 | 6/2018 |

(Continued)

OTHER PUBLICATIONS

ISA/EP, "PCT Application No. PCT/US23/73669 International Search Report and Written Opinion mailed Feb. 6, 2024", NPL-330, 20 pages.

(Continued)

*Primary Examiner* — Ankit D Tejani

(74) *Attorney, Agent, or Firm* — Strategic Patents, P.C.

(57) ABSTRACT

Physiological metrics such as respiratory rate, resting heart rate, heart rate variability, temperature, and the like can be measured over time for a user and correlated to reproductive phases. By determining the chronological phase in a hormonal cycle or the like, automated recommendations for sleep, diet, exercise and the like can be provided in a phase-coordinated manner.

20 Claims, 33 Drawing Sheets

(56) References Cited

U.S. PATENT DOCUMENTS

| | | | | |
|---|---|---|---|---|
| 2016/0143630 | A1* | 5/2016 | Pardey | A61B 5/01 600/549 |
| 2016/0266606 | A1 | 9/2016 | Ricci | |
| 2018/0220962 | A1 | 8/2018 | Palley et al. | |
| 2018/0242654 | A1 | 8/2018 | Marikkar et al. | |
| 2019/0110748 | A1 | 4/2019 | Cho et al. | |
| 2019/0159680 | A1 | 5/2019 | Tanaka et al. | |
| 2020/0000441 | A1* | 1/2020 | Lafon | A61B 5/02438 |
| 2020/0229800 | A1* | 7/2020 | Mena Benito | A61B 5/6804 |
| 2021/0401314 | A1 | 12/2021 | Pho et al. | |
| 2021/0401378 | A1 | 12/2021 | Pho et al. | |
| 2021/0407684 | A1 | 12/2021 | Pho et al. | |
| 2022/0273232 | A1 | 9/2022 | Capodilupo et al. | |
| 2022/0409187 | A1 | 12/2022 | Pho et al. | |

FOREIGN PATENT DOCUMENTS

| | | |
|---|---|---|
| EP | 3785641 | 3/2021 |
| GB | 2533774 | 7/2016 |
| WO | WO-2014188171 | 11/2014 |
| WO | WO-2015134654 | 9/2015 |
| WO | WO-2019168475 | 9/2019 |
| WO | WO-2019213114 | 11/2019 |
| WO | WO-2021038025 | 3/2021 |
| WO | WO-2024054930 | 3/2024 |

OTHER PUBLICATIONS

ISA/EP, “PCT Application No. PCT/US23/73669 Invitation to pay addition fee/ partial search mailed Dec. 15, 2023”, 14 pages.

Grant, Azure et al., “Feasibility of Continuous Distal Body Temperature for Passive, Early Pregnancy Detection”, https://doi.org/10.1101/2021.08.19.21262306 Aug. 21, 2021 , 24 Pages.

Erickson, N. E. et al., “Predicting labor onset relative to the estimated date of delivery using smart ring physiological data”, npj Digital Medicine vol. 6, Article No. 153 (2023) Aug. 19, 2023 , 13 Pages.

Mason, Ashley E. et al., “Detection of Covid-19 using multimodal data from a wearable device: results from the first TemPredict Study”, Scientific Reports, (2022) 12:3463, https://doi.org/10.1038/s41598-022-07314-0 NPL-332 Mar. 2, 2022 , 15 Pages.

Smarr, Benjamin L. et al., “Feasibility of continuous fever monitoring using wearable devices”, Scientific Reports | (2020) 10:21640, https://doi.org/10.1038/s41598-020-78355-6 NPL-333 Dec. 14, 2020 , 11 Pages.

EPO, , “EP Application No. 23782402.4 Communication Pursuant to Article 94(3) mailed Feb. 26, 2025”, NPL-338 , 5 pages.

ISA/EP, , “PCT Application No. PCT/US23/73669 International Preliminary Report on Patentability mailed Mar. 20, 2025”, NPL-339—13 pages.

* cited by examiner

COACHING BASED ON REPRODUCTIVE PHASES

RELATED APPLICATIONS

This application claims priority to U.S. App. No. 63/404,247 filed on Sep. 7, 2022, the entire contents of which are hereby incorporated by reference.

TECHNICAL FIELD

The present disclosure generally relates to providing recommendations and coaching based on reproductive phases such as the menstrual cycle, pregnancy, and menopause.

BACKGROUND

Reproductive phases may affect health, fitness, recovery, sleep, and the like. There remains a need for techniques to identify a reproductive phase in a manner that facilitates coordinated delivery of coaching and recommendations related to exercise, recovery, sleep, diet, and other areas of health and fitness.

SUMMARY

Physiological metrics such as respiratory rate, resting heart rate, heart rate variability, temperature, and the like can be measured over time for a user and correlated to reproductive phases. By determining the chronological phase in a hormonal cycle or the like, automated recommendations for sleep, diet, exercise and the like can be provided in a phase-coordinated manner In an aspect, a computer program product disclosed herein may include computer executable code embodied in a non-transitory computer readable medium that, when executing on one or more computing devices, performs the steps of: providing a model that characterizes timewise changes during a model hormonal cycle for each of a heart rate variability, a resting heart rate, a body temperature, and a respiration rate; acquiring physiological data for a user from a wearable monitor, where the physiological data includes at least heart rate data and body temperature data, and where the physiological data is acquired during a hormonal cycle for the user; calculating a number of metrics for the user at least daily during the hormonal cycle, the number of metrics including at least the heart rate variability, the resting heart rate, the body temperature, and the respiration rate; calculating an estimated cycle time for the user relative to the model hormonal cycle based on each of the number of metrics independently; calculating a cycle time within the hormonal cycle for the user based on an ensemble of the estimated cycle times; and providing coaching information to the user based on the cycle time.

Implementations may include one or more of the following features. The hormonal cycle may include a menstrual cycle for the user. The hormonal cycle may include a pregnancy of the user. The ensemble may include a weighted average of the estimated cycle time for each of the number of metrics. The ensemble may include a combination of the estimated cycle time for each of the number of metrics based on a probability of accurately estimating the cycle time.

In an aspect, a method disclosed herein may include: providing a model that characterizes timewise changes during a model hormonal cycle for each of two or more physiological metrics; acquiring heart rate data from a wearable monitor worn by a user; calculating the two or more physiological metrics for the user at least daily based on the heart rate data; calculating a cycle time within a hormonal cycle for the user based on an ensemble of estimated cycle times, each estimated cycle time in the ensemble derived by applying one of the physiological metrics to the model; and providing coaching information to the user based on the cycle time.

Implementations may include one or more of the following features. The hormonal cycle may include a menstrual cycle for the user. The hormonal cycle may include a pregnancy of the user. The ensemble may include a weighted average of an estimated cycle time for each of the physiological metrics. The ensemble may include a combination of the estimated cycle times based on a probability of accurately estimating the cycle time. The ensemble may include a Bayesian model average of the estimated cycle times. The ensemble may include an average of at least two of the estimated cycle times. The wearable monitor may include a photoplethysmography monitor. The two or more physiological metrics may include at least one of a heart rate variability, a resting heart rate, and a respiration rate. The two or more physiological metrics may include a body temperature, where the wearable monitor includes a temperature sensor, and where the method includes acquiring temperature data from the temperature sensor and calculating the body temperature at least daily for the user. The model hormonal cycle may be derived from a population of users. The model hormonal cycle may be derived from a history of the user.

In an aspect, a system disclosed herein may include: a wearable monitor configured to acquire heart rate data from a user; a model stored in a memory, the model characterizing timewise changes during a model hormonal cycle for each of two or more physiological metrics; and a processor. The processor may be configured to generate a recommendation for the user by performing the steps of: receiving the heart rate data from the wearable monitor; calculating the two or more physiological metrics for the user on a periodic basis based on the heart rate data; calculating a cycle time within a hormonal cycle for the user based on an ensemble of estimated cycle times, each of the estimated cycle times derived by applying one of the physiological metrics to the model; and providing coaching information to the user based on the cycle time. The processor may execute on a personal computing device of the user. The processor may execute on a remote server coupled to the wearable monitor through a data network.

In an aspect, a computer program product may include computer executable code embodied in a non-transitory computer readable medium that, when executing on one or more computing devices, performs the steps of: providing a model that characterizes timewise changes during a model hormonal cycle for each of two or more physiological metrics; acquiring heart rate data from a wearable monitor worn by a user; calculating the two or more physiological metrics for the user at least daily based on the heart rate data; monitoring a hormonal cycle for the user by applying the two or more physiological metrics to the model hormonal cycle; identifying one or more timewise irregularities in the hormonal cycle relative to the model hormonal cycle; and, in response to calculating a likelihood above a predetermined threshold of an onset of menopause based on the one or more timewise irregularities, providing a recommendation to the user.

Implementations may include one or more of the following features. The model may be derived from a population of users. The model may be based on a history of the user. The two or more physiological metrics may include at least one of a heart rate variability, a resting heart rate, and a respiration rate. The wearable monitor may include a temperature sensor, the two or more physiological metrics may include a body temperature, and the computer program product may include code that performs the step of acquiring temperature data from the temperature sensor and calculating the body temperature at least daily for the user. Identifying the one or more timewise irregularities may include detecting a deviation in at least one of the physiological metrics from the model. Identifying the one or more timewise irregularities may include detecting a deviation in an ensemble of the two or more physiological metrics from the model. Identifying the one or more timewise irregularities may include detecting a change in an expected duration of the hormonal cycle. The recommendation may include at least one of a diet recommendation, a sleep recommendation, and an activity recommendation. The wearable monitor may include a photoplethysmography monitor.

In an aspect, a computer program product disclosed herein may include computer executable code embodied in a non-transitory computer readable medium that, when executing on one or more computing devices, performs the steps of: providing a model that characterizes timewise changes during a model hormonal cycle for each of two or more physiological metrics having a value influenced by one or more hormones associated with the model hormonal cycle; acquiring heart rate data from a wearable monitor worn by a user; calculating the two or more physiological metrics for the user at least daily based on the heart rate data; monitoring a hormonal cycle for the user by applying the two or more physiological metrics to the model hormonal cycle; identifying a series of peaks in the hormonal cycle for each of the two or more physiological metrics; identifying a timewise decrease in magnitude of each of the two or more physiological metrics for the series of peaks; in response to the timewise decrease in magnitude, providing a predicted onset of menopause for the user; and notifying the user of the predicted onset of menopause.

Implementations may include one or more of the following features. The model may be derived from a population of users. The model may be based on a history of the user. The two or more physiological metrics may include at least one of a heart rate variability, a resting heart rate, and a respiration rate. The wearable monitor may include a temperature sensor, the two or more physiological metrics may include a body temperature, and the computer program product may include code that performs the step of acquiring temperature data from the temperature sensor and calculating the body temperature at least daily for the user. The computer program product may include code that, when executing on one or more computing devices, performs the step of providing a recommendation to the user based on the predicted onset of menopause, the recommendation including at least one of a diet recommendation, a sleep recommendation, and an activity recommendation. The wearable monitor may include a photoplethysmography monitor.

In an aspect, a system disclosed herein may include: a wearable monitor configured to acquire heart rate data from a user; and a processor. The processor may be configured to perform the steps of: receiving the heart rate data from the wearable monitor; calculating two or more physiological metrics for the user on a periodic basis based on the heart rate data, the two or more physiological metrics having a value influenced by one or more hormones associated with a hormonal cycle of the user; generating a predicted onset of menopause for the user based on a predetermined pattern in the two or more physiological metrics over time; and providing coaching information to the user based on the predicted onset of menopause. The hormonal cycle may be identified by applying the two or more physiological metrics to a hormonal cycle model, where the predetermined pattern includes one or more timewise irregularities in the hormonal cycle. The hormonal cycle may be identified by applying the two or more physiological metrics to a hormonal cycle model, where the predetermined pattern includes a timewise decrease in magnitude of each of the two or more physiological metrics for a series of peaks in the hormonal cycle.

In an aspect, a computer program product disclosed herein for recommending adjustments to an activity regimen based on reproductive phases may include non-transitory computer executable code embodied in a computer readable medium that, when executing on one or more computing devices, performs the steps of: acquiring physiological data for a user from a wearable physiological monitoring device; identifying a phase in a hormonal cycle of the user based on the physiological data; determining a current recovery level for the user based on a prior sleep activity for the user; generating a recommended target for an activity regimen by the user based on the current recovery level; and automatically adjusting the activity regimen for the user by adjusting the recommended target based on the phase in the hormonal cycle.

In an aspect, a system disclosed herein may include: a wearable physiological monitoring device including one or more sensors, a first processor configured to substantially continuously acquire heart rate data for a user based on a signal from the one or more sensors, and a communications interface for coupling with a remote resource; a server coupled in a communicating relationship with the wearable physiological monitoring device, the server including a second processor configured by computer executable code to acquire physiological data for the user from the wearable physiological monitoring device, to identify a reproductive phase for the user based on the physiological data, to determine a current recovery level for the user based on a prior sleep activity for the user, to generate a recommended target for an activity regimen by the user based on the current recovery level, and to automatically adjust the activity regimen for the user by adjusting the recommended target based on the reproductive phase; and a user interface configured to present the recommended target to the user. The reproductive phase may include one of a pregnancy trimester, a postpartum period, a menopause phase, and a perimenopause phase.

In an aspect, a method disclosed herein may include: acquiring physiological data for a user from a wearable physiological monitoring device; identifying a reproductive phase for the user based on the physiological data; determining a current recovery level for the user based on a prior sleep activity for the user; generating a recommended target for an activity regimen by the user based on the current recovery level; and automatically adjusting the activity regimen for the user by adjusting the recommended target based on the reproductive phase.

Implementations may include one or more of the following features. The reproductive phase may include a pregnancy trimester. Identifying the reproductive phase may include identifying a gestational age of a fetus. The reproductive phase may include one of a menopause phase and a perimenopause phase. The physiological data may include heart rate data. Identifying the reproductive phase may include identifying the reproductive phase based on a pattern of change in a heart rate variability for the user. Identifying the reproductive phase may include determining a respiratory rate for the user and identifying the reproductive phase based on a pattern of change in the respiratory rate for the user. Determining the respiratory rate for the user may include determining the respiratory rate based on a heart rate variability for the user. Identifying the reproductive phase may include training a machine learning model to detect the reproductive phase based on one or more of a respiratory rate and a resting heart rate for the user. The prior sleep activity may be based on one or more of a prior strain, a heart rate variability, a resting heart rate, and a respiratory rate for the user. The prior sleep activity for the user may include a duration of sleep for a prior sleep event. The recommended target may include a target related to one or more of an activity volume and an activity intensity. The recommended target may include a sleep target. Adjusting the recommended target may include adjusting a duration of the sleep target. The method may include presenting the recommended target to the user on a user interface. The method may include presenting the reproductive phase to the user on a user interface. The physiological data may be captured substantially continuously by the wearable physiological monitoring device.

BRIEF DESCRIPTION OF THE DRAWINGS

The foregoing and other objects, features, and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

DESCRIPTION

Figure 1:
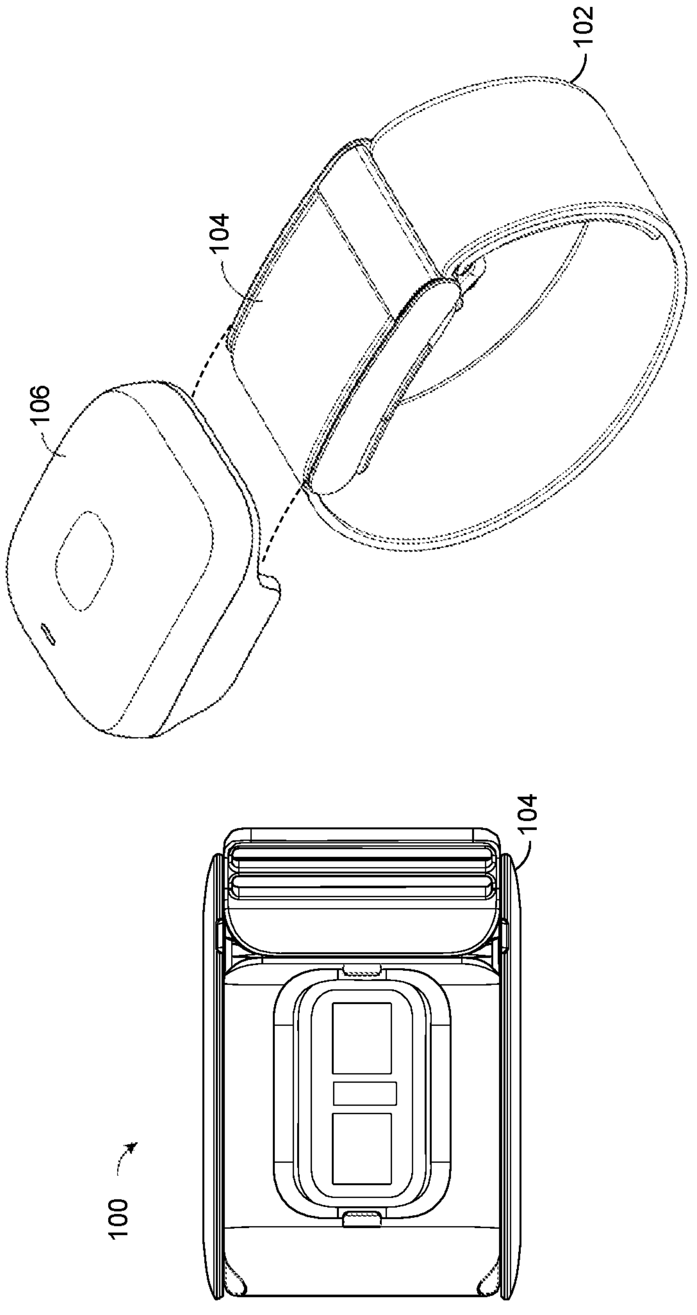
FIG. 1 shows a physiological monitoring device.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better describe the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," "above," "below," and the like, are words of convenience and are not to be construed as limiting terms unless specifically stated to the contrary.

Exemplary embodiments provide physiological measurement systems, devices and methods for continuous health and fitness monitoring, and provide improvements to overcome the drawbacks of conventional heart rate monitors. One aspect of the present disclosure is directed to providing a lightweight wearable system with a strap that collects various physiological data or signals from a wearer. The strap may be used to position the system on an appendage or extremity of a user, for example, wrist, ankle, and the like. Exemplary systems are wearable and enable real-time and continuous monitoring of heart rate without the need for a chest strap or other bulky equipment which could otherwise cause discomfort and prevent continuous wearing and use. The system may determine the user's heart rate without the use of electrocardiography and without the need for a chest strap. Exemplary systems can thereby be used in not only assessing general well-being but also in continuous monitoring of fitness. Exemplary systems also enable monitoring of one or more physiological parameters in addition to heart rate including, but not limited to, body temperature, heart rate variability, motion, sleep, stress, fitness level, recovery level, effect of a workout routine on health and fitness, caloric expenditure, and the like.

A health or fitness monitor that includes bulky components may hinder continuous wear. Existing fitness monitors often include the functionality of a watch, thereby making the health or fitness monitor quite bulky and inconvenient for continuous wear. Accordingly, one aspect is directed to providing a wearable health or fitness system that does not include bulky components, thereby making the bracelet slimmer, unobtrusive and appropriate for continuous wear. The ability to continuously wear the bracelet further allows continuous collection of physiological data, as well as continuous and more reliable health or fitness monitoring. For example, embodiments of the bracelet disclosed herein allow users to monitor data at all times, not just during a fitness session. In some embodiments, the wearable system may or may not include a display screen for displaying heart rate and other information. In other embodiments, the wearable system may include one or more light emitting diodes (LEDs) to provide feedback to a user and display heart rate selectively. In some embodiments, the wearable system may include a removable or releasable modular head that may provide additional features and may display additional information. Such a modular head can be releasably installed on the wearable system when additional information display is desired and removed to improve the comfort and appearance of the wearable system. In other embodiments, the head may be integrally formed in the wearable system.

Exemplary embodiments also include computer-executable instructions that, when executed, enable automatic interpretation of one or more physiological parameters to assess the cardiovascular intensity experienced by a user (embodied in an intensity score or indicator) and the user's recovery after physical exertion or daily stress given sleep and other forms of rest (embodied in a recovery score). These indicators or scores may be stored and displayed in a meaningful format to assist a user in managing his health and exercise regimen. Exemplary computer-executable instructions may be provided in a cloud implementation.

Exemplary embodiments also provide a vibrant and interactive online community, in the form of a website, for displaying and sharing physiological data among users. A user of the website may include an individual whose health or fitness is being monitored, such as an individual wearing a wearable system disclosed herein, an athlete, a sports team member, a personal trainer or a coach. In some embodiments, a user may pick his/her own trainer from a list to comment on their performance. Exemplary systems have the ability to stream all physiological information wirelessly, directly or through a mobile communication device application, to an online website using data transfer to a cell phone/computer. This information, as well as any data described herein, may be encrypted (e.g., the data may include encrypted biometric data). Thus, the encrypted data may be streamed to a secure server for processing. In this manner, only authorized users will be able to view the data and any associated scores. In addition, or in the alternative, the website may allow users to monitor their own fitness results, share information with their teammates and coaches, compete with other users, and win status. Both the wearable system and the website allow a user to provide feedback regarding his/her day, exercise and/or sleep, which enables recovery and performance ratings.

In an exemplary technique of data transmission, data collected by a wearable system may be transmitted directly to a cloud-based data storage, from which data may be downloaded for display and analysis on a website. In another exemplary technique of data transmission, data collected by a wearable system may be transmitted via a mobile communication device application to a cloud-based data storage, from which data may be downloaded for display and analysis on a website.

In some embodiments, the website may be a social networking site. In some embodiments, the website may be displayed using a mobile website or a mobile application. In some embodiments, the website may be configured to communicate data to other websites or applications. In some embodiments, the website may be configured to provide an interactive user interface. The website may be configured to display results based on analysis of physiological data received from one or more devices. The website may be configured to provide competitive ways to compare one user to another, and ultimately a more interactive experience for the user. For example, in some embodiments, instead of merely comparing a user's physiological data and performance relative to that user's past performances, the user may be allowed to compete with other users and the user's performance may be compared to that of other users.

Certain terms are defined below to facilitate understanding of exemplary embodiments.

The term "user" as used herein, refers to any type of animal, human or non-human, whose physiological information may be monitored using an exemplary wearable physiological monitoring system.

The term "body," as used herein, refers to the body of a user.

The term "continuous," as used herein in connection with heart rate data, refers to the acquisition of heart rate data at a sufficient frequency to enable detection of individual heartbeats, and also refers to the collection of heart rate data over extended periods such as an hour, a day or more (including acquisition throughout the day and night). More generally with respect to physiological signals that might be monitored by a wearable device, "continuous" or "continuously" will be understood to mean continuously at a rate and duration suitable for the intended time-based processing, and physically at an inter-periodic rate (e.g., multiple times per heartbeat, respiration, and so forth) sufficient for resolving the desired physiological characteristics such as heart rate, heart rate variability, heart rate peak detection, pulse shape, and so forth. At the same time, continuous monitoring is not intended to exclude ordinary data acquisition interruptions such as temporary displacement of monitoring hardware due to sudden movements, changes in external lighting, loss of electrical power, physical manipulation and/or adjustment by a wearer, physical displacement of monitoring hardware due to external forces, and so forth. It will also be noted that heart rate data or a monitored heart rate, in this context, may more generally refer to raw sensor data such as optical intensity signals, or processed data therefrom such as heart rate data, signal peak data, heart rate variability data, or any other physiological or digital signal suitable for recovering heart rate information as contemplated herein. Furthermore, such heart rate data may generally be captured over some historical period that can be subsequently correlated to various other data or metrics related to, e.g., sleep states, recognized exercise activities, resting heart rate, maximum heart rate, and so forth.

The term "pointing device," as used herein, refers to any suitable input interface, specifically, a human interface device, that allows a user to input spatial data to a computing system or device. In an exemplary embodiment, the pointing device may allow a user to provide input to the computer using physical gestures, for example, pointing, clicking, dragging, and dropping. Exemplary pointing devices may include, but are not limited to, a mouse, a touchpad, a touchscreen, and the like.

The term "multi-chip module," as used herein, refers to an electronic package in which multiple integrated circuits (IC) are packaged with a unifying substrate, facilitating their use as a single component, i.e., as a higher processing capacity IC packaged in a much smaller volume.

The term "computer-readable medium," as used herein, refers to a non-transitory storage media such as storage hardware, storage devices, computer memory that may be accessed by a controller, a microcontroller, a microprocessor, a computational system, or the like, or any other module or component or module of a computational system to encode thereon computer-executable instructions, software programs, and/or other data. The "computer-readable medium" may be accessed by a computational system or a module of a computational system to retrieve and/or execute the computer-executable instructions or software programs encoded on the medium. The non-transitory computer-readable media may include, but are not limited to, one or more types of hardware memory, non-transitory tangible media (for example, one or more magnetic storage disks, one or more optical disks, one or more USB flash drives), virtual or physical computer system memory, physical memory hardware such as random access memory (such as, DRAM, SRAM, EDO RAM), and so forth. Although not depicted, any of the devices or components described herein may include a computer-readable medium or other memory for storing program instructions, data, and the like.

The term "distal," as used herein, refers to a portion, end or component of a physiological measurement system that is farthest from a user's body when worn by the user.

The term "proximal," as used herein, refers to a portion, end or component of a physiological measurement system that is closest to a user's body when worn by the user.

The term "equal," as used herein, refers, in a broad lay sense, to exact equality or approximate equality within some tolerance.

I. Exemplary Wearable Physiological Measurement Systems

Exemplary embodiments provide wearable physiological measurements systems that are configured to provide continuous measurement of heart rate. Exemplary systems are configured to be continuously wearable on an appendage, for example, wrist or ankle, and do not rely on electrocardiography or chest straps in detection of heart rate. The exemplary system includes one or more light emitters for emitting light at one or more desired frequencies toward the user's skin, and one or more light detectors for received light reflected from the user's skin. The light detectors may include a photo-resistor, a phototransistor, a photodiode, and the like. As light from the light emitters (for example, green light) pierces through the skin of the user, the blood's natural absorbance or transmittance for the light provides fluctuations in the photo-resistor readouts. These waves have the same frequency as the user's pulse since increased absorbance or transmittance occurs only when the blood flow has increased after a heartbeat. The system includes a processing module implemented in software, hardware or a combination thereof for processing the optical data received at the light detectors and continuously determining the heart rate based on the optical data. The optical data may be combined with data from one or more motion sensors, e.g., accelerometers and/or gyroscopes, to minimize or eliminate noise in the heart rate signal caused by motion or other artifacts (or with other optical data of another wavelength).

FIG. 1 shows a physiological monitoring system. The system 100 may include a wearable monitor 104 that is configured for physiological monitoring. The system 100 may also include a removable and replaceable battery 106 for recharging the wearable monitor 104. The wearable monitor 104 may include a strap 102 or other retaining system(s) for securing the wearable monitor 104 in a position on a wearer's body for the acquisition of physiological data as described herein. For example, the strap 102 may include a slim elastic band formed of any suitable elastic material such as a rubber or a woven polymer fiber such as a woven polyester, polypropylene, nylon, spandex, and so forth. The strap 102 may be adjustable to accommodate different wrist sizes, and may include any latches, hasps, or the like to secure the wearable monitor 104 in an intended position for monitoring a physiological signal. While a wrist-worn device is depicted, it will be understood that the wearable monitor 104 may be configured for positioning in any suitable location on a user's body, based on the sensing modality and the nature of the signal to be acquired. For example, the wearable monitor 104 may be configured for use on a wrist, an ankle, a bicep, a chest, or any other suitable location(s), and the strap 102 may be, or may include, a waistband or other elastic band or the like within an article of clothing or accessory. The wearable monitor 104 may also or instead be structurally configured for placement on or within a garment, e.g., permanently or in a removable and replaceable manner. To that end, the wearable monitor 104 may be shaped and sized for placement within a pocket, slot, and/or other housing that is coupled to or embedded within a garment. In such configurations, the pocket or other retaining arrangement on the garment may include sensing windows or the like so that the wearable monitor 104 can operate while placed for use in the garment. U.S. Pat. No. 11,185,292 describes non-limiting example embodiments of suitable wearable monitors 104, and is incorporated herein by reference in its entirety.

The system 100 may include any hardware components, subsystems, and the like to support various functions of the wearable monitor 104 such as data collection, processing, display, and communications with external resources. For example, the system 100 may include hardware for a heart rate monitor using, e.g., photoplethysmography, electrocardiography, or any other technique(s). The system 100 may be configured such that, when the wearable monitor 104 is placed for use about a wrist (or at some other body location), the system 100 initiates acquisition of physiological data from the wearer. In some embodiments, the pulse or heart rate may be acquired optically based on a light source (such as light emitting diodes (LEDs)) and optical detectors in the wearable monitor 104. The LEDs may be positioned to direct illumination toward the user's skin, and optical detectors such as photodiodes may be used to capture illumination intensity measurements indicative of illumination from the LEDs that is reflected and/or transmitted by the wearer's skin.

The system 100 may be configured to record other physiological and/or biomechanical parameters including, but not limited to, skin temperature (using a thermometer), galvanic skin response (using a galvanic skin response sensor), motion (using one or more multi-axes accelerometers and/or gyroscope), blood pressure, and the like, as well environmental or contextual parameters such as ambient light, ambient temperature, humidity, time of day, and so forth. For example, the wearable monitor 104 may include sensors such as accelerometers and/or gyroscopes for motion detection, sensors for environmental temperature sensing, sensors to measure electrodermal activity (EDA), sensors to measure galvanic skin response (GSR) sensing, and so forth. The system 100 may also or instead include other systems or subsystems supporting addition functions of the wearable monitor 104. For example, the system 100 may include communications systems to support, e.g., near field communications, proximity sensing, Bluetooth communications, Wi-Fi communications, cellular communications, satellite communications, and so forth. The wearable monitor 104 may also or instead include components such as a GeoPositioning System (GPS), a display and/or user interface, a clock and/or timer, and so forth.

The wearable monitor 104 may include one or more sources of battery power, such as a first battery within the wearable monitor 104 and a second battery 106 that is removable from and replaceable to the wearable monitor 104 in order to recharge the battery in the wearable monitor 104. Also or instead, the system 100 may include a plurality of wearable monitors 104 (and/or other physiological monitors) that can share battery power or provide power to one another. The system 100 may perform numerous functions related to continuous monitoring, such as automatically detecting when the user is asleep, awake, exercising, and so forth, and such detections may be performed locally at the wearable monitor 104 or at a remote service coupled in a communicating relationship with the wearable monitor 104 and receiving data therefrom. In general, the system 100 may support continuous, independent monitoring of a physiological signal such as a heart rate, and the underlying acquired data may be stored on the wearable monitor 104 for an extended period until it can be uploaded to a remote processing resource for more computationally complex analysis.

In one aspect, the wearable monitor may be a wrist-worn photoplethysmography device.

Figure 2:
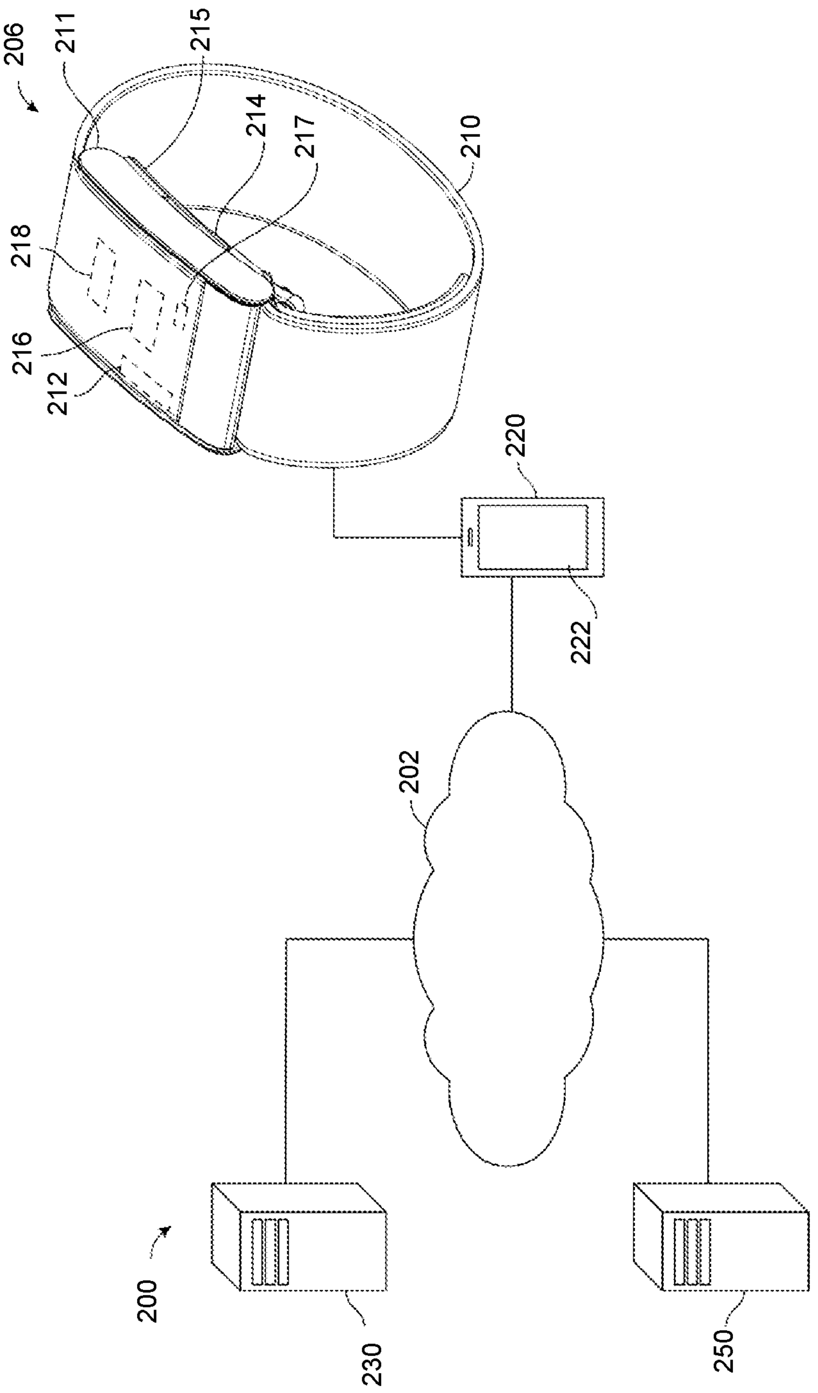
FIG. 2 illustrates a physiological monitoring system.

FIG. 2 illustrates a physiological monitoring system. More specifically, FIG. 2 illustrates a physiological monitoring system 200 that may be used with any of the methods or devices described herein. In general, the system 200 may include a physiological monitor 206, a user device 220, a remote server 230 with a remote data processing resource (such as any of the processors or processing resources described herein), and one or more other resources 250, all of which may be interconnected through a data network 202.

The data network 202 may be any of the data networks described herein. For example, the data network 202 may be any network(s) or internetwork(s) suitable for communicating data and information among participants in the system 200. This may include public networks such as the Internet, private networks, telecommunications networks such as the Public Switched Telephone Network or cellular networks using third generation (e.g., 3G or IMT-200), fourth generation (e.g., LTE (E-UTRA) or WiMAX-Advanced (IEEE 802.16m)), fifth generation (e.g., 5G), and/or other technologies, as well as any of a variety of corporate area or local area networks and other switches, routers, hubs, gateways, and the like that might be used to carry data among participants in the system 200. This may also include local or short-range communications infrastructure suitable, e.g., for coupling the physiological monitor 206 to the user device 220, or otherwise supporting communicating with local resources. By way of non-limiting examples, short range communications may include Wi-Fi communications, Bluetooth communications, infrared communications, near field communications, communications with RFID tags or readers, and so forth.

The physiological monitor 206 may, in general, be any physiological monitoring device or system, such as any of the wearable monitors or other monitoring devices or systems described herein. In one aspect, the physiological monitor 206 may be a wearable physiological monitor shaped and sized to be worn on a wrist or other body location. The physiological monitor 206 may include a wearable housing 211, a network interface 212, one or more sensors 214, one or more light sources 215, a processor 216, a haptic device 217 or other user input/output hardware, a memory 218, and a strap 210 for retaining the physiological monitor 206 in a desired location on a user. In one aspect, the physiological monitor 206 may be configured to acquire heart rate data and/or other physiological data from a wearer in an intermittent or substantially continuous manner. In another aspect, the physiological monitor 206 may be configured to support extended, continuous acquisition of physiological data, e.g., for several days, a week, or more.

The network interface 212 of the physiological monitor 206 may be configured to couple the physiological monitor 206 to one or more other components of the system 200 in a communicating relationship, either directly, e.g., through a cellular data connection or the like, or indirectly through a short range wireless communications channel coupling the physiological monitor 206 locally to a wireless access point, router, computer, laptop, tablet, cellular phone, or other device that can locally process data, and/or relay data from the physiological monitor 206 to the remote server 230 or other resource(s) 250 as necessary or helpful for acquiring and processing data from the physiological monitor 206.

The one or more sensors 214 may include any of the sensors described herein, or any other sensors or subsystems suitable for physiological monitoring or supporting functions. By way of example and not limitation, the one or more sensors 214 may include one or more of a light source, an optical sensor, an accelerometer, a gyroscope, a temperature sensor, a galvanic skin response sensor, a capacitive sensor, a resistive sensor, an environmental sensor (e.g., for measuring ambient temperature, humidity, lighting, and the like), a geolocation sensor, a Global Positioning System, a proximity sensor, an RFID tag reader, and RFID tag, a temporal sensor, an electrodermal activity sensor, and the like. The one or more sensors 214 may be disposed in the wearable housing 211, or otherwise positioned and configured for physiological monitoring or other functions described herein. In one aspect, the one or more sensors 214 include a light detector configured to provide light intensity data to the processor 216 (or to the remote server 230) for calculating a heart rate and a heart rate variability. The one or more sensors 214 may also or instead include an accelerometer, gyroscope, and the like configured to provide motion data to the processor 216, e.g., for detecting activities such as a sleep state, a resting state, a waking event, exercise, and/or other user activity. In an implementation, the one or more sensors 214 may include a sensor to measure a galvanic skin response of the user. The one or more sensors 214 may also or instead include electrodes or the like for capturing electronic signals, e.g., to obtain an electrocardiogram and/or other electrically-derived physiological measurements.

The processor 216 and memory 218 may be any of the processors and memories described herein. In one aspect, the memory 218 may store physiological data obtained by monitoring a user with the one or more sensors 214, and or any other sensor data, program data, or other data useful for operation of the physiological monitor 206 or other components of the system 200. It will be understood that, while only the memory 218 on the physiological monitor is illustrated, any other device(s) or components of the system 200 may also or instead include a memory to store program instructions, raw data, processed data, user inputs, and so forth. In one aspect, the processor 216 of the physiological monitor 206 may be configured to obtain heart rate data from the user, such as heart rate data including or based on the raw data from the sensors 214. The processor 216 may also or instead be configured to determine, or assist in a determination of, a condition of the user related to, e.g., health, fitness, strain, recovery sleep, or any of the other conditions described herein.

The one or more light sources 215 may be coupled to the wearable housing 211 and controlled by the processor 216. At least one of the light sources 215 may be directed toward the skin of a user adjacent to the wearable housing 211. Light from the light source 215, or more generally, light at one or more wavelengths of the light source 215, may be detected by one or more of the sensors 214, and processed by the processor 216 as described herein.

The system 200 may further include a remote data processing resource executing on a remote server 230. The remote data processing resource may include any of the processors and related hardware described herein, and may be configured to receive data transmitted from the memory 218 of the physiological monitor 206, and to process the data to detect or infer physiological signals of interest such as heart rate, heart rate variability, respiratory rate, pulse oxygen, blood pressure, and so forth. The remote server 230 may also or instead evaluate a condition of the user such as a recovery state, sleep state, exercise activity, exercise type, sleep quality, daily activity strain, and any other health or fitness conditions that might be detected based on such data.

The system 200 may include one or more user devices 220, which may work together with the physiological monitor 206, e.g., to provide a display, or more generally, user input/output, for user data and analysis, and/or to provide a communications bridge from the network interface 212 of the physiological monitor 206 to the data network 202 and the remote server 230. For example, physiological monitor 206 may communicate locally with a user device 220, such as a smartphone of a user, via short-range communications, e.g., Bluetooth, or the like, for the exchange of data between the physiological monitor 206 and the user device 220, and the user device 220 may in turn communicate with the remote server 230 via the data network 202 in order to forward data from the physiological monitor 206 and to receive analysis and results from the remote server 230 for presentation to the user. In one aspect, the user device(s) 220 may support physiological monitoring by processing or pre-processing data from the physiological monitor 206 to support extraction of heart rate or heart rate variability data from raw data obtained by the physiological monitor 206. In another aspect, computationally intensive processing may advantageously be performed at the remote server 230, which may have greater memory capabilities and processing power than the physiological monitor 206 and/or the user device 220.

The user device 220 may include any suitable computing device(s) including, without limitation, a smartphone, a desktop computer, a laptop computer, a network computer, a tablet, a mobile device, a portable digital assistant, a cellular phone, a portable media or entertainment device, or any other computing devices described herein. The user device 220 may provide a user interface 222 for access to data and analysis by a user, and/or to support user control of operation of the physiological monitor 206. The user interface 222 may be maintained by one or more applications executing locally on the user device 220, or the user interface 222 may be remotely served and presented on the user device 220, e.g., from the remote server 230 or the one or more other resources 250.

In general, the remote server 230 may include data storage, a network interface, and/or other processing circuitry. The remote server 230 may process data from the physiological monitor 206 and perform physiological and/or health monitoring/analyses or any of the other analyses described herein, (e.g., analyzing sleep, determining strain, assessing recovery, and so on), and may host a user interface for remote access to this data, e.g., from the user device 220. The remote server 230 may include a web server or other programmatic front end that facilitates web-based access by the user devices 220 or the physiological monitor 206 to the capabilities of the remote server 230 or other components of the system 200.

The system 200 may include other resources 250, such as any resources that can be usefully employed in the devices, systems, and methods as described herein. For example, these other resources 250 may include other data networks, databases, processing resources, cloud data storage, data mining tools, computational tools, data monitoring tools, algorithms, and so forth. In another aspect, the other resources 250 may include one or more administrative or programmatic interfaces for human actors such as programmers, researchers, annotators, editors, analysts, coaches, and so forth, to interact with any of the foregoing. The other resources 250 may also or instead include any other software or hardware resources that may be usefully employed in the networked applications as contemplated herein. For example, the other resources 250 may include payment processing servers or platforms used to authorize payment for access, content, or option/feature purchases. In another aspect, the other resources 250 may include certificate servers or other security resources for third-party verification of identity, encryption or decryption of data, and so forth. In another aspect, the other resources 250 may include a desktop computer or the like co-located (e.g., on the same local area network with, or directly coupled to through a serial or USB cable) with a user device 220, wearable strap 210, or remote server 230. In this case, the other resources 250 may provide supplemental functions for components of the system 200 such as firmware upgrades, user interfaces, and storage and/or pre-processing of data from the physiological monitor 206 before transmission to the remote server 230.

The other resources 250 may also or instead include one or more web servers that provide web-based access to and from any of the other participants in the system 200. While depicted as a separate network entity, it will be readily appreciated that the other resources 250 (e.g., a web server) may also or instead be logically and/or physically associated with one of the other devices described herein, and may for example, include or provide a user interface 222 for web access to the remote server 230 or a database or other resource(s) to facilitate user interaction through the data network 202, e.g., from the physiological monitor 206 or the user device 220.

In another aspect, the other resources 250 may include fitness equipment or other fitness infrastructure. For example, a strength training machine may automatically record repetitions and/or added weight during repetitions, which may be wirelessly accessible by the physiological monitor 206 or some other user device 220. More generally, a gym may be configured to track user movement from machine to machine, and report activity from each machine in order to track various strength training activities in a workout. The other resources 250 may also or instead include other monitoring equipment or infrastructure. For example, the system 200 may include one or more cameras to track motion of free weights and/or the body position of the user during repetitions of a strength training activity or the like. Similarly, a user may wear, or have embedded in clothing, tracking fiducials such as visually distinguishable objects for image-based tracking, or radio beacons or the like for other tracking. In another aspect, weights may themselves be instrumented, e.g., with sensors to record and communicated detected motion, and/or beacons or the like to self-identify type, weight, and so forth, in order to facilitate automated detection and tracking of exercise activity with other connected devices.

One limitation on wearable sensors can be body placement. Devices are typically wrist-based, and may occupy a location that a user would prefer to reserve for other devices or jewelry, or that a user would prefer to leave unadorned for aesthetic or functional reasons. This location also places constraints on what measurements can be taken, and may also limit user activities. For example, a user may be prevented from wearing boxing gloves while wearing a sensing device on their wrist. To address this issues, physiological monitors may also or instead be embedded in clothing, which may be specifically adapted for physiological monitoring with the addition of communications interfaces, power supplies, device location sensors, environmental sensors, geolocation hardware, payment processing systems, and any other components to provide infrastructure and augmentation for wearable physiological monitors. Such "smart garments" offer additional space on a user's body for supporting monitoring hardware, and may further enable sensing techniques that cannot be achieved with single sensing devices. Smart garments may also free up body surfaces for other devices.

It will be understood that a "smart garment" as described herein generally includes a garment that incorporates infrastructure and devices to support, augment, or complement various physiological monitoring modes. Such a garment may include a wired, local communication bus for intra-garment hardware communications, a wireless communication system for intra-garment hardware communications, a wireless communication system for extra-garment communications and so forth. The garment may also or instead include a power supply, a power management system, processing hardware, data storage, and so forth, any of which may support enriched functions for the smart garment.

Figure 3:
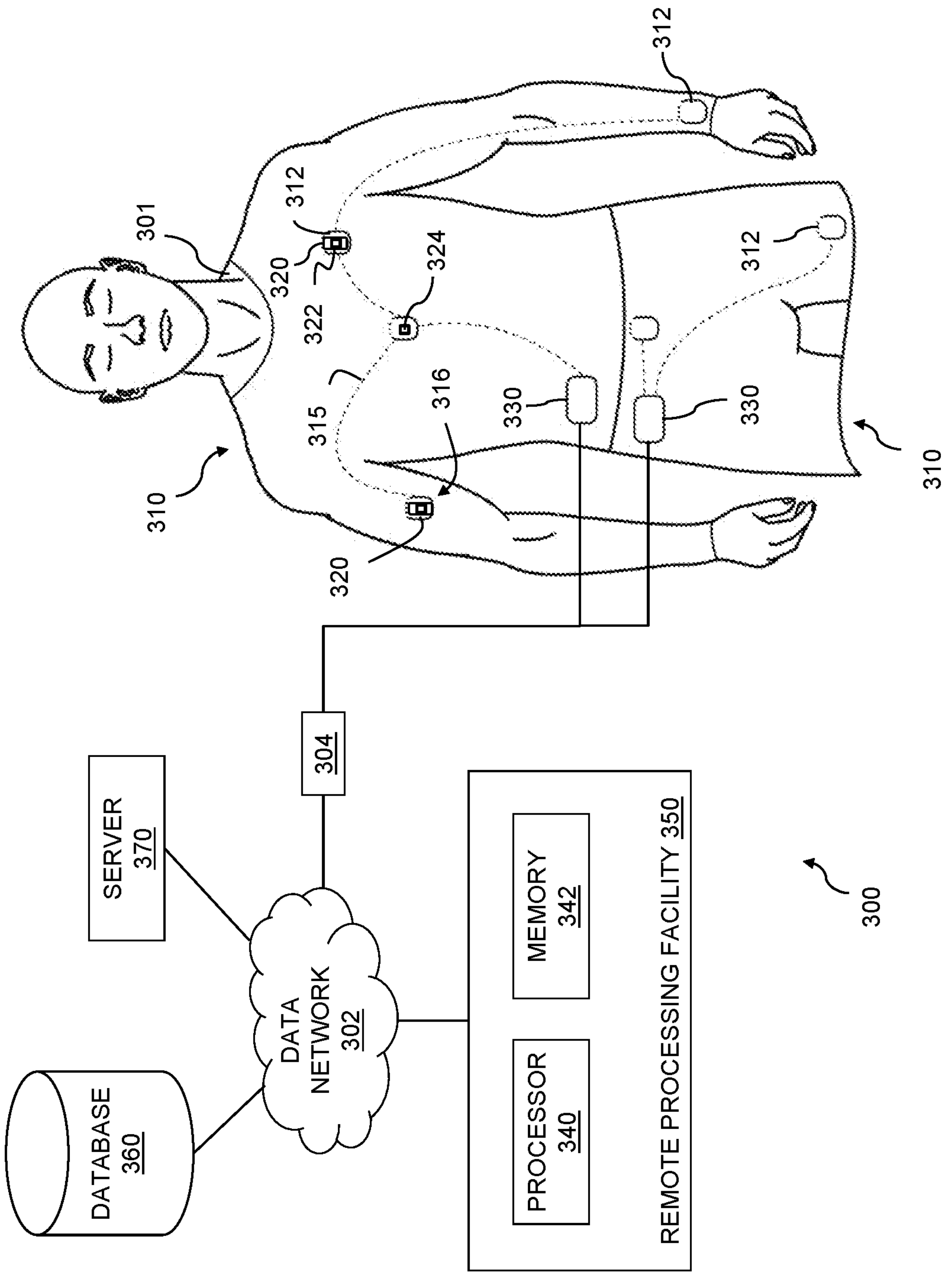
FIG. 3 shows a smart garment system.

FIG. 3 shows a smart garment system. In general, the system 300 may include a plurality of components—e.g., a garment 310, one or more modules 320, a controller 330, a processor 340, a memory 342, and so on—capable of communicating with one another over a data network 302. The garment 310 may be wearable by a user 301 and configured to communicate with a module 320 having a physiological sensor 322 that is structurally configured to sense a physiological parameter of the user 301. As discussed herein, the module 320 may be controllable by the controller 330 based at least in part on a location 316 where the module 320 is located on or within the garment 310. This position-based information may be derived from an interaction and/or communication between the module 320 and the garment 310 using various techniques. It will be understood that, while two controllers 330 are shown, the garment 310 may include a single inter-garment controller, or any number of separate controllers 330 in any number of garments 310 (e.g., one per garment, or one for all garments worn by a person, etc.), and/or controllers may be integrated into other modules 320.

For communication over the data network 302, the system 300 may include a network interface 304, which may be integrated into the garment 310, included in the controller

330, or in some other module or component of the system 300, or some combination of these. The network interface 304 may generally include any combination of hardware and software configured to wirelessly communicate data to remote resources. For example, the network interface 304 may use a local connection to a laptop, smart phone, or the like that couples, in turn, to a wide area network for accessing, e.g., web-based or other network-accessible resources. The network interface 304 may also or instead be configured to couple to a local access point such as a router or wireless access point for connecting to the data network 302. In another aspect, the network interface 304 may be a cellular communications data connection for direct, wireless connection to a cellular network or the like.

The data network 302 may be any as described herein. By way of example, some embodiments of the system 300 may be configured to stream information wirelessly to a social network, a data center, a cloud service, and so forth. In some embodiments, data streamed from the system 300 to the data network 302 may be accessed by the user 301 (or other users) via a website. The network interface 304 may thus be configured such that data collected by the system 300 is streamed wirelessly to a remote processing facility 350, database 360, and/or server 370 for processing and access by the user. In some embodiments, data may be transmitted automatically, without user interactions, for example by storing data locally and transmitting the data over available local area network resources when a local access point such as a wireless access point or a relay device (such as a laptop, tablet, or smart phone) is available. In some embodiments, the system 300 may include a cellular system or other hardware for independently accessing network resources from the garment 310 without requiring local network connectivity. It will be understood that the network interface 304 may include a computing device such as a mobile phone or the like. The network interface 304 may also or instead include or be included on another component of the system 300, or some combination of these. Where battery power or communications resources can advantageously be conserved, the system 300 may preferentially use local networking resources when available, and reserve cellular communications for situations where a data storage capacity of the garment 310 is reaching capacity. Thus, for example, the garment 310 may store data locally up to some predetermined threshold for local data storage, below which data is transmitted over local networks when available. The garment 310 may also transmit data to a central resource using a cellular data network only when local storage of data exceeds the predetermined threshold.

The garment 310 may include one or more designated areas 312 for positioning a module to sense a physiological parameter of the user 301 wearing the garment 310. One or more of the designated areas 312 may be specifically tailored for receiving a module 320 therein or thereon. For example, a designated area 312 may include a pocket structurally configured to receive a module 320 therein. Also or instead, a designated area 312 may include a first fastener configured to cooperate with a second fastener disposed on a module 320. One or more of the first fastener and the second fastener may include at least one of a hook-and-loop fastener, a button, a clamp, a clip, a snap, a projection, and a void.

By placing a pocket or the like in one of these designated areas 312, a position of a module 320 can be controlled, and where an RFID tag, sensor, or the like is used, the designated area 312 can specifically sense when a module 320 is positioned there for monitoring, and can communicate the detected location to any suitable control circuitry.

The garment 310 may also or instead incorporate other infrastructure 315 to cooperate with a module 320. For example, the garment infrastructure 315 may include infrastructure 315 related to ECG devices, such as ECG pads (or otherwise electrically conductive sensor pads and/or electrodes that connect to the module 320, controller 330, and/or another component of the system 300), lead wires, and the like. By way of further example, the garment infrastructure 315 may include wires or the like embedded in the garment 310 to facilitate wired data or power transfer between installed modules 320 and other system components (including other modules 320). The infrastructure 315 may also or instead include integrated features for, e.g., powering modules, supporting data communications among modules, and otherwise supporting operation of the system 300. The infrastructure 314 may also or instead include location or identification tags or hardware, a power supply for powering modules 320 or other hardware, communications infrastructure as described herein, a wired intra-garment network, or supplemental components such as a processor, a Global Positioning System (GPS), a timing device, e.g., for synchronizing signals from multiple garments, a beacon for synchronizing signals among multiple modules 320, and so forth. More generally, any hardware, software, or combination of these suitable for augmenting operation of the garment 310 and a physiological monitoring system using the garment 310 may be incorporated as infrastructure 315 into the garment 310 as contemplated herein.

The modules 320 may generally be sized and shaped for placement on or within the one or more designated areas 312 of the garment 310. For example, in certain implementations, one or more of the modules 320 may be permanently affixed on or within the garment 310. In such instances, the modules 320 may be washable. Also or instead, in certain implementations, one or more of the modules 320 may be removable and replaceable relative to the garment 310. In such instances, the modules 320 need not be washable, although a module 320 may be designed to be washable and/or otherwise durable enough to withstand a prolonged period of engagement with a designated area 312 of the garment 310. A module 320 may be capable of being positioned in more than one of the designated areas 312 of the garment 310. That is, one or more of the plurality of modules 320 may be configured to sense data using a physiological sensor 322 in a plurality of designated areas 312 of the garment 310.

A module 320 may include one or more physiological sensors 322 and a communications interface 324 programmed to transmit data from at least one of the physiological sensors 322. For example, the physiological sensors 322 may include one or more of a heart rate monitor (e.g., one or more PPG sensors or the like), an oxygen monitor (e.g., a pulse oximeter), a blood pressure monitor, a thermometer, an accelerometer, a gyroscope, a position sensor, a Global Positioning System, a clock, a galvanic skin response (GSR) sensor, or any other electrical, acoustic, optical, or other sensor or combination of sensors and the like useful for physiological monitoring, environmental monitoring, or other monitoring as described herein. In one aspect, the physiological sensors 322 may include a conductivity sensor or the like used for electromyography, electrocardiography, electroencephalography, or other physiological sensing based on electrical signals. The data received from the physiological sensors 322 may include at least one of heart rate data and/or similar data related to blood flow (e.g., from PPG sensors), muscle oxygen saturation data, temperature data, movement data, position/location data, environmental data, temporal data, blood pressure data, and so on.

Thus, certain embodiments include one or more physiological sensors 322 configured to provide continuous measurements of heart rate using photoplethysmography or the like. The physiological sensor 322 may include one or more light emitters for emitting light at one or more desired frequencies toward the user's skin, and one or more light detectors for received light reflected from the user's skin. The light detectors may include a photo-resistor, a phototransistor, a photodiode, and the like. A processor may process optical data from the light detector(s) to calculate a heart rate based on the measured, reflected light. The optical data may be combined with data from one or more motion sensors, e.g., accelerometers and/or gyroscopes, to minimize or eliminate noise in the heart rate signal caused by motion or other artifacts. The physiological sensor 322 may also or instead provide at least one of continuous motion detection, environmental temperature sensing, electrodermal activity (EDA) sensing, galvanic skin response (GSR) sensing, and the like.

The system 300 may include different types of modules 320. For example, a number of different modules 320 may each provide a particular function. Thus, the garment 310 may house one or more of a temperature module, a heart rate/PPG module, a muscle oxygen saturation module, a haptic module, a wireless communication module, or combinations thereof, any of which may be integrated into a single module 320 or deployed in separate modules 320 that can communicate with one another. Some measurements such as temperature, motion, optical heart rate detection, and the like, may have preferred or fixed locations, and pockets or fixtures within the garment 310 may be adapted to receive specific types of modules 320 at specific locations within the garment 310. For example, motion may preferentially be detected at or near extremities while heart rate data may preferentially be gathered near major arteries. In another aspect, some measurements such as temperature may be measured anywhere, but may preferably be measured at a single location in order to avoid certain calibration issues that might otherwise arise through arbitrary placement.

In another aspect, the system 300 may include two or more modules 320 placed at different locations and configured to perform differential signal analysis. For example, the rate of pulse travel and the degree of attenuation in a cardiac signal may be detected using two or more modules at two or more locations, e.g., at the bicep and wrist of a user, or at other locations similarly positioned along an artery. These multiple measurements support a differential analysis that permits useful inferences about heart strength, pliability of circulatory pathways, blood pressure, and other aspects of the cardiovascular system that may indicate cardiac age, cardiac health, cardiac conditions, and so forth. Similarly, muscle activity detection might be measured at different locations to facilitate a differential analysis for identifying activity types, determining muscular fitness, and so forth. More generally, multiple sensors can facilitate differential analysis. To facilitate this type of analysis with greater precision, the garment infrastructure may include a beacon or clock for synchronizing signals among multiple modules, particularly where data is temporarily stored locally at each module, or where the data is transmitted to a processor from different locations wirelessly where packet loss, latency, and the like may present challenges to real time processing.

The communications interface 324 may be any as described herein, for example including any of the features of the network interface 304 described above.

The controller 330 may be configured, e.g., by computer executable code or the like, to determine a location of the module 320. This may be based on contextual measurements such as accelerometer data from the module 320, which may be analyzed by a machine learning model or the like to infer a body position. In another aspect, this may be based on other signals from the module 320. For example, signals from sensors such as photodiodes, temperature sensors, resistors, capacitors, and the like may be used alone or in combination to infer a body position. In another aspect, the location may be determined based on a proximity of a module 320 to a proximity sensor, RFID tag, or the like at or near one of the designated areas 312 of the garment 310. Based on the location, the controller 330 may adapt operation of the module 320 for location-specific operation. This may include selecting filters, processing models, physiological signal detections, and the like. It will be understood that operations of the controller 330, which may be any controller, microcontroller, microprocessor, or other processing circuitry, or the like, may be performed in cooperation with another component of the system 300 such as the processor 340 described herein, one or more of the modules 320, or another computing device. It will also be understood that the controller 330 may be located on a local component of the system 300 (e.g., on the garment 310, in a module 320, and so on) or as part of a remote processing facility 350, or some combination of these. Thus, in an aspect, a controller 330 is included in at least one of the plurality of modules 320. And, in another aspect, the controller 330 is a separate component of the garment 310, and serves to integrate functions of the various modules 320 connected thereto. The controller 330 may also or instead be remote relative to each of the plurality of modules 320, or some combination of these.

The controller 330 may be configured to control one or more of (i) sensing performed by a physiological sensor 322 of the module 320 and (ii) processing by the module 320 of the data received from a physiological sensor 322. That is, in certain aspects, the combination of sensors in the module 320 may vary based on where it is intended to be located on a garment 310. In another aspect, processing of data from a module 320 may vary based on where it is located on a garment 310. In this latter aspect, a processing resource such as the controller 330 or some other local or remote processing resource coupled to the module 320 may detect the location and adapt processing of data from the module 320 based on the location. This may, for example, include a selection of different models, algorithms, or parameters for processing sensed data.

In another aspect, this may include selecting from among a variety of different activity recognition models based on the detected location. For example, a variety of different activity recognition models may be developed such as machine learning models, lookup tables, analytical models, or the like, which may be applied to accelerometer data to detect an activity type. Other motion data such as gyroscope data may also or instead be used, and activity recognition processes may also be augmented by other potentially relevant data such as data from a barometer, magnetometer, GPS system, and so forth. This may generally discriminate, e.g., between being asleep, at rest, or in motion, or this may discriminate more finely among different types of athletic activity such as walking, running, biking, swimming, playing tennis, playing squash, and so forth. While useful models may be developed for detecting activities in this manner, the nature of the detection will depend upon where the accelerometers are located on a body. Thus, a processing resource may usefully identify location first using location detection systems (such as tags, electromechanical bus connections, etc.) built into the garment 310, and then use this detected location to select a suitable model for activity recognition. This technique may similarly be applied to calibration models, physiological signals processing models, and the like, or to otherwise adapt processing of signals from a module 320 based on the location of the module 320.

Determining the location of a module 320 may include receiving a sensed location for the module 320. The sensed location may be provided by a proximity detection circuit such as a near-field-communication (NFC) tag, an (active or passive) RFID tag, a capacitance sensor, a magnetic sensor, an electrical contact, a mechanical contact, and the like. Any corresponding hardware for such proximity detections may be disposed on the module 320 and the garment 310 for communication therebetween to detect location when appropriate. For example, in one aspect, an NFC tag may be disposed on or within the garment 310, and the module may include an NFC tag sensor 320 that can detect the tag and read any location-specific information therefrom. Proximity detection may also or instead be performed using capacitively detected contact, electromagnetically detected proximity, mechanical contact, electrical coupling, and the like. In this manner, a garment 310 may provide information to an installed module 320 to inform the module 320, among other things, where the module 320 is located, or vice-versa.

Thus, communication between a module 320 and the garment 310 (or a processor of the garment 310) may be used to determine the location of a module 320 on the garment 310. Communication of location information may be enabled using active techniques, passive techniques, or a combination thereof. For example, a thin, flexible, cheap, washable NFC tag may be sewn into the garment 310 in various locations where a module 320 may be placed. When a module 320 is placed in the garment 310, the module 320 may query an adjacent NFC tag to determine its location. Furthermore, the NFC technique or other similar techniques may provide other information to the module 320, including details about the garment 310 such as the size, whether it is a gender specific piece, the manufacturer information, model or serial number of the garment, stock keeping unit (SKU), and more. Similarly, the tag may encode a unique identifier for the garment 310 that can be used to obtain other relevant information using an online resource. The module 320 may also or instead advertise information about itself to the garment 310 so that the garment 310 can synchronize processing with other modules 320, synchronize communication among modules 320, control or condition signals from the module 320, and so forth. The module 320 can then configure itself within the context of the current garment 310 and associated modules 320, and/or to perform certain types of monitoring or data processing.

Determining the location of a module 320 may also or instead be based, at least in part, on an interpretation of the data received from a physiological sensor 322 of the module 320. By way of example, movement of a module 320 as detected by a sensor may provide information that can be used to predict a position on or within the garment 310. Also or instead, the type of data that is being received from a module 320 may indicate where the module 320 is located on the garment 310. For example, locations may produce unique signatures of acceleration, gyroscope activity, capacitive data, optical data, temperature data, and the like, depending on where the module 320 is located, and this data may be fused and analyzed in any suitable manner to obtain a location prediction.

According to the foregoing, determining the location of a module 320 may also or instead include receiving explicit input from the user 301, which may identify one of the designated areas on the garment 310, or a general area of the body (e.g., left wrist, right ankle, and so forth). Because the location of the module 320 relative to the garment 310 may be determined from an analysis of a plurality of data sources, the system 300 may include a component (e.g., the processor 340) that is configured to reconcile one or more potential sources of location of information based on expected reliability, measured quality of data, express user input, and so forth. A prediction confidence may also usefully be generated in this context, which may be used, for example, to determine whether a user should be queried for more specific location information. More generally, any of the foregoing techniques may be used along or in combination, along with a failsafe measure the requests user input when location cannot confidently be predicted. Also or instead, a user may explicitly specify a prediction preemptively, or as an override to an automatically generated prediction.

Once determined using any of the techniques above, the location of a module 320 may be transmitted for storage and analysis to a remote processing facility 350, a database 360, or the like. That is, in addition to the module 320 using this information locally to configure itself for the location in which it is worn, the module 320 may communicate this information to other modules 320, peripherals, or the cloud. Processing this information in the cloud may help an organization determine if a module 320 has ever been installed on a garment 310, which locations are most used, and how modules 320 perform differently in different locations. These analytics may be useful for many purposes, and may, for example, be used to improve the design or use of modules 320 and garments 310, either for a population, for a user type, or for a particular user.

As stated above, the system 300 may further include a processor 340 and a memory 342. In general, the memory 342 may bear computer executable code configured to be executed by the processor 340 to perform processing of the data received from one or more modules 320. One or more of the processor 340 and the memory 342 may be located on a local component of the system 300 (e.g., the garment 310, a module 320, the controller 330, and the like) or as part of a remote processing facility 350 or the like as shown in the figure. Thus, in an aspect, one or more of the processor 340 and the memory 342 is included on at least one of the plurality of modules 320. In this manner, processing may be performed on a central module, or on each module 320 independently. In another aspect, one or more of the processor 340 and the memory 342 is remote relative to each of the plurality of modules 320. For example, processing may be performed on a connected peripheral device such as smart phone, laptop, local computer, or cloud resource.

The memory 342 may store one or more algorithms, models, and supporting data (e.g., parameters, calibration results, user selections, and so forth) and the like for transforming data received from a physiological sensor 322 of the module 320. In this manner, suitable models, algorithms, tuning parameters, and the like may be selected for use in transforming the data based on the location of the module 320 as determined by the controller 330 and/or processor 340 as described herein. By way of example, algorithms that convert data from an accelerometer in a module 320 into activity data or a count of a user's steps may be different depending on whether the module 320 is worn on the user's wrist or on the user's waist band. Similarly, the intensity of an LED and corresponding sensitivity of a photodetector may be different for a PPG device placed on the wrist or the thigh. Thus, the module 320 may self-configure for a location by controlling one or more of sensor types, sensor parameters, processing models, and so forth based on a detected location for the module 320.

Selection of an algorithm may also or instead include an analysis of one or more of the sensor data, metadata, and the like. By way of example, an algorithm may be selected at least in part based on metadata received from one of the module 320 and the garment 310. This metadata may be derived from communication between the module 320 and the garment 310—e.g., between a tag and tag reader for exchanging information therebetween. For example, the garment 310 may include, e.g., stored in a tag such as an NFC tag or other wirelessly readable data source, garment-specific metadata that is readable by or otherwise transmittable to one or more of the plurality of modules 320, the controller 330, and the processor 340. Such garment-specific metadata may include at least one of a type of garment 310, a size of the garment 310, garment dimensions, a gender configuration of the garment 310, a manufacturer, a model number, a serial number, a SKU, a material, fit information, and so on. In one aspect, this information may be provided with one or more of the location identification tags described herein. In another aspect, the garment 310 may include an additional tag at a suitable location (e.g., near or accessible to a processor or controller) that provides garment-specific information while other tags provide location-specific information.

The metadata may also or instead include at least one of a gender of the user 301, a weight of the user 301, a height of the user 301, an age of the user 301, metadata associated with the garment 310 (e.g., the garment size, type, material, etc.), and the like. The metadata may be derived, at least in part, from user-provided input, or otherwise from information derived from the user 301 such as a user's account information as a participant in the system 300. By way of example, a processing algorithm may be selected depending on the material of the garment 301 as communicated by its serial or model number in an identification tag, the physiology of the user 301 as implied by the garment size, and so on. The metadata may also or instead be used to verify the authenticity of the garment 310, and otherwise control access to the garment 310 and/or modules 320 coupled to the garment 310. In one aspect, metadata (e.g., size, material) may be encoded directly into the garment metadata. In another aspect, the garment 310 may publish a unique identifier that can be used to retrieve related information from a manufacturer or other data source. This latter approach advantageously permits correlation of garment-specific data with other user-specific data such as height, weight, body composition, and so forth.

Simply knowing a priori where a module 320 is positioned may allow for the use of algorithms that have been developed to perform optimally in that particular location. This can relieve a significant computational burden otherwise borne by the module 320 to analytically evaluate location based on available signals. Other information may also or instead be used to select an optimal algorithm. For example, based on the gender or dimensions of a garment, the algorithm may employ different models or different model parameters.

The processor 340 may be configured to assess the quality of the data received from a physiological sensor 322 of the module 320. For example, the processor 340 may be configured to provide, based on the quality of the data, a recommendation regarding at least one of the location of a module 320 and an aspect of the garment 310 (e.g., size, fit, material, and so on). For example, the processor 340 may be configured to detect when the garment does not properly fit the wearer for acquisition of physiological data, for example, by detecting when a module is moving (e.g., from accelerometer data) but data quality is poor or absent for a sensed physiological signal. In general, the garment 310 may store its own identifier and/or metadata, e.g., as described herein, or garment identification data may be stored in tags, e.g., at designated areas 312 of the garment 310. The processor 340 may be configured to use this garment identification information and/or metadata to provide a recommendation regarding a different garment 310 for the user 301, or for an adjustment to the current garment 310. For example, if a particular garment 310 seems to result in low-quality data, the user 301 could be encouraged to select an alternative size, or to make some other adjustment. Moreover, data on how many times a garment 301 is used may be gathered and used to inform business decisions, for example, which garments 301 provide the highest-quality data, and which garments 310 are most preferred by users 301.

The system 300 may further include a database 360, which may be located remotely and in communication with the system 300 via the data network 302. The database 360 may store data related to the system 300 such as any discussed herein—e.g., sensed data, processed data, transformed data, metadata, physiological signal processing models and algorithms, personal activity history, and the like. The system 300 may further include one or more servers 370 that host data, provide a user interface, process data, and so forth in order to facilitate use of the modules 320 and garments 310 as described herein.

It will be appreciated that the garment 310, modules 320, and accompanying garment infrastructure and remote networking/processing resources, may advantageously be used in combination to improve physiological monitoring and achieve modes of monitoring not previously available.

One or more of the devices and systems described herein may include circuitry for both wireless charging and wireless data transmission, e.g., where the corresponding circuits can operate independently from one another, and where the corresponding antennae are located proximal to one another (for instance, the circuitry for wireless charging and the circuitry for wireless data transmission may include separate coils disposed substantially along the same plane, or otherwise in relative close proximity in a device or system). In such aspects, one or more measures may be taken so that a wireless data transfer process does not interfere with a wireless power transfer process, more specifically by coupling the data circuitry into the electromagnetic field for the wireless power transfer in a manner that alters the resonant frequency or otherwise destructively interferes with power transfer, thereby decreasing efficiency when charging a device. For example, a switch may be included to disable circuitry for data transmission when certain wireless charging activity is present, thereby allowing for relatively unimpeded and efficient wireless charging of a device. The switch may also be operable to enable operation of data transmission circuitry when certain wireless charging activity is not present.

Thus, for example, in the context of a physiological monitor, such as any of those described herein, the physiological monitor may include both a wireless power receiver (or similar) and a wireless data tag reader (or similar). In general, these sub-systems may conform to one or more Near Field Communication (NFC) specifications for protocols and physical architectures, or any other standards suitable for wireless power and data transmission. The power circuitry may be used, e.g., to charge a battery on the physiological monitor so that the device can be recharged without physically connecting to a power source. The data circuitry may be used, e.g., as a wireless data tag reader or the like to read data from nearby data sources such as identification tags in user apparel and the like. In general, the physiological monitor may include separate circuitry (separate coils) for these wireless power and data systems, such as separate processing circuitry and/or separate antennae. The antennae may be disposed substantially along the same plane of the physiological monitor (e.g., with one coil disposed substantially inside or adjacent to the other). In one aspect, the antennae may be in parallel planes, however, it will be noted that distance tolerances for NFC standard devices are relatively small, and the physically housing for these antennae will preferably enforce an identical or substantially identical distance for both antennae in such architectures. In this context, the positions of the antennae may be as close to parallel as possible within reasonable manufacturing tolerances, or as close to parallel as possible when disposed on two different layers of a shared printed circuit board, or preferably, when disposed on a single layer of a shared printed circuit board. The physiological monitor may further include a switch (e.g., a radio frequency (RF) switch or the like) in-line with the coil for the wireless data tag reader to disable the wireless data tag reader when power is being received to mitigate any effects on the efficiency of the wireless power transfer process. In particular, the switch may be configured to open when power is being received, and may be configured to close when the physiological monitor is looking for data tag to read.

Figure 4:
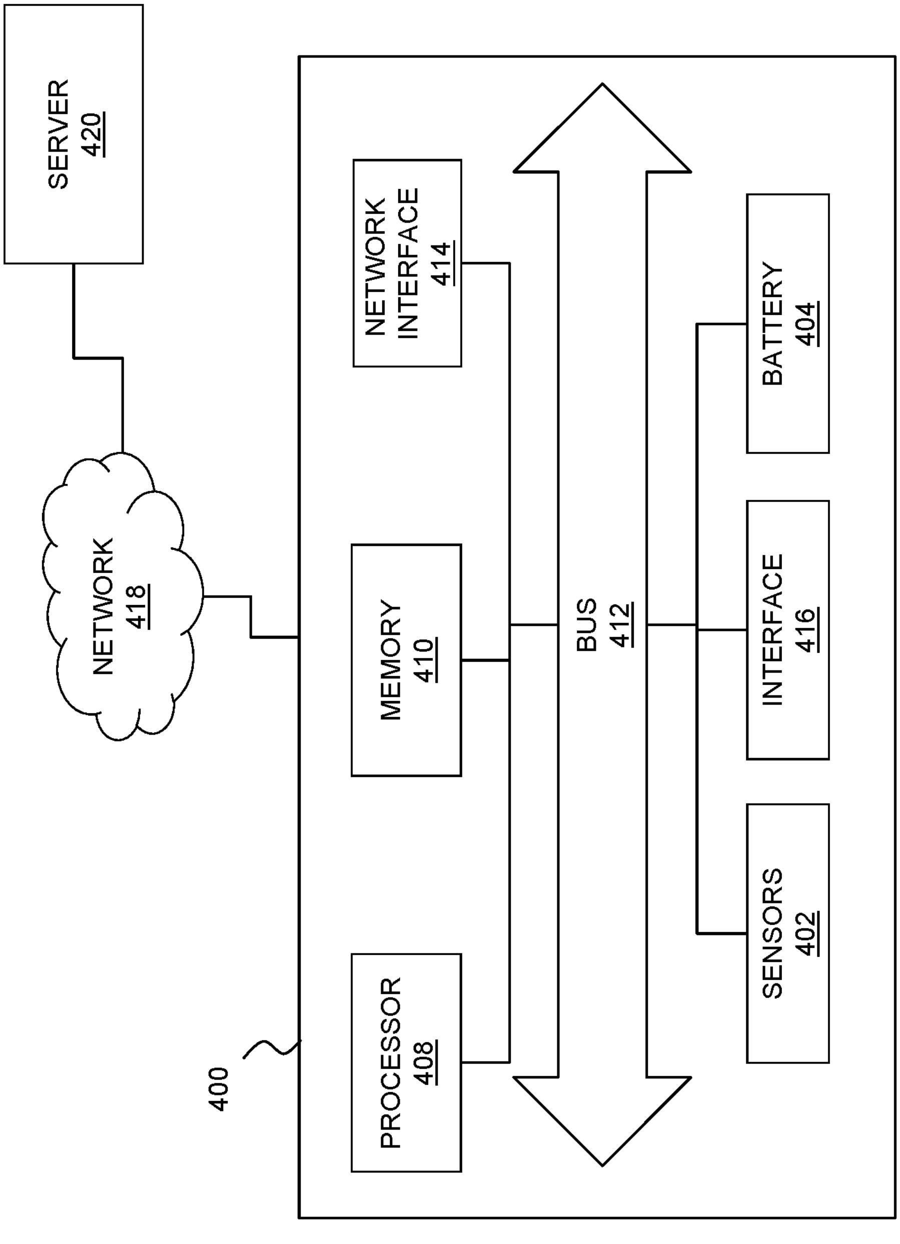
FIG. 4 is a block diagram of a computing device.

FIG. 4 is a block diagram of a computing device 400. The computing device 400 may, for example, be a device used for continuous physiological monitoring, or any other device supporting a physiological monitor in the systems and methods described herein. The device may also or instead be any of the local computing devices described herein, such as a desktop computer, laptop computer, smart phone. The device may also or instead be any of the remote computing resources described herein, such as a web server, a cloud database, a file server, an application server, or any other remote resource or the like. While described as a physical device, it will be understood that the exemplary computing device 400 may also or instead be realized as a virtual computing device such as a virtual machine executing a web server or other remote resource in a cloud computing platform. In general, the device 400 may include one or more sensors 402, a battery 404, storage 406, a processor 408, memory 410, a network interface 414, and a user interface 416, or virtual instances of one or more of the foregoing.

The sensors 402 may include any sensor or combination of sensors suitable for heart rate monitoring as contemplated herein, as well as sensors 402 for detecting calorie burn, position (e.g., through a Global Positioning System or the like), motion, activity and so forth. In one aspect, this may include optical sensing systems including LEDs or other light sources, along with photodiodes or other light sensors, that can be used in combination for photoplethysmography measurements of heart rate, pulse oximetry measurements, and other physiological monitoring.

The sensors 402 may also or instead include one or more sensors for activity measurement. In some embodiments, the system may include one or more multi-axes accelerometers and/or gyroscope to provide a measurement of activity. In some embodiments, the accelerometer may further be used to filter a signal from the optical sensor for measuring heart rate and to provide a more accurate measurement of the heart rate. In some embodiments, the wearable system may include a multi-axis accelerometer to measure motion and calculate distance. Motion sensors may be used, for example, to classify or categorize activity, such as walking, running, performing another sport, standing, sitting or lying down. The sensors 402 may, for example, include a thermometer for monitoring the user's body or skin temperature. In one embodiment, the sensors 402 may be used to recognize sleep based on a temperature drop, Galvanic Skin Response data, lack of movement or activity according to data collected by the accelerometer, reduced heart rate as measured by the heart rate monitor, and so forth. The body temperature, in conjunction with heart rate monitoring and motion, may be used, e.g., to interpret whether a user is sleeping or just resting, as well as how well an individual is sleeping. The body temperature, motion, and other sensed data may also be used to determine whether the user is exercising, and to categorize and/or analyze activities as described in greater detail below. In another aspect, the sensors 402 may include one or more contact sensors, such as a capacitive touch sensor or resistive touch sensor, for detecting placement of a physiological monitor for use on a user. More generally, the sensors 402 may include any sensor or combination of sensors suitable for monitoring geographic location, physiological state, exertion, movement, and so forth in any manner useful for physiological monitoring as contemplated herein.

The battery 404 may include one or more batteries configured to allow continuous wear and usage of the wearable system. In one embodiment, the wearable system may include two or more batteries, such as a removable battery that may be removed and recharged using a charger, along with an integral battery that maintains operation of the device 400 while the main battery charges. In another aspect, the battery 404 may include a wireless rechargeable battery that can be recharged using a short range or long range wireless recharging system.

The processor 408 may include any microprocessor, microcontroller, signal processor or other processor or combination of processors and other processing circuitry suitable for performing the processing steps described herein. In general, the processor 408 may be configured by computer executable code stored in the memory 410 to provide activity recognition and other physiological monitoring functions described herein.

In general the memory 410 may include one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, optical disks, USB flash drives), and the like. In one aspect, the memory 410 may include a computer system memory or random access memory, such as DRAM, SRAM, EDO RAM, and the like. The memory 410 may include other types of memory as well, or combinations thereof, as well as virtual instances of memory, e.g., where the device is a virtual device. In general, the memory 410 may store computer readable and computer-executable instructions or software for implementing methods and systems described herein. The memory 410 may also or instead store physiological data, user data, or other data useful for operation of a physiological monitor or other device described herein, such as data collected by sensors 402 during operation of the device 400.

The network interface 414 may be configured to wirelessly communicate data to a server 420, e.g., through an external network 418 such as any public network, private network, or other data network described herein, or any combination of the foregoing including, e.g., local area networks, the Internet, cellular data networks, and so forth. Where the device is a physiological monitoring device, the network interface 414 may be used, e.g., to transmit raw or processed sensor data stored on the device 400 to the server 420, as well as to receive updates, receive configuration information, and otherwise communicate with remote resources and the user to support operation of the device. More generally, the network interface 414 may include any interface configured to connect with one or more networks, for example, a Local Area Network (LAN), a Wide Area Network (WAN), the Internet, or a cellular data network through a variety of connections including, but not limited to, standard telephone lines, LAN or WAN links (for example, 802.11, T1, T3, 56 kb, X.25), broadband connections (for example, ISDN, Frame Relay, ATM), wireless connections, or some combination of any or all of the above. The network interface 412 may include a built-in network adapter, network interface card, PCMCIA network card, card bus network adapter, wireless network adapter, USB network adapter, modem or any other device suitable for interfacing the computing device 400 to any type of network capable of communication and performing the operations described herein.

The user interface 416 may include any components suitable for supporting interaction with a user. This may, for example, include a keypad, display, buzzer, speaker, light emitting diodes, capacitive touch sensors or pads, and any other components for receiving input from, or providing output to, a user. In one aspect, the device 400 may be configured to receive tactile input, such as by responding to sequences of taps on a surface of the device to change operating states, display information and so forth. The user interface 416 may also or instead include a graphical user interface rendered on a display for graphical user interaction with programs executing on the processor 408 and other content rendered by a physical display of device 400.

Techniques to observe, monitor, analyze, and/or provide coaching or other recommendations regarding stress are described below. By way of background and context—stress, as used herein, may include any measurable physiological and/or psychological response to stimuli. For example, psychological stress may be triggered by stimuli such as work pressure, financial difficulties, relationship problems, and health concerns. At the same time, physiological stress may be triggered by physical demands, sleep cycles, and so forth. At times, an observed stress response may be caused by either of these sources (physiological or psychological), or a combination of both.

In one aspect, it may be useful to distinguish between physiological stresses induced by physical activity, and psychological stresses induced by psychological stressors. For example, when faced with a perceived threat, the brain sends signals to the hypothalamus, which activates the sympathetic nervous system. This triggers the release of hormones like adrenaline and cortisol, which increase heart rate, breathing rate, and blood pressure. In small amounts, this type of stress can be helpful as it can motivate a person to take action and cope with challenging situations. However, if a person experiences chronic or excessive stress of this type, this can have negative effects on the person's mental and physical health, e.g., leading to anxiety, depression, fatigue, and a weakened immune system. At the same time, physiological stress responses may be a healthy reaction to vigorous activity. Nonetheless, incremental monitoring of physiological stress responses can support intra-day updates to performance metrics, coaching recommendations, and the like, e.g., to support updated strain calculations, real time recommendations concerning new or ongoing exercise, diet, and so forth.

As a significant advantage, the techniques described herein can facilitate monitoring and management of psychological and physiological stressors in real time or near real time. As another advantage, the techniques described herein can facilitate the separate measurement of both physical and emotional stress responses, e.g., to permit the isolation and analysis of contributions to physical and emotional stimuli to a current stress state.

Figure 5:
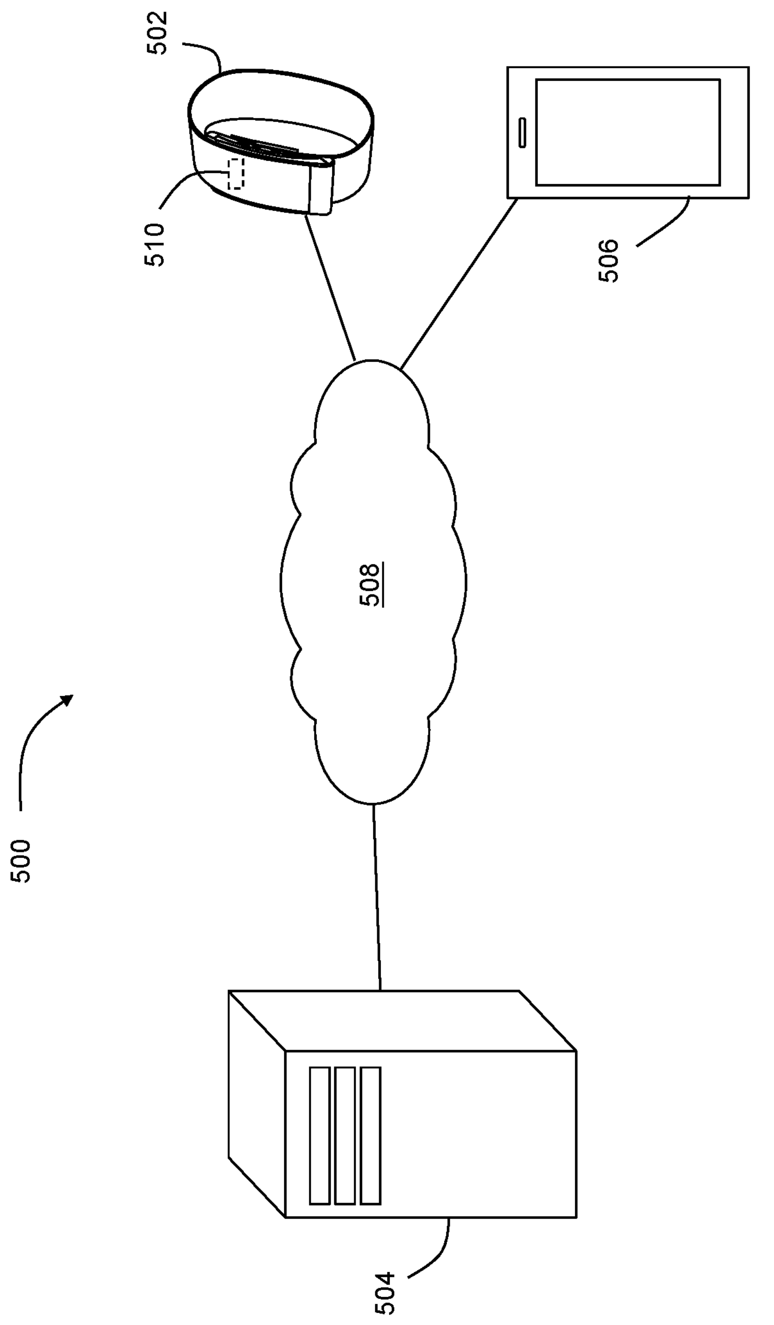
FIG. 5 shows a system for dynamic stress monitoring.

FIG. 5 shows a system for dynamic monitoring. In general, a physiological monitoring system 500 may include a wearable device 502 such as any of the physiological monitors described herein, a remote resource 504 such as any of the servers or other remote processing resources described herein, and a user device 506 such as any of the user devices described herein, along with a data network 508 interconnecting these devices in a communicating relationship.

The wearable device 502 may continuously monitor, measure, and/or calculate physiological parameters such as heart rate, heart rate variability, temperature, electrical properties (e.g., electrodermal activity and the like), blood pressure, stress, and motion, and transmit this data to a remote resource 504 over the data network 508. Based on this data, the remote resource may calculate metrics such as a daily sleep score (evaluating a prior night's sleep), a daily strain score (evaluating a prior day's strain), or a daily recovery score (evaluating the current readiness for new strain), for example using techniques described by way of non-limiting example in U.S. Pat. No. 10,264,982, the entire content of which is hereby incorporated by reference. This server-based approach advantageously permits offloading of data-intensive and computationally-intensive processing to a remote server or other suitably capable computing system, e.g., for metrics that are based on heart rate and motion data for an entire twenty four hour interval. However, this approach is less effective for incremental updates to data and recommendations over the course of the day.

Thus, the techniques described herein may advantageously be deployed to dynamically monitor activity over the course of the day, and update a user's metrics and coaching recommendations as appropriate. More specifically, a dynamic monitor 510 may be deployed locally on the wearable device 502, or at some other convenient location (such as the user device 506) where it can perform frequent local calculations to dynamically update user information. This approach also advantageously facilitates quick detection of significant stress events or the like so that suitable interventions can be recommended. It will be understood that in this context, "dynamic" scoring refers to scoring that is performed incrementally between static, remote calculations for long intervals such as a day or several hours. While this dynamic scoring necessarily occurs at discrete intervals, the scoring may be updated in any periodic or substantially continuous manner, such that user can receive timely quantitative evaluations. For example, this may include updates that are as close to instantaneous as possible, so that they are experienced by the user in real time with little or no observable latency. In another aspect, where the calculations are more computationally complex and/or are processed remotely, a current score for any metric may be calculated and updated for the user at an interval such as once per minute, or at some shorter or longer interval suitable for consumption by the user. This may also include changing the frequency, e.g., to update more frequently and/or provide more current calculations while a user is viewing the stress score. More generally, any quantity or frequency of updates that facilitates dynamic tracking of the user, and/or that supports feedback to the user on a current state, may be used to support tracking and reporting of a user's current state of subjective or physiological stress.

Figure 6:
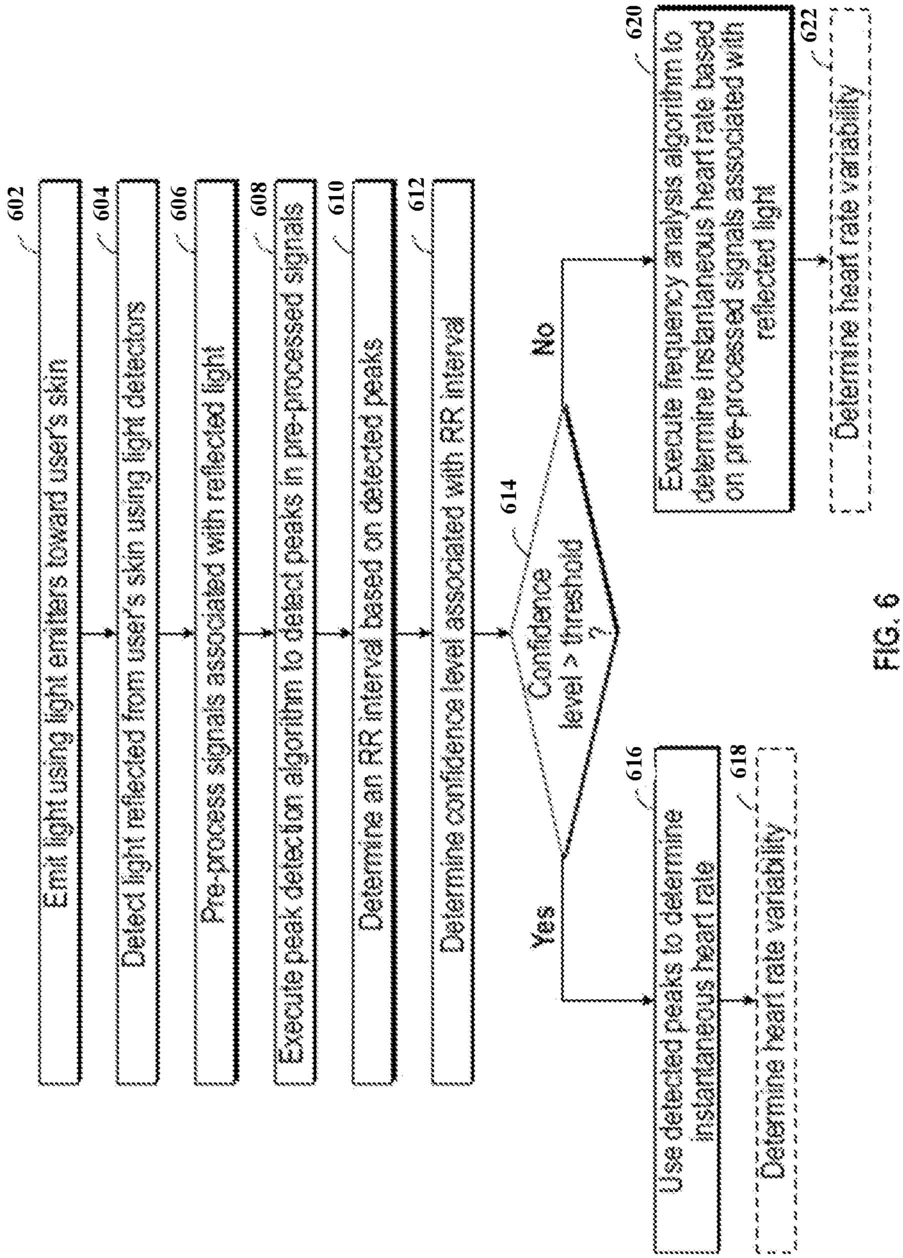
FIG. 6 is a flow chart illustrating a signal processing algorithm for generating a sequence of heart rates for every detected heartbeat that may be embodied in computer-executable instructions stored on one or more non-transitory computer-readable media.

FIG. 6 is a flow chart illustrating an exemplary signal processing algorithm for generating a sequence of heart rates for every detected heartbeat that is embodied in computer-executable instructions stored on one or more non-transitory computer-readable media. In step 602, light emitters of a wearable physiological measurement system emit light toward a user's skin. In step 604, light reflected from the user's skin is detected at the light detectors in the system. In step 606, signals or data associated with the reflected light are pre-processed using any suitable technique to facilitate detection of heart beats. In step 608, a processing module of the system executes one or more computer-executable instructions associated with a peak detection algorithm to process data corresponding to the reflected light to detect a plurality of peaks associated with a plurality of beats of the user's heart. In step 610, the processing module determines an RR interval based on the plurality of peaks detected by the peak detection algorithm. In step 612, the processing module determines a confidence level associated with the RR interval.

Based on the confidence level associated with the RR interval estimate, the processing module selects either the peak detection algorithm or a frequency analysis algorithm to process data corresponding to the reflected light to determine the sequence of instantaneous heart rates of the user. The frequency analysis algorithm may process the data corresponding to the reflected light based on the motion of the user detected using, for example, an accelerometer. The processing module may select the peak detection algorithm or the frequency analysis algorithm regardless of a motion status of the user. It is advantageous to use the confidence in the estimate in deciding whether to switch to frequency-based methods as certain frequency-based approaches are unable to obtain accurate RR intervals for heart rate variability analysis. Therefore, an implementation maintains the ability to obtain the RR intervals for as long as possible, even in the case of motion, thereby maximizing the information that can be extracted.

For example, in step 614, it is determined whether the confidence level associated with the RR interval is above (or equal to or above) a threshold. In certain embodiments, the threshold may be predefined, for example, about 50%-90% in some embodiments and about 80% in one non-limiting embodiment. In other embodiments, the threshold may be adaptive, i.e., the threshold may be dynamically and automatically determined based on previous confidence levels. For example, if one or more previous confidence levels were high (i.e., above a certain level), the system may determine that a present confidence level that is relatively low compared to the previous levels is indicative of a less reliable signal. In this case, the threshold may be dynamically adjusted to be higher so that a frequency-based analysis method may be selected to process the less reliable signal.

If the confidence level is above (or equal to or above) the threshold, in step 616, the processing module may use the plurality of peaks to determine an instantaneous heart rate of the user. On the other hand, in step 620, based on a determination that the confidence level associated with the RR interval is equal to or below the predetermined threshold, the processing module may execute one or more computer-executable instructions associated with the frequency analysis algorithm to determine an instantaneous heart rate of the user. The confidence threshold may be dynamically set based on previous confidence levels.

In some embodiments, in steps 618 or 622, the processing module determines a heart rate variability of the user based on the sequence of the instantaneous heart rates/beats.

The system may include a display device configured to render a user interface for displaying the sequence of the instantaneous heart rates of the user, the RR intervals and/or the heart rate variability determined by the processing module. The system may include a storage device configured to store the sequence of the instantaneous heart rates, the RR intervals and/or the heart rate variability determined by the processing module.

In one aspect, the system may switch between different analytical techniques for determining a heart rate such as a statistical technique for detecting a heart rate and a frequency domain technique for detecting a heart rate. These two different modes have different advantages in terms of accuracy, processing efficiency, and information content, and as such may be useful at different times and under different conditions. Rather than selecting one such mode or technique as an attempted optimization, the system may usefully switch back and forth between these differing techniques, or other analytical techniques, using a predetermined criterion. For example, where statistical techniques are used, a confidence level may be determined and used as a threshold for switching to an alternative technique such as a frequency domain technique. The threshold may also or instead depend on historical, subjective, and/or adapted data for a particular user. For example, selection of a threshold may depend on data for a particular user including without limitation subjective information about how a heart rate for a particular user responds to stress, exercise, and so forth. Similarly, the threshold may adapt to changes in fitness of a user, context provided from other sensors of the wearable system, signal noise, and so forth.

An exemplary statistical technique employs probabilistic peak detection. In this technique, a discrete probabilistic step may be set, and a likelihood function may be established as a mixture of a Gaussian random variable and a uniform. The heart of the likelihood function encodes the assumption that with a first probability (p) the peak detection algorithm has produced a reasonable initial estimate, but with a second probability (1−p) it has not. In a subsequent step, Bayes' rule is applied to determine the posterior density on the parameter space, of which the maximum is taken (that is, the argument (parameter) that maximizes the posterior distribution). This value is the estimate for the heart rate. In a subsequent step, the previous two steps are reapplied for the rest of the sample. There is some variance in the signal due to process noise, which is dependent on the length of the interval. This process noise becomes the variance in the Gaussians used for the likelihood function. Then, the estimate is obtained as the maximum a posteriori on the new posterior distribution. A confidence value is recorded for the estimate which, for some precision measurement, the posterior value is summed at points in the parameter space centered at our estimate +/− the precision.

The beats per minute (BPM) parameter space, θ, may range between about 20 and about 240, corresponding to the empirical bounds on human heart rates. In an exemplary method, a probability distribution is calculated over this parameter space, at each step declaring the mode of the distribution to be the heart rate estimate. A discrete uniform prior may be set:

$$\pi_1 \sim \text{DiscUnif}(\theta)$$

The un-normalized, univariate likelihood is defined by a mixture of a Gaussian function and a uniform:

$$l_1 \sim IG + (1-I)U, G \sim N(\gamma_1 \sigma^2), I \sim Ber(p)$$

where $$U \sim \text{DiscUnif}(\theta)$$

and where σ and p are predetermined constants.

Bayes' rule is applied to determine the posterior density on θ, for example, by component-wise multiplying the prior density vector $(\pi_1(\theta))_{\theta \in \Theta}$ with the likelihood vector $(l_1(\theta))_{\theta \in \Theta}$ to obtain the posterior distribution η1. Then, the following is set:

$$\beta_1 = \text{argmax}_{\theta \in \theta} \eta_1(\theta)$$

For k≥2, the variance in signal S(t) due to process noise is determined. Then, the following variable is set to imbue temporally long RR intervals with more process/interpeak noise and set the post-normalization convolution:

$$\pi_k = \eta_{k-1} * f_{N(o,\lambda_k^2)}|_\theta$$

where f is a density function of the following:

$$Z \sim N(o, \lambda_k^2)$$

Then, the following expressions are calculated:

$$l_k \sim pG_k + (1-p)U, G_k \sim N(\lambda k, \sigma^2)$$

The expression is then normalized and recorded:

$$\beta_k = \text{argmax}_{\theta \in \theta} \eta_k(\theta)$$

Finally, the confidence level of the above expression for a particular precision threshold is determined:

$$C_k = \sum\nolimits_{\theta \in [\beta_k - e_1, \beta_k + e] \cap \theta} \eta_k.$$

An exemplary frequency analysis algorithm used in an implementation isolates the highest frequency components of the optical data, checks for harmonics common in both the accelerometer data and the optical data, and performs filtering of the optical data. The algorithm takes as input raw analog signals from the accelerometer (3-axis) and pulse sensors, and outputs heart rate values or beats per minute (BPM) for a given period of time related to the window of the spectrogram.

The isolation of the highest frequency components is performed in a plurality of stages, gradually winnowing the window-sizes of consideration, thereby narrowing the range of errors. In one implementation, a spectrogram of 2^15 samples with overlap 2^13 samples of the optical data is generated. The spectrogram is restricted to frequencies in which heart rate can lie. These restriction boundaries may be updated when smaller window sizes are considered. The frequency estimate is extracted from the spectrogram by identifying the most prominent frequency component of the spectrogram for the optical data. The frequency may be extracted using the following exemplary steps. The most prominent frequency of the spectrogram is identified in the signal. It is determined if the frequency estimate is a harmonic of the true frequency. The frequency estimate is replaced with the true frequency if the estimate is a harmonic of the true frequency. It is determined if the current frequency estimate is a harmonic of the motion sensor data. The frequency estimate is replaced with a previous temporal estimate if it is a harmonic of the motion sensor data. The upper and lower bounds on the frequency obtained are saved. A constant value may be added or subtracted in some cases. In subsequent steps, the constant added or subtracted may be reduced to provide narrower searches. A number of the previous steps are repeated one or more times, e.g., three times, except taking 2^{15−i} samples for the window size and 2^{13−i} for the overlap in the spectrogram where i is the current number of iteration. The final output is the average of the final symmetric endpoints of the frequency estimation.

The table below demonstrates the performance of the algorithm disclosed herein. To arrive at the results below, experiments were conducted in which a subject wore an exemplary wearable physiological measurement system and a 3-lead ECG which were both wired to the same micro-controller (e.g., Arduino) in order to provide time-synced data. Approximately 50 data sets were analyzed which included the subject standing still, walking, and running on a treadmill.

TABLE 1

Performance of signal processing algorithm disclosed herein

| | Clean data error (mean, std) in BPM | Noisy data error (mean, std) in BPM |
|---|---|---|
| 4-level spectrogram (80 second blocks) | 0.2, 2.3 | 0.8, 5.1 |

The algorithm's performance comes from a combination of a probabilistic and frequency based approach. The three difficulties in creating algorithms for heart rate calculations from the PPG data are 1) false detections of beats, 2) missed detections of real beats, and 3) errors in the precise timing of the beat detection. The algorithms disclosed herein provide improvements in these three sources of error and, in some cases, the error is bound to within 2 BPM of ECG values at all times even during the most motion intense activities.

The exemplary wearable system computes heart rate variability (HRV) to obtain an understanding of the recovery status of the body. These values are captured right before a user awakes or when the user is not moving, in both cases photoplethysmography (PPG) variability yielding equivalence to the ECG HRV. HRV is traditionally measured using an ECG machine and obtaining a time series of R-R intervals. Because an exemplary wearable system utilizes photoplethysmography (PPG), it does not obtain the electric signature from the heart beats; instead, the peaks in the obtained signal correspond to arterial blood volume. At rest, these peaks are directly correlated with cardiac cycles, which enables the calculation of HRV via analyzing peak-to-peak intervals (the PPG analog of RR intervals). It has been demonstrated in the medical literature that these peak-to-peak intervals, the "PPG variability," is identical to ECG HRV while at rest. See, Charlot K, et al. "Interchangeability between heart rate and photoplethysmography variabilities during sympathetic stimulations." *Physiological Measurement*. 2009 December; 30(12): 1357-69. doi: 10.1088/0967-3334/30/12/005. URL: http://www.ncbi.nlm.nih.gov/pubmed/19864707; and Lu, S, et. al. "Can photoplethysmography variability serve as an alternative approach to obtain heart rate variability information?" *Journal of Clinical Monitoring and Computing*. 2008 February; 22(1):23-9. URL: http://www.ncbi.nlm.nih.gov/pubmed/17987395, the entire contents of which are incorporated herein by reference.

Exemplary physiological measurement systems are configured to minimize power consumption so that the systems may be worn continuously without requiring power recharging at frequent intervals. The majority of current draw in an exemplary system is allocated to power the light emitters, e.g., LEDs, the wireless transceiver, the microcontroller and peripherals. In one embodiment, the circuit board of the system may include a boost converter that runs a current of about 10 mA through each of the light emitters with an efficiency of about 80% and may draw power directly from the batteries at substantially constant power. With exemplary batteries at about 3.7 V, the current draw from the battery may be about 40 mW. In some embodiments, the wireless transceiver may draw about 10-20 mA of current when it is actively transferring data. In some embodiments, the microcontroller and peripherals may draw about 5 mA of current.

An exemplary system may include a processing module that is configured to automatically adjust one or more operational characteristics of the light emitters and/or the light detectors to minimize power consumption while ensuring that all heart beats of the user are reliably and continuously detected. The operational characteristics may include, but are not limited to, a frequency of light emitted by the light emitters, the number of light emitters activated, a duty cycle of the light emitters, a brightness of the light emitters, a sampling rate of the light detectors, and the like.

The processing module may adjust the operational characteristics based on one or more signals or indicators obtained or derived from one or more sensors in the system including, but not limited to, a motion status of the user, a sleep status of the user, historical information on the user's physiological and/or habits, an environmental or contextual condition (e.g., ambient light conditions), a physical characteristic of the user (e.g., the optical characteristics of the user's skin), and the like.

In one embodiment, the processing module may receive data on the motion of the user using, for example, an accelerometer. The processing module may process the motion data to determine a motion status of the user which indicates the level of motion of the user, for example, exercise, light motion (e.g., walking), no motion or rest, sleep, and the like. The processing module may adjust the duty cycle of one or more light emitters and the corresponding sampling rate of the one or more light detectors based on the motion status. For example, upon determining that the motion status indicates that the user is at a first higher level of motion, the processing module may activate the light emitters at a first higher duty cycle and sample the reflected light using light detectors sampling at a first higher sampling rate. Upon determining that the motion status indicates that the user is at a second lower level of motion, the processing module may activate the light emitters at a second lower duty cycle and sample the reflected light using light detectors sampling at a second lower sampling rate. That is, the duty cycle of the light emitters and the corresponding sampling rate of the light detectors may be adjusted in a graduated or continuous manner based on the motion status or level of motion of the user. This adjustment ensures that heart rate data is detected at a sufficiently high frequency during motion to reliably detect all of the heart beats of the user.

In non-limiting examples, the light emitters may be activated at a duty cycle ranging from about 1% to about 100%. In another example, the light emitters may be activated at a duty cycle ranging from about 20% to about 50% to minimize power consumption. Certain exemplary sampling rates of the light detectors may range from about 50 Hz to about 1000 Hz, but are not limited to these exemplary rates. Certain non-limiting sampling rates are, for example, about 100 Hz, 200 Hz, 500 Hz, and the like.

In one non-limiting example, the light detectors may sample continuously when the user is performing an exercise routine so that the error standard deviation is kept within 5 beats per minute (BPM). When the user is at rest, the light detectors may be activated for about a 1% duty cycle-10 milliseconds each second (i.e., 1% of the time) so that the error standard deviation is kept within 5 BPM (including an error standard deviation in the heart rate measurement of 2 BPM and an error standard deviation in the heart rate changes between measurement of 3 BPM). When the user is in light motion (e.g., walking), the light detectors may be activated for about a 10% duty cycle-100 milliseconds each second (i.e., 10% of the time) so that the error standard deviation is kept within 6 BPM (including an error standard deviation in the heart rate measurement of 2 BPM and an error standard deviation in the heart rate changes between measurement of 4 BPM).

The processing module may adjust the brightness of one or more light emitters by adjusting the current supplied to the light emitters. For example, a first level of brightness may be set by current ranging between about 1 mA to about 10 mA, but is not limited to this exemplary range. A second higher level of brightness may be set by current ranging from about 11 mA to about 30 mA, but is not limited to this exemplary range. A third higher level of brightness may be set by current ranging from about 80 mA to about 120 mA, but is not limited to this exemplary range. In one non-limiting example, first, second and third levels of brightness may be set by current of about 5 mA, about 20 mA and about 100 mA, respectively.

In some embodiments, the processing module may detect an environmental or contextual condition (e.g., level of ambient light) and adjust the brightness of the light emitters accordingly to ensure that the light detectors reliably detect light reflected from the user's skin while minimizing power consumption. For example, if it is determined that the ambient light is at a first higher level, the brightness of the light emitters may be set at a first higher level. If it is determined that the ambient light is at a second lower level, the brightness of the light emitters may be set at a second lower level. In some cases, the brightness may be adjusted in a continuous manner based on the detected environment condition.

In some embodiments, the processing module may detect a physiological condition of the user (e.g., an optical characteristic of the user's skin) and adjust the brightness of the light emitters accordingly to ensure that the light detectors reliably detect light reflected from the user's skin while minimizing power consumption. For example, if it is determined that the user's skin is highly reflective, the brightness of the light emitters may be set at a first lower level. If it is determined that the user's skin is not very reflective, the brightness of the light emitters may be set at a second higher level.

Shorter-wavelength LEDs may require more power than is required by longer-wavelength LEDs. Therefore, an exemplary wearable system may provide and use light emitted at two or more different frequencies based on the level of motion detected in order to save battery life. For example, upon determining that the motion status indicates that the user is at a first higher level of motion (e.g., exercising), one or more light emitters may be activated to emit light at a first wavelength. Upon determining that the motion status indicates that the user is at a second lower level of motion (e.g., at rest), one or more light emitters may be activated to emit light at a second wavelength that is longer than the first wavelength. Upon determining that the motion status indicates that the user is at a third lower level of motion (e.g., sleeping), one or more light emitters may be activated to emit light at a third wavelength that is longer than the first and second wavelengths. Other levels of motion may be predetermined and corresponding wavelengths of emitted light may be selected. The threshold levels of motion that trigger adjustment of the light wavelength may be based on one or more factors including, but are not limited to, skin properties, ambient light conditions, and the like. Any suitable combination of light wavelengths may be selected, for example, green (for a higher level of motion)/red (for a lower level of motion); red (for a higher level of motion)/infrared (for a lower level of motion); blue (for a higher level of motion)/green (for a lower level of motion); and the like.

Shorter-wavelength LEDs may require more power than is required by other types of heart rate sensors, such as, a piezo-sensor or an infrared sensor. Therefore, an exemplary wearable system may provide and use a unique combination of sensors—one or more light detectors for periods where motion is expected and one or more piezo and/or infrared sensors for low motion periods (e.g., sleep)—to save battery life. Certain other embodiments of a wearable system may exclude piezo-sensors and/or infrared sensors.

For example, upon determining that the motion status indicates that the user is at a first higher level of motion (e.g., exercising), one or more light emitters may be activated to emit light at a first wavelength. Upon determining that the motion status indicates that the user is at a second lower level of motion (e.g., at rest), non-light based sensors may be activated. The threshold levels of motion that trigger adjustment of the type of sensor may be based on one or more factors including, but are not limited to, skin properties, ambient light conditions, and the like.

The system may determine the type of sensor to use at a given time based on the level of motion (e.g., via an accelerometer) and whether the user is asleep (e.g., based on movement input, skin temperature and heart rate). Based on a combination of these factors the system selectively chooses which type of sensor to use in monitoring the heart rate of the user. Common symptoms of being asleep are periods of no movement or small bursts of movement (such as shifting in bed), lower skin temperature (although it is not a dramatic drop from normal), drastic GSR changes, and heart rate that is below the typical resting heart rate when the user is awake. These variables depend on the physiology of a person and thus a machine learning algorithm is trained with user-specific input to determine when he/she is awake/asleep and determine from that the exact parameters that cause the algorithm to deem someone asleep.

In an exemplary configuration, the light detectors may be positioned on the underside of the wearable system and all of the heart rate sensors may be positioned adjacent to each other. For example, the low power sensor(s) may be adjacent to the high power sensor(s) as the sensors may be chosen and placed where the strongest signal occurs. In one example configuration, a 3-axis accelerometer may be used that is located on the top part of the wearable system.

In some embodiments, the processing module may be configured to automatically adjust a rate at which data is transmitted by the wireless transmitter to minimize power consumption while ensuring that raw and processed data generated by the system is reliably transmitted to external computing devices. In one embodiment, the processing module determines an amount of data to be transmitted (e.g., based on the amount of data generated since the time of the last data transmission), and may select the next data transmission time based on the amount of data to be transmitted. For example, if it is determined that the amount of data exceeds (or is equal to or greater than) a threshold level, the processing module may transmit the data or may schedule a time for transmitting the data. On the other hand, if it is determined that the amount of data does not exceed (or is equal to or lower than) the threshold level, the processing module may postpone data transmission to minimize power consumption by the transmitter. In one non-limiting example, the threshold may be set to the amount of data that may be sent in two seconds under current conditions. Exemplary data transmission rates may range from about 50 kbytes per second to about 1 MByte per second, but are not limiting to this exemplary range.

In some embodiments, an operational characteristic of the microprocessor may be automatically adjusted to minimize power consumption. This adjustment may be based on a level of motion of the user's body.

More generally, the above description contemplates a variety of techniques for sensing conditions relating to heart rate monitoring or related physiological activity either directly (e.g., confidence levels or accuracy of calculated heart rate) or indirectly (e.g., motion detection, temperature). However measured, these sensed conditions can be used to intelligently select from among a number of different modes, including hardware modes, software modes, and combinations of the foregoing, for monitoring heart rate based on, e.g., accuracy, power usage, detected activity states, and so forth. Thus there is disclosed herein techniques for selecting from among two or more different heart rate monitoring modes according to a sensed condition.

II. Exemplary Physiological Analytics System

Exemplary embodiments provide an analytics system for providing qualitative and quantitative monitoring of a user's body, health and physical training. The analytics system is implemented in computer-executable instructions encoded on one or more non-transitory computer-readable media. The analytics system relies on and uses continuous data on one or more physiological parameters including, but not limited to, heart rate. The continuous data used by the analytics system may be obtained or derived from an exemplary physiological measurement system disclosed herein, or may be obtained or derived from a derived source or system, for example, a database of physiological data. In some embodiments, the analytics system computes, stores and displays one or more indicators or scores relating to the user's body, health and physical training including, but not limited to, an intensity score and a recovery score. The scores may be updated in real-time and continuously or at specific time periods, for example, the recovery score may be determined every morning upon waking up, the intensity score may be determined in real-time or after a workout routine or for an entire day.

In certain exemplary embodiments, a fitness score may be automatically determined based on the physiological data of two or more users of exemplary wearable systems.

An intensity score or indicator provides an accurate indication of the cardiovascular intensities experienced by the user during a portion of a day, during the entire day or during any desired period of time (e.g., during a week or month). The intensity score is customized and adapted for the unique physiological properties of the user and takes into account, for example, the user's age, gender, anaerobic threshold, resting heart rate, maximum heart rate, and the like. If determined for an exercise routine, the intensity score provides an indication of the cardiovascular intensities experienced by the user continuously throughout the routine. If determined for a period of including and beyond an exercise routine, the intensity score provides an indication of the cardiovascular intensities experienced by the user during the routine and also the activities the user performed after the routine (e.g., resting on the couch, active day of shopping) that may affect their recovery or exercise readiness.

Figure 7:
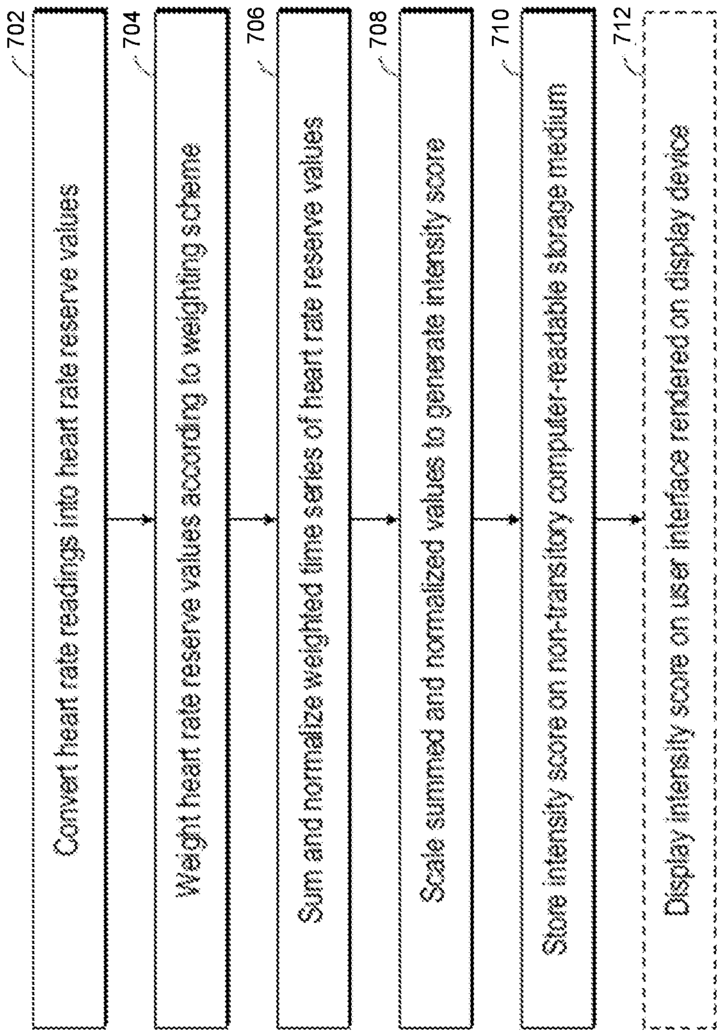
FIG. 7 is a flow chart illustrating a method of determining an intensity score.

In exemplary embodiments, the intensity score is calculated based on the user's heart rate reserve (HRR) as detected continuously throughout the desired time period, for example, throughout the entire day. In one embodiment, the intensity score is an integral sum of the weighted HRR detected continuously throughout the desired time period. FIG. 7 is a flow chart illustrating an exemplary method of determining an intensity score.

In step 702, continuous heart rate readings are converted to HRR values. A time series of heart rate data used in step 702 may be denoted as:

$$H \in T$$

A time series of HRR measurements, v(t), may be defined in the following expression in which MHR is the maximum heart rate and RHR is the resting heart rate of the user:

$$v(t) = \frac{H(t) - RHR}{MHR - RHR}$$

In step 704, the HRR values are weighted according to a suitable weighting scheme. Cardiovascular intensity, indicated by an intensity score, is defined in the following expression in which w is a weighting function of the HRR measurements:

$$I(t_o, t_1) = \int_{t_0}^{t_1} w(v(t))dt$$

In step 706, the weighted time series of HRR values is summed and normalized.

$$I_T = \int_T w(v(t))dt \leq w(1)|T|$$

Thus, the weighted sum is normalized to the unit interval, i.e., [0, 1]:

$$N_T = \frac{I_T}{w(1) \cdot 24 \text{ hr}}$$

In step 708, the summed and normalized values are scaled to generate user-friendly intensity score values. That is, the unit interval is transformed to have any desired distribution in a scale (e.g., a scale including 21 points from 0 to 21), for example, arctangent, sigmoid, sinusoidal, and the like. In certain distributions, the intensity values increase at a linear rate along the scale, and in others, at the highest ranges the intensity values increase at more than a linear rate to indicate that it is more difficult to climb in the scale toward the extreme end of the scale. In some embodiments, the raw intensity scores are scaled by fitting a curve to a selected group of "canonical" exercise routines that are predefined to have particular intensity scores.

In one embodiment, monotonic transformations of the unit interval are achieved to transform the raw HRR values to user-friendly intensity scores. An exemplary scaling scheme, expressed as f: [0, 1]→[0, 1], is performed using the following function:

$$(x, N, p) = 0.5\left(\frac{\arctan(N(x-p))}{\pi/2} + 1\right)$$

To generate an intensity score, the resulting value may be multiplied by a number based on the desired scale of the intensity score. For example, if the intensity score is graduated from zero to 21, then the value may be multiplied by 21.

In step 710, the intensity score values are stored on a non-transitory storage medium for retrieval, display and usage. In step 712, the intensity score values are, in some embodiments, displayed on a user interface rendered on a visual display device. The intensity score values may be displayed as numbers and/or with the aid of graphical tools, e.g., a graphical display of the scale of intensity scores with current score, and the like. In some embodiments, the intensity score may be indicated by audio. In step 712, the intensity score values are, in some embodiments, displayed along with one or more quantitative or qualitative pieces of information on the user including, but not limited to, whether the user has exceeded his/her anaerobic threshold, the heart rate zones experienced by the user during an exercise routine, how difficult an exercise routine was in the context of the user's training, the user's perceived exertion during an exercise routine, whether the exercise regimen of the user should be automatically adjusted (e.g., made easier if the intensity scores are consistently high), whether the user is likely to experience soreness the next day and the level of expected soreness, characteristics of the exercise routine (e.g., how difficult it was for the user, whether the exercise was in bursts or activity, whether the exercise was tapering, etc.), and the like. In one embodiment, the analytics system may automatically generate, store and display an exercise regimen customized based on the intensity scores of the user.

Step 706 may use any of a number of exemplary static or dynamic weighting schemes that enable the intensity score to be customized and adapted for the unique physiological properties of the user. In one exemplary static weighting scheme, the weights applied to the HRR values are based on static models of a physiological process. The human body employs different sources of energy with varying efficiencies and advantages at different HRR levels. For example, at the anaerobic threshold (AT), the body shifts to anaerobic respiration in which the cells produce two adenosine triphosphate (ATP) molecules per glucose molecule, as opposed to 36 at lower HRR levels. At even higher HRR levels, there is a further subsequent threshold (CPT) at which creatine triphosphate (CTP) is employed for respiration with even less efficiency.

In order to account for the differing levels of cardiovascular exertion and efficiency at the different HRR levels, in one embodiment, the possible values of HRR are divided into a plurality of categories, sections or levels (e.g., three) dependent on the efficiency of cellular respiration at the respective categories. The HRR parameter range may be divided in any suitable manner, such as, piecewise, including piecewise-linear, piecewise-exponential, and the like. An exemplary piecewise-linear division of the HRR parameter range enables weighting each category with strictly increasing values. This scheme captures an accurate indication of the cardiovascular intensity experienced by the user because it is more difficult to spend time at higher HRR values, which suggests that the weighting function should increase at the increasing weight categories.

In one non-limiting example, the HRR parameter range may be considered a range from zero (0) to one (1) and divided into categories with strictly increasing weights. In one example, the HRR parameter range may be divided into a first category of a zero HRR value and may assign this category a weight of zero; a second category of HRR values falling between zero (0) and the user's anaerobic threshold (AT) and may assign this category a weight of one (1); a third category of HRR values falling between the user's anaerobic threshold (AT) and a threshold at which the user's body employs creatine triphosphate for respiration (CPT) and may assign this category a weight of 18; and a fourth category of HRR values falling between the creatine triphosphate threshold (CPT) and one (1) and may assign this category a weight of 42, although other numbers of HRR categories and different weight values are possible. That is, in this example, the weights are defined as:

$$w(v) = \begin{cases} 0: & v = 0 \\ 1: & v \in (0, AT] \\ 18: & v \in (AT, CPT] \\ 42: & v \in (CPT, 1] \end{cases}$$

In another exemplary embodiment of the weighting scheme, the HRR time series is weighted iteratively based on the intensity scores determined thus far (e.g., the intensity score accrued thus far) and the path taken by the HRR values to get to the present intensity score. The path may be detected automatically based on the historical HRR values and may indicate, for example, whether the user is performing high intensity interval training (during which the intensity scores are rapidly rising and falling), whether the user is taking long breaks between bursts of exercise (during which the intensity scores are rising after longer periods), and the like. The path may be used to dynamically determine and adjust the weights applied to the HRR values. For example, in the case of high intensity interval training, the weights applied may be higher than in the case of a more traditional exercise routine.

In another exemplary embodiment of the weighting scheme, a predictive approach is used by modeling the weights or coefficients to be the coefficient estimates of a logistic regression model. In this scheme, a training data set is obtained by continuously detecting the heart rate time series and other personal parameters of a group of individuals. The training data set is used to train a machine learning system to predict the cardiovascular intensities experienced by the individuals based on the heart rate and other personal data. The trained system models a regression in which the coefficient estimates correspond to the weights or coefficients of the weighting scheme. In the training phase, user input on perceived exertion and the intensity scores are compared. The learning algorithm also alters the weights based on the improving or declining health of a user as well as their qualitative feedback. This yields a unique algorithm that incorporates physiology, qualitative feedback, and quantitative data. In determining a weighting scheme for a specific user, the trained machine learning system is run by executing computer-executable instructions encoded on one or more non-transitory computer-readable media, and generates the coefficient estimates which are then used to weight the user's HRR time series.

One of ordinary skill in the art will recognize that two or more aspects of any of the disclosed weighting schemes may be applied separately or in combination in an exemplary method for determining an intensity score.

In one aspect, heart rate zones quantify the intensity of workouts by weighing and comparing different levels of heart activity as percentages of maximum heart rate. Analysis of the amount of time an individual spends training at a certain percentage of his/her MHR may reveal his/her state of physical exertion during a workout. This intensity, developed from the heart rate zone analysis, motion, and activity, may then indicate his/her need for rest and recovery after the workout, e.g., to minimize delayed onset muscle soreness (DOMS) and prepare him/her for further activity. As discussed above, MHR, heart rate zones, time spent above the anaerobic threshold, and HRV in RSA (Respiratory Sinus Arrhythmia) regions—as well as personal information (gender, age, height, weight, etc.) may be utilized in data processing.

A recovery score or indicator provides an accurate indication of the level of recovery of a user's body and health after a period of physical exertion. The human autonomic nervous system controls the involuntary aspects of the body's physiology and is typically subdivided into two branches: parasympathetic (deactivating) and sympathetic (activating). Heart rate variability (HRV), i.e., the fluctuation in inter-heartbeat interval time, is a commonly studied result of the interplay between these two competing branches. Parasympathetic activation reflects inputs from internal organs, causing a decrease in heart rate. Sympathetic activation increases in response to stress, exercise and disease, causing an increase in heart rate. For example, when high intensity exercise takes place, the sympathetic response to the exercise persists long after the completion of the exercise. When high intensity exercise is followed by insufficient recovery, this imbalance typically lasts until the next morning, resulting in a low morning HRV. This result should be taken as a warning sign as it indicates that the parasympathetic system was suppressed throughout the night. While suppressed, normal repair and maintenance processes that ordinarily would occur during sleep were suppressed as well. Suppression of the normal repair and maintenance processes results in an unprepared state for the next day, making subsequent exercise attempts more challenging.

The recovery score is customized and adapted for the unique physiological properties of the user and takes into account, for example, the user's heart rate variability (HRV), resting heart rate, sleep quality and recent physiological strain (indicated, in one example, by the intensity score of the user). In one exemplary embodiment, the recovery score is a weighted combination of the user's heart rate variability (HRV), resting heart rate, sleep quality indicated by a sleep score, and recent strain (indicated, in one example, by the intensity score of the user). In an exemplar, the sleep score combined with performance readiness measures (such as, morning heart rate and morning heart rate variability) provides a complete overview of recovery to the user. By considering sleep and HRV alone or in combination, the user can understand how exercise-ready he/she is each day and to understand how he/she arrived at the exercise-readiness score each day, for example, whether a low exercise-readiness score is a predictor of poor recovery habits or an inappropriate training schedule. This insight aids the user in adjusting his/her daily activities, exercise regimen and sleeping schedule therefore obtaining the most out of his/her training.

In some cases, the recovery score may take into account perceived psychological strain experienced by the user. In some cases, perceived psychological strain may be detected from user input via, for example, a questionnaire on a mobile device or web application. In other cases, psychological strain may be determined automatically by detecting changes in sympathetic activation based on one or more parameters including, but not limited to, heart rate variability, heart rate, galvanic skin response, and the like.

With regard to the user's HRV used in determining the recovery score, suitable techniques for analyzing HRV include, but are not limited to, time-domain methods, frequency-domain methods, geometric methods and non-linear methods. In one embodiment, the HRV metric of the root-mean-square of successive differences (RMSSD) of RR intervals is used. The analytics system may consider the magnitude of the differences between 7-day moving averages and 3-day moving averages of these readings for a given day. Other embodiments may use Poincare Plot analysis or other suitable metrics of HRV.

The recovery score algorithm may take into account RHR along with history of past intensity and recovery scores.

With regard to the user's resting heart rate, moving averages of the resting heart rate are analyzed to determine significant deviations. Consideration of the moving averages is important since day-to-day physiological variation is quite large even in healthy individuals. Therefore, the analytics system may perform a smoothing operation to distinguish changes from normal fluctuations.

Although an inactive condition, sleep is a highly active recovery state during which a major portion of the physiological recovery process takes place. Nonetheless, a small, yet significant, amount of recovery can occur throughout the day by rehydration, macronutrient replacement, lactic acid removal, glycogen re-synthesis, growth hormone production and a limited amount of musculoskeletal repair. In assessing the user's sleep quality, the analytics system generates a sleep score using continuous data collected by an exemplary physiological measurement system regarding the user's heart rate, skin conductivity, ambient temperature and accelerometer/gyroscope data throughout the user's sleep. Collection and use of these four streams of data enable an understanding of sleep previously only accessible through invasive and disruptive over-night laboratory testing. For example, an increase in skin conductivity when ambient temperature is not increasing, the wearer's heart rate is low, and the accelerometer/gyroscope shows little motion, may indicate that the wearer has fallen asleep. The sleep score indicates and is a measure of sleep efficiency (how good the user's sleep was) and sleep duration (if the user had sufficient sleep). Each of these measures is determined by a combination of physiological parameters, personal habits and daily stress/strain (intensity) inputs. The actual data measuring the time spent in various stages of sleep may be combined with the wearer's recent daily history and a longer-term data set describing the wearer's personal habits to assess the level of sleep sufficiency achieved by the user. The sleep score is designed to model sleep quality in the context of sleep duration and history. It thus takes advantage of the continuous monitoring nature of the exemplary physiological measurement systems disclosed herein by considering each sleep period in the context of biologically-determined sleep needs, pattern-determined sleep needs and historically-determined sleep debt.

The recovery and sleep score values are stored on a non-transitory storage medium for retrieval, display and usage. The recovery and/or sleep score values are, in some embodiments, displayed on a user interface rendered on a visual display device. The recovery and/or sleep score values may be displayed as numbers and/or with the aid of graphical tools, e.g., a graphical display of the scale of recovery scores with current score, and the like. In some embodiments, the recovery and/or sleep score may be indicated by audio. The recovery score values are, in some embodiments, displayed along with one or more quantitative or qualitative pieces of information on the user including, but not limited to, whether the user has recovered sufficiently, what level of activity the user is prepared to perform, whether the user is prepared to perform an exercise routine a particular desired intensity, whether the user should rest and the duration of recommended rest, whether the exercise regimen of the user should be automatically adjusted (e.g., made easier if the recovery score is low), and the like. In one embodiment, the analytics system may automatically generate, store and display an exercise regimen customized based on the recovery scores of the user alone or in combination with the intensity scores.

As discussed above, the sleep performance metric may be based on parameters like the number of hours of sleep, sleep onset latency, and the number of sleep disturbances. In this manner, the score may compare a tactical athlete's duration and quality of sleep in relation to the tactical athlete's evolving sleep need (e.g., a number of hours based on recent strain, habitual sleep need, signs of sickness, and sleep debt). By way of example, a soldier may have a dynamically changing need for sleep, and it may be important to consider the total hours of sleep in relation to the amount of sleep that may have been required. By providing an accurate sensor for sleep and sleep performance, an aspect may evaluate sleep in the context of the overall day and lifestyle of a specific user.

Figure 8:
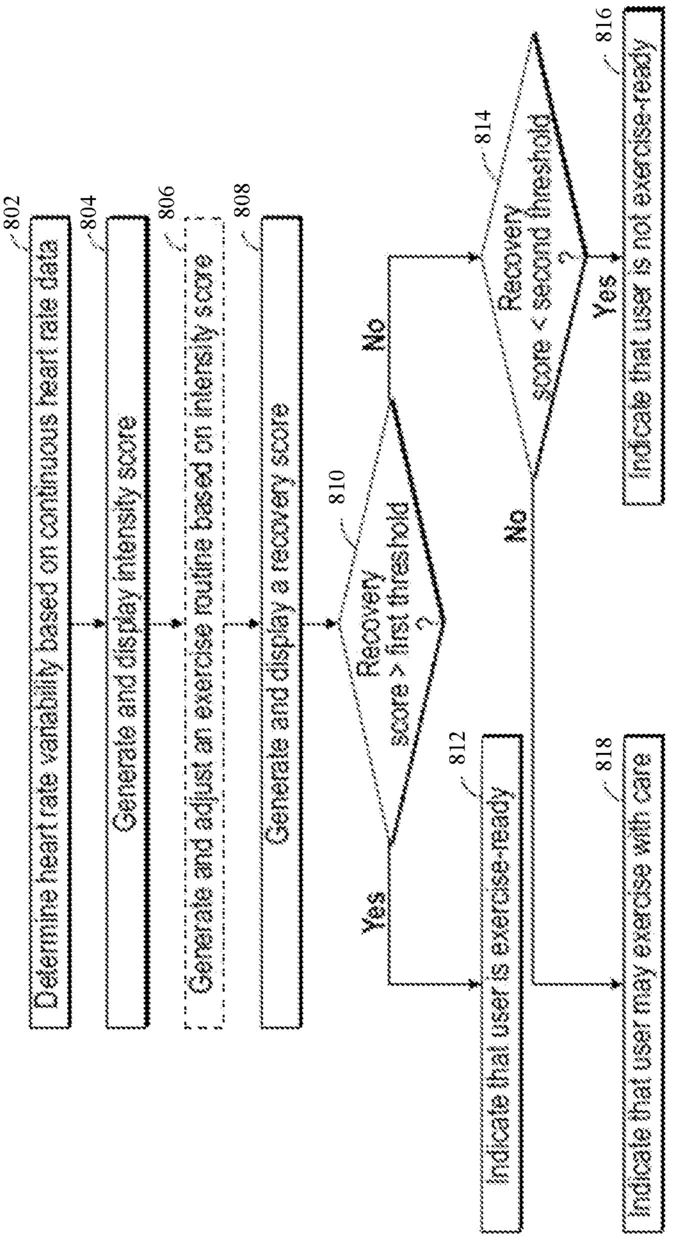
FIG. 8 is a flow chart illustrating a method by which a user may use intensity and recovery scores.
Figure 9:
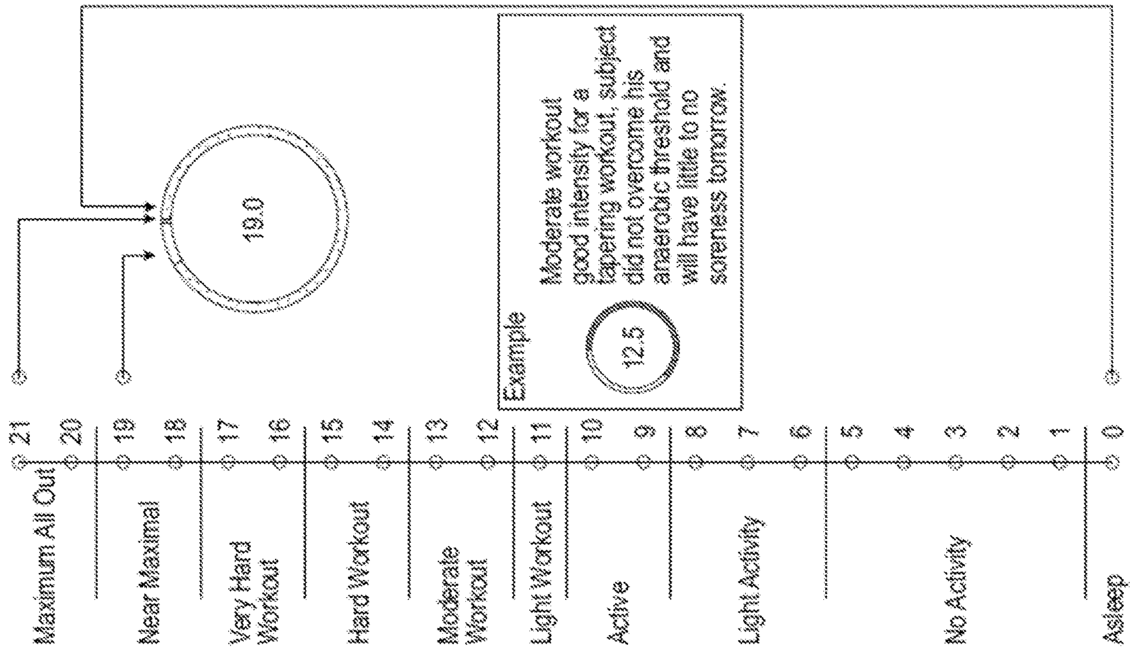
FIG. 9 illustrates a display of an intensity score index indicated in a circular graphic component with an exemplary current score of 19.0 indicated.

FIG. 8 is a flow chart illustrating an exemplary method by which a user may use intensity and recovery scores. In step 802, the wearable physiological measurement system begins determining heart rate variability (HRV) measurements based on continuous heart rate data collected by an exemplary physiological measurement system. In some cases, it may take the collection of several days of heart rate data to obtain an accurate baseline for the HRV. In step 804, the analytics system may generate and display intensity score for an entire day or an exercise routine. In some cases, the analytics system may display quantitative and/or qualitative information corresponding to the intensity score. FIG. 9 illustrates an exemplary display of an intensity score index indicated in a circular graphic component with an exemplary current score of 19.0 indicated. The graphic component may indicate a degree of difficulty of the exercise corresponding to the current score selected from, for example, maximum all out, near maximal, very hard, hard, moderate, light, active, light active, no activity, asleep, and the like. The display may indicate, for example, that the intensity score corresponds to a good and tapering exercise routine, that the user did not overcome his anaerobic threshold and that the user will have little to no soreness the next day.

In step 806, in an exemplary embodiment, the analytics system may automatically generate or adjust an exercise routine or regimen based on the user's actual intensity scores or desired intensity scores. For example, based on inputs of the user's actual intensity scores, a desired intensity score (that is higher than the actual intensity scores) and a first exercise routine currently performed by the user (e.g., walking), the analytics system may recommend a second different exercise routine that is typically associated with higher intensity scores than the first exercise routine (e.g., running).

In step 808, at any given time during the day (e.g., every morning), the analytics system may generate and display a recovery score. In some cases, the analytics system may display quantitative and/or qualitative information corresponding to the intensity score. For example, in step 810, in an exemplary embodiment, the analytics system may determine if the recovery is greater than (or equal to or greater than) a first predetermined threshold (e.g., about 60% to about 80% in some examples) that indicates that the user is recovered and is ready for exercise. If this is the case, in step 812, the analytics system may indicate that the user is ready to perform an exercise routine at a desired intensity or that the user is ready to perform an exercise routine more challenging than the past day's routine. Otherwise, in step 814, the analytics system may determine if the recovery is lower than (or equal to or lower than) a second predetermined threshold (e.g., about 10% to about 40% in some examples) that indicates that the user has not recovered. If this is the case, in step 816, the analytics system may indicate that the user should not exercise and should rest for an extended period. The analytics system may, in some cases, extend the duration of recommended rest. Otherwise, in step 818, the analytics system may indicate that the user may exercise according to his/her exercise regimen while being careful not to overexert him/herself. The thresholds may, in some cases, be adjusted based on a desired intensity at which the user desires to exercise. For example, the thresholds may be increased for higher planned intensity scores.

Figure 10:
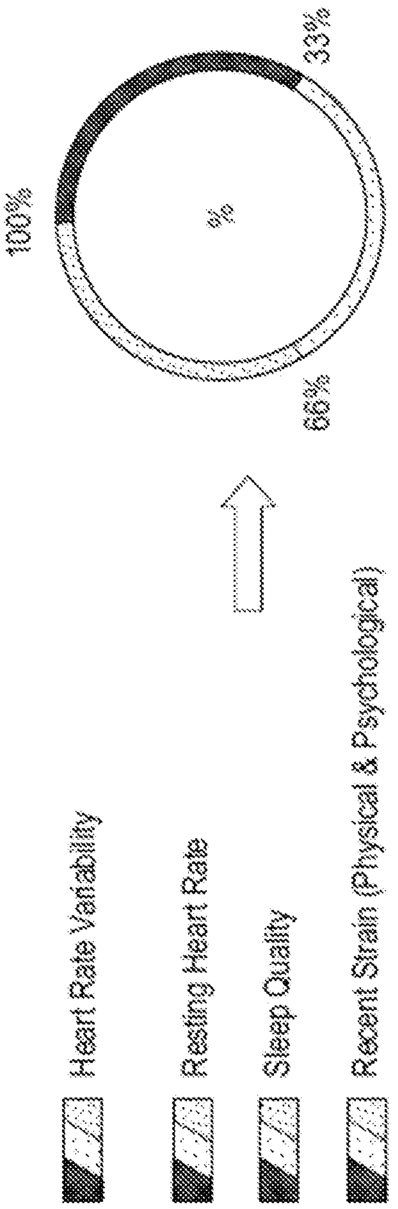
FIG. 10 illustrates a display of a recovery score index indicated in a circular graphic component with a first threshold of 66% and a second threshold of 33% indicated.
Figure 11A:
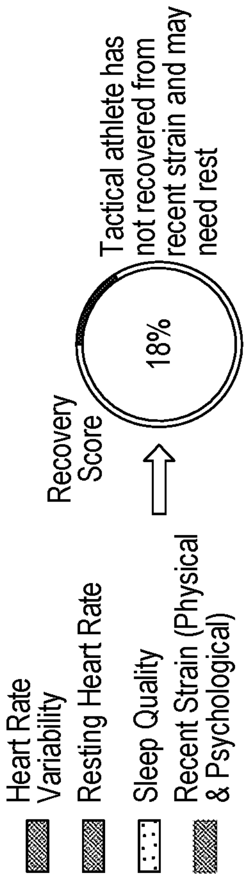
FIG. 11A illustrates a recovery score graphic component with a recovery score and qualitative information corresponding to the recovery score.
Figure 11B:
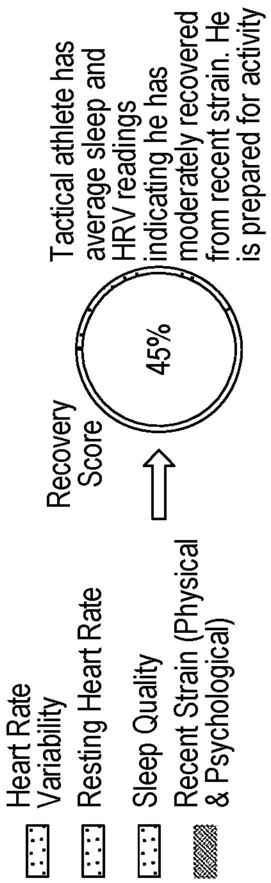
FIG. 11B illustrates a recovery score graphic component with a recovery score and qualitative information corresponding to the recovery score.
Figure 11C:
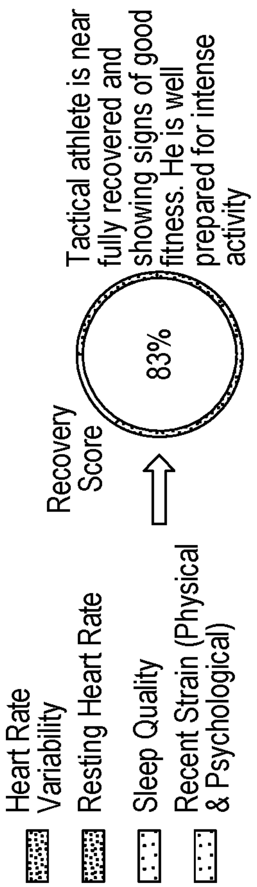
FIG. 11C illustrates a recovery score graphic component with a recovery score and qualitative information corresponding to the recovery score.
Figure 12A:
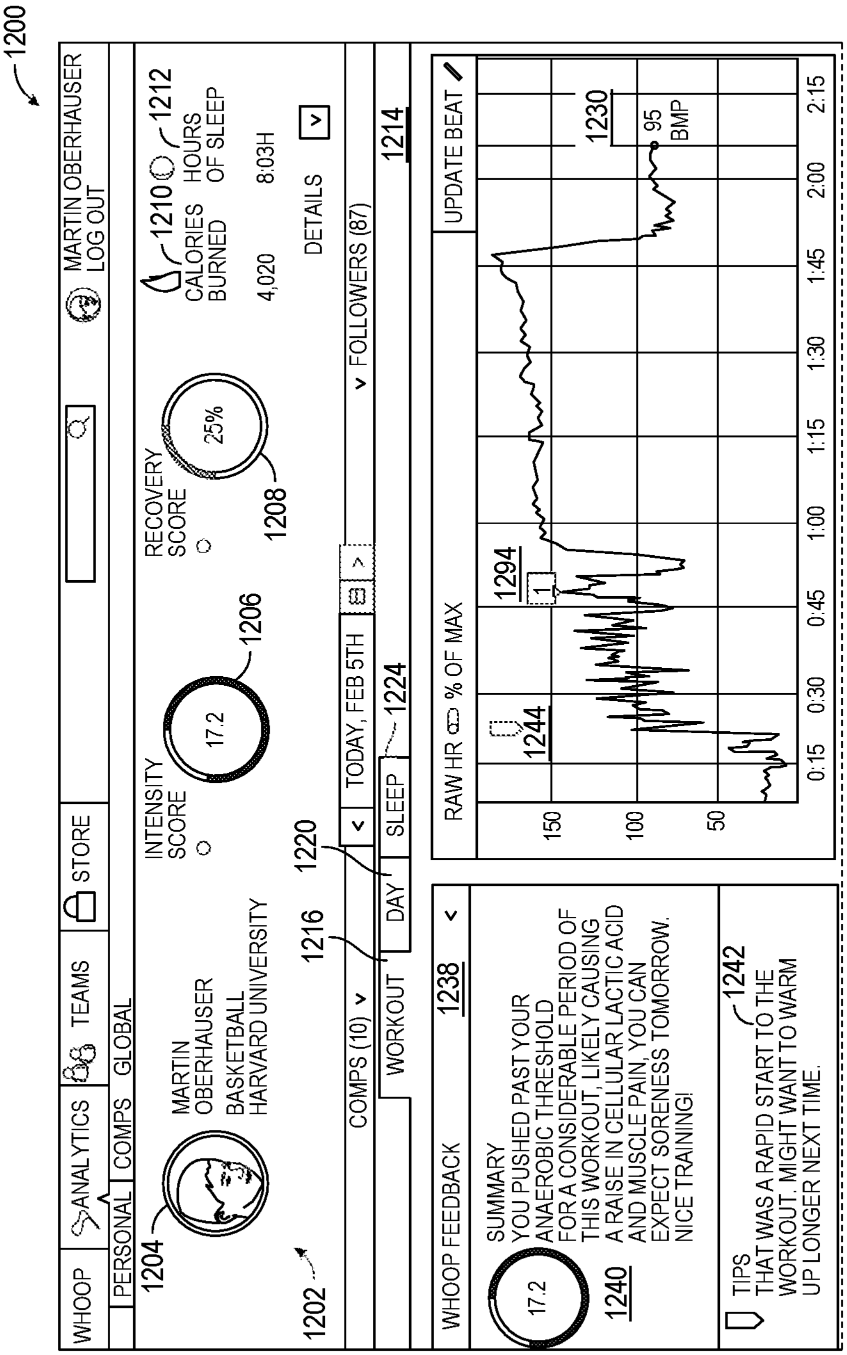
FIG. 12A illustrates part of a user interface for displaying physiological data specific to a user as rendered on visual display device.
Figure 12B:
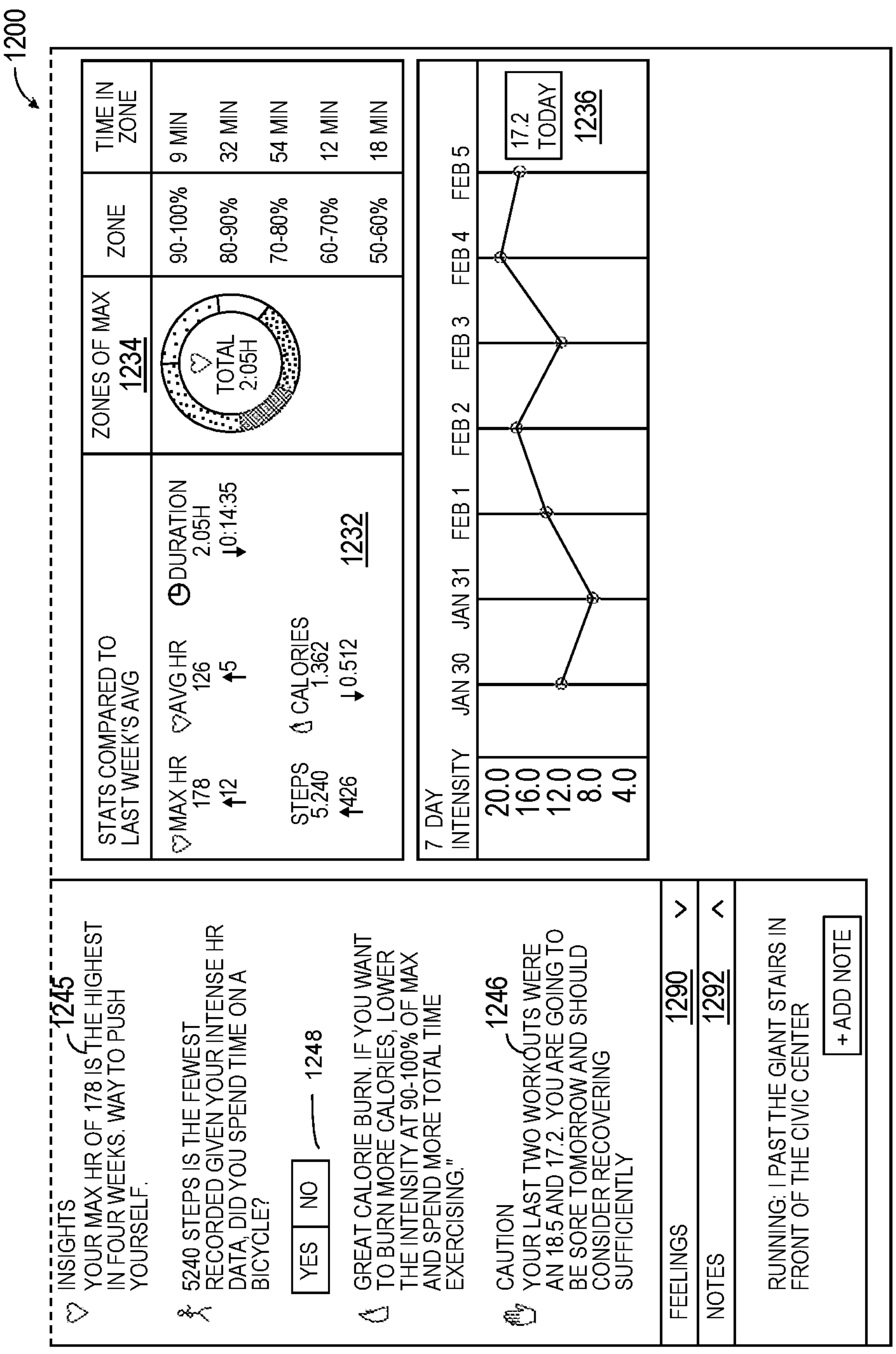
FIG. 12B illustrates part of a user interface for displaying physiological data specific to a user as rendered on visual display device.
Figure 13A:
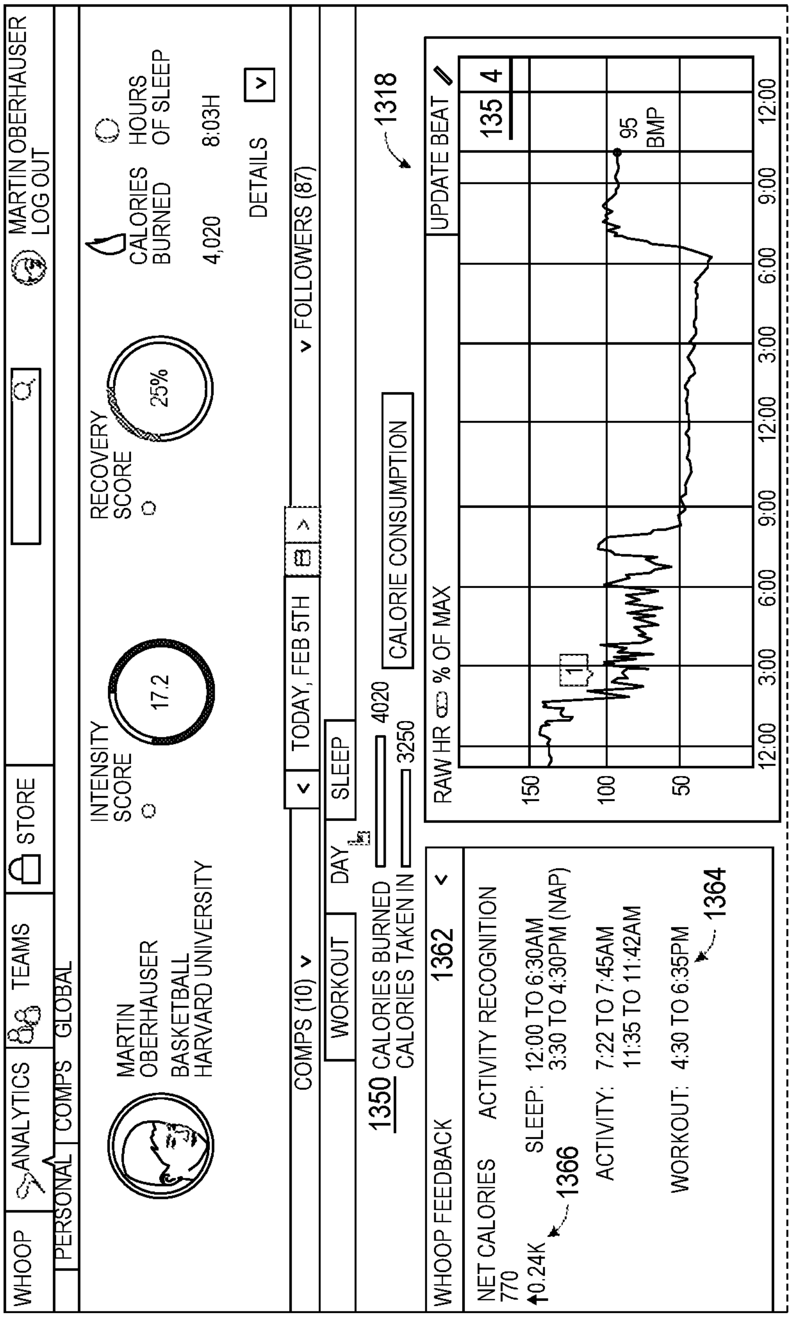
FIG. 13A illustrates part of a user interface for displaying physiological data specific to a user as rendered on visual display device.
Figure 13B:
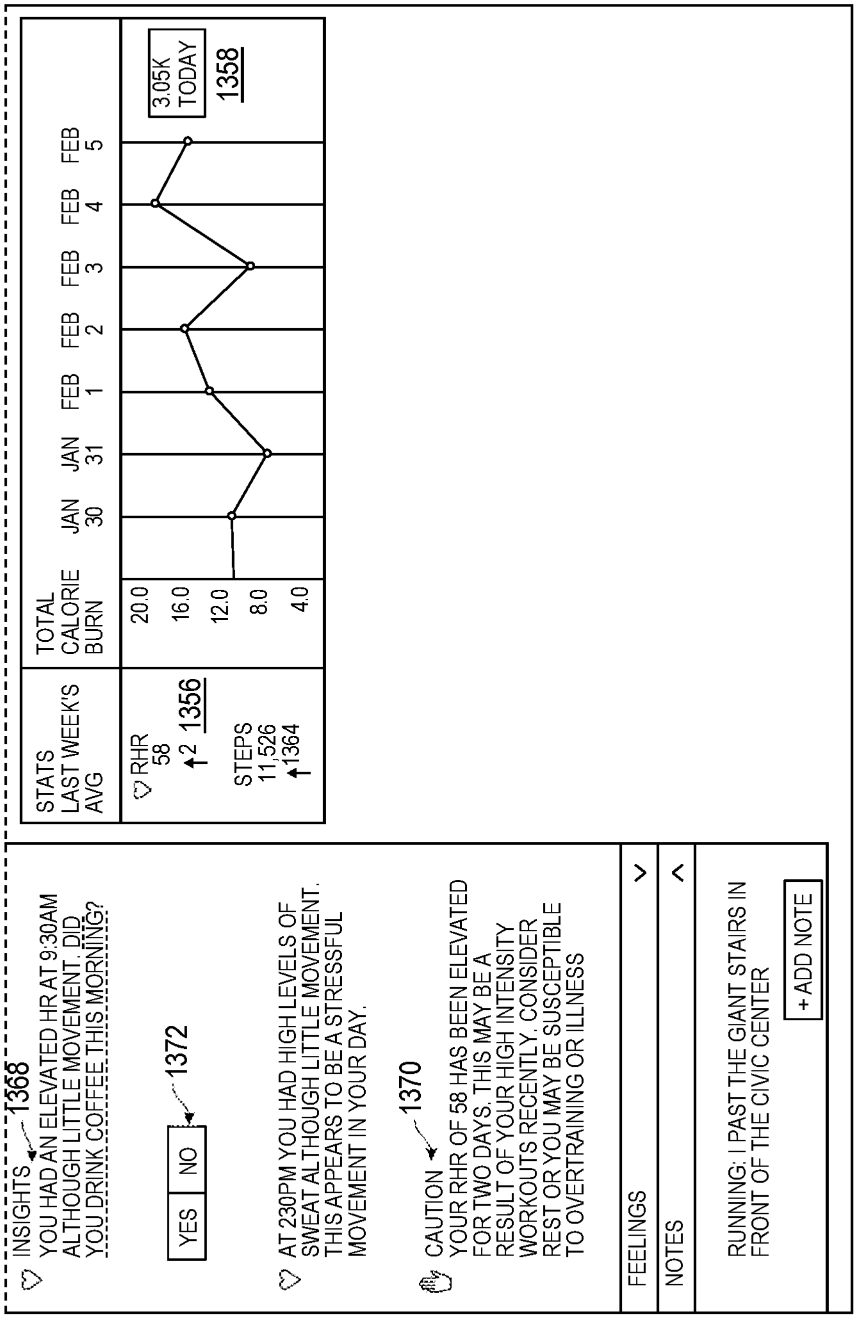
FIG. 13B illustrates part of a user interface for displaying physiological data specific to a user as rendered on visual display device.
Figure 14A:
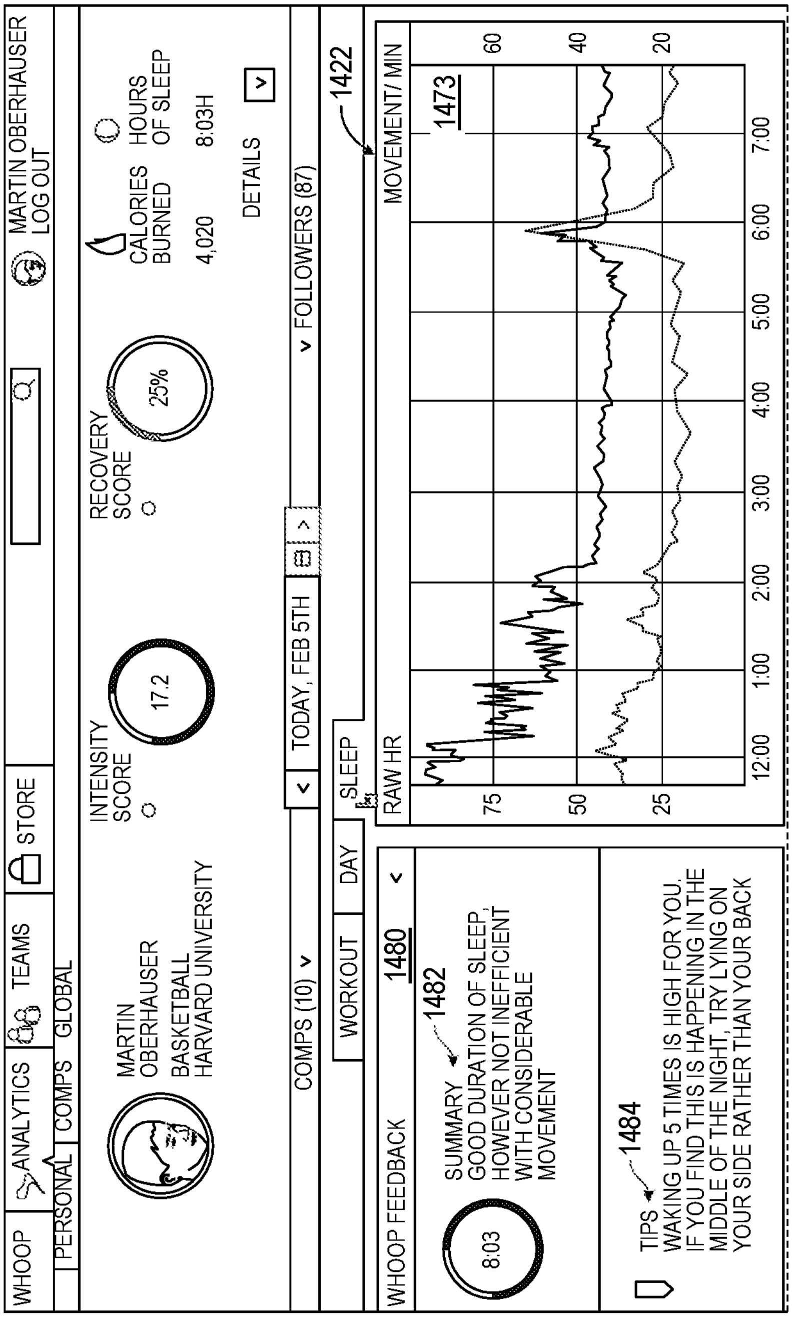
FIG. 14A illustrates part of a user interface for displaying physiological data specific to a user as rendered on visual display device.
Figure 14B:
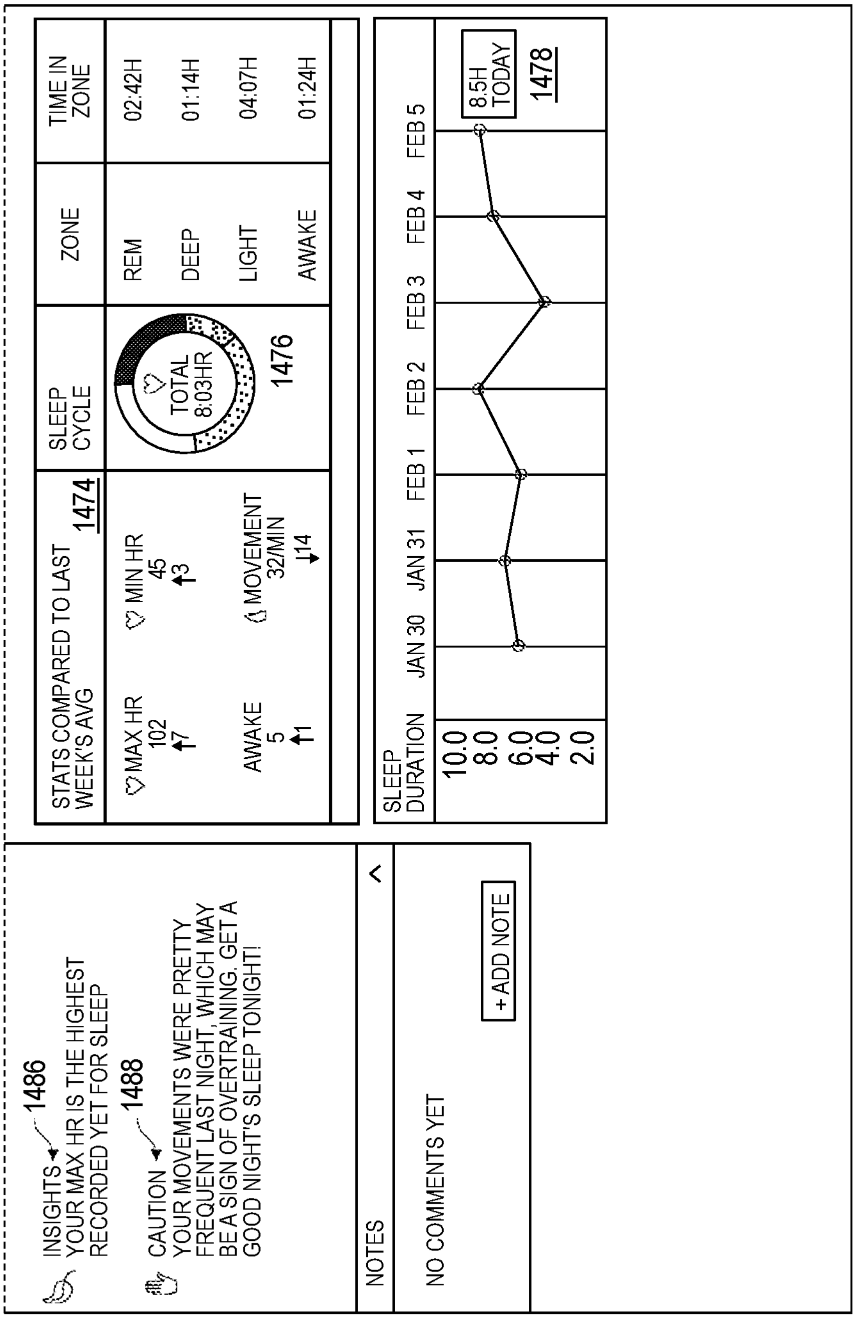
FIG. 14B illustrates part of a user interface for displaying physiological data specific to a user as rendered on visual display device.

FIG. 10 illustrates an exemplary display of a recovery score index indicated in a circular graphic component with a first threshold of 66% and a second threshold of 33% indicated. FIGS. 11A-11C illustrate the recovery score graphic component with exemplary recovery scores and qualitative information corresponding to the recovery scores.

Optionally, in an exemplary embodiment, the analytics system may automatically generate or adjust an exercise routine or regimen based on the user's actual recovery scores (e.g., to recommend lighter exercise for days during which the user has not recovered sufficiently). This process may also use a combination of the intensity and recovery scores.

The analytics system may, in some embodiments, determine and display the intensity and/or recovery scores of a plurality of users in a comparative manner. This enables users to match exercise routines with others based on comparisons among their intensity scores.

III. Exemplary Displays and User Interfaces

Exemplary embodiments also provide a vibrant and interactive online community for displaying and sharing physiological data among users. Exemplary systems have the ability to stream the physiological information wirelessly, directly or through a mobile device application, to an online website. The website allows users to monitor their own fitness results, share information with their teammates and coaches, compete with other users, and win status. Both the wearable system and the website allow a user to provide feedback regarding his day, which enables recovery and performance ratings. One aspect is directed to providing an online website for health and fitness monitoring. In some embodiments, the website may be a social networking site. The website may allow users, such as young athletes, to monitor their own fitness results, share information with their teammates and coaches, compete with other users, and win prizes. A user may include an individual whose health or fitness is being monitored, such as an individual wearing a bracelet disclosed herein, an athlete, a sports team member, a personal trainer or a coach. In some embodiments, a user may pick their own trainer from a list to comment on their performance.

In some embodiments, the website may be configured to provide an interactive user interface. The website may be configured to display results based on analysis of physiological data received from one or more devices. The website may be configured to provide competitive ways to compare one user to another, and ultimately a more interactive experience for the user. For example, in some embodiments, instead of merely comparing a user's physiological data and performance relative to that user's past performances, the user may be allowed to compete with other users and the user's performance may be compared to that of other users.

In some embodiments, the website may be a mobile website or a mobile application. In some embodiments, the website may be configured to communicate data to other websites or applications.

The exemplary website may include a brief and free sign-up process during which a user may create an account with his/her name, account name, email, home address, height, weight, age, and a unique code provided in his/her wearable physiological measurement system. The unique code may be provided, for example, on the wearable system itself or in the packaged kit. Once subscribed, continuous physiological data received from the user's system may be retrieved in a real-time continuous basis and presented automatically on a webpage associated with the user. Additionally, the user can add information to his profile, such as, a picture, favorite activities, sports team(s), and the user may search for teammates/friends on the website for sharing information.

FIGS. 12A-14B illustrate an exemplary user interface 1200 for displaying physiological data specific to a user as rendered on visual display device. The user interface 1200 may take the form of a webpage in some embodiments. One of ordinary skill in the art will recognize that the information in FIGS. 12A-14B represent non-limiting illustrative examples. The user interface 1200 may include a summary panel 1202 including an identification 1204 of the user (e.g., a real or account name) with, optionally, a picture or photo corresponding to the user. The summary panel 1202 may also display the current intensity score 1206 and the current recovery score 1208 of the user. In some embodiments, the summary panel 1202 may display the number of calories burned 1210 by the user that day and the number of hours of sleep 1212 obtained by the user the previous night.

The user interface 1200 may also include panels for presenting information on the user's workouts—a workout panel 1214 accessible using tab 1216, day—a day panel 1318 accessible using tab 1220, and sleep—a sleep panel 1422 accessible using tab 1224. The same or different feedback panels may be associated with the workout, day, and sleep panels. The panels may enable the user to select and customize one or more informative panels that appear in his/her user interface display.

The workout panel 1214 may present quantitative information on the user's health and exercise routines, for example, a graph 1230 of the user's continuous heart rate during the exercise, statistics 1232 on the maximum heart rate, average heart rate, duration of exercise, number of steps taken and calories expended, zones 1234 in which the maximum heart rate fell during the exercise, and a graph 1236 of the intensity scores over a period of time (e.g., seven days).

A feedback panel 1238 associated with the workout panel 1214 may present information on the intensity score and the exercise routines performed by the user during a selected period of time including, but not limited to, quantitative information, qualitative information, feedback, recommendations on future exercise routines, and the like. The feedback panel 1238 may present the intensity score along with a qualitative summary 1240 of the score indicating, for example, whether the user pushed past his anaerobic threshold for a considerable period of the exercise, whether the exercise is likely to cause muscle pain and soreness, and the like. Based on analysis of the quantitative health parameters monitored during the exercise routine, the feedback panel 1238 may present one or more tips 1242 on adjusting the exercise routine, for example, that the exercise routine started too rapidly and that the user should warm up for longer. In some cases, upon selection of the tips sub-panel 1242, a corresponding indicator 1244 may be provided in the heart rate graph 1230.

Based on analysis of the quantitative health parameters monitored during the exercise routine, the feedback panel 1238 may also present qualitative information 1245 on the user's exercise routine, for example, comparison of the present day's exercise routine to the user's historical exercise data. Such information may indicate, for example, that the user's maximum heart rate for the day's exercise was the highest ever recorded, that the steps taken by the user that day was the fewest ever recorded, that the user burned a lot of calories and that more calories may be burned by lowering the intensity of the exercise, and the like. The feedback panel 1238 may also present cautionary indicators 1246 to warn the user of future anticipated health events, for example, the likelihood of soreness (e.g., if the intensity score is higher than a predefined threshold), and the like.

An exemplary analytics system may analyze the information presented in the workout panel 1214 and determine whether the user performed a specific exercise routine or activity. As one example, given a small number of steps taken and a high calorie burn and heart rate, the system may determine that it is possible the user rode a bicycle that day. In some cases, the feedback panel 1238 may prompt the user to confirm whether he/she indeed performed that activity in a user field 1248. This user input may be displayed and/or used to improve an understanding of the user's health and exercise routines.

The day panel 1318 may include information on health parameters of the user during the current day including, but not limited to, the number of calories burned and the number of calories taken in 1350 (which may be based on user input on the foods eaten), a graph 1354 of the day's continuous heart rate, statistics 1356 on the resting heart rate and steps taken by the user that day, a graph 1358 of the calories burned that and other days, and the like.

In some cases, an analytics system may analyze the physiological data (e.g., heart rate data) and estimate the durations of sleep, activity and workout during the day. A feedback panel 1362 associated with the day panel 1318 may present these durations 1364. In some cases, the feedback panel 1362 may display a net number of calories consumed by the user that day 1366. Based on analysis of the quantitative health parameters monitored during the exercise routine, the feedback panel 1362 may also present qualitative information 1368 on the user's exercise routine. Such information may indicate, for example, that the user was stressed at a certain point in the day (e.g., if there was a high level of sweat with little activity), that the user's maximum heart rate for the day's exercise was the highest ever recorded, that the steps taken by the user that day was the fewest ever recorded, that the user burned a lot of calories and that more calories may be burned by lowering the intensity of the exercise, and the like. The feedback panel 1362 may also present cautionary indicators 1370 to warn the user of future anticipated health events, for example, tachycardia, susceptibility to illness or overtraining (e.g., if the resting heart rate is elevated for a few days), and the like.

An exemplary analytics system may analyze the information presented in the day panel 1318 and determine whether the user performed a specific exercise routine or activity. As one example, given an elevated heart rate with little activity, the system may determine that it is possible the user drank coffee at that point. In some cases, the feedback panel 1362 may prompt the user to confirm whether he/she indeed performed that activity in a user field 1372. This user input may be displayed and/or used to improve an understanding of the user's health and exercise routines.

The sleep panel 1422 may include information on health parameters of the user during sleep including, but not limited to, an overlaid graph 1473 of heart rate and movement during sleep, statistics 1474 on the maximum heart rate, minimum heart rate, number of times the user awoke during sleep, average movement during sleep, a sleep cycle indicator 1476 showing durations spent awake, in light sleep, in deep sleep and in REM sleep, and a sleep duration graph 1478 showing the number of hours slept over a period of time.

A feedback panel 1480 associated with the sleep panel 1422 may present information on the user's sleep including, but not limited to, quantitative information, qualitative information, feedback, recommendations on future exercise routines, and the like. The feedback panel 1480 may present a sleep score and/or a number of hours of sleep along with a qualitative summary of the score 1482 indicating, for example, whether the user slept enough, whether the sleep was efficient or inefficient, whether the user moved around and how much during sleep, and the like. Based on analysis of the quantitative health parameters monitored during sleep, the feedback panel 1480 may present one or more tips 1484 on adjusting sleep, for example, that the woke up a number of times during sleep and that user can try to sleep on his side rather than on his back.

Based on analysis of the quantitative health parameters monitored during the exercise routine, the feedback panel 1480 may also present qualitative information 1486 on the user's sleep. Such information may indicate, for example, that the user's maximum heart rate for the day's exercise was the highest ever recorded during sleep. The feedback panel 1480 may also present cautionary indicators 1488 to warn the user of future anticipated health events, for example, a sign of overtraining and a recommendation to get more sleep (e.g., if the user awoke many times during sleep and/or if the user moved around during sleep.

The user interface 1200 may provide a user input field 1290 for enabling the user to indicate his/her feelings, e.g., activities performed perceived exertion, energy level, performance. The user interface 1200 may also provide a user input field 1292 for enabling the user to indicate other facts about his exercise routine, e.g., comments on what the user was doing at a specific point in the exercise routine with a link 1294 to a corresponding point in the heart rate graph 1230. In some embodiments, the user may specify a route and/or location on a map at which the exercise routine was performed.

Exemplary embodiments also enable a user to compare his/her quantitative and/or qualitative physiological data with those of one or more additional users. A user may be presented with user selection components representing other users whose data is available for display. When a pointer is hovered over a user selection component (e.g., an icon representing a user), a snapshot of the user's information is presented in a popup component, and clicking on the user selection component opens up the full user interface displaying the user's information. In some cases, the user selection components include certain user-specific data surrounding an image representing the user, for example, a graphic element indicating the user's intensity score. The user selection components may be provided in a grid as shown or in a linear listing for easier sorting. The users appearing in the user selection components may be sorted and/or ranked based on any desired criteria, e.g., intensity scores, who is experiencing soreness, and the like. A user may leave comments on other users' pages.

Similarly, a user may select privacy settings to indicate which aspects of his/her own data may be viewed by other users. Because the wearable systems described herein support truly continuous monitoring, a user may wish to carefully control whether and when data is transmitted wirelessly, stored in a remote data repository, and shared with others. A privacy switch as described herein may be usefully employed to toggle between various privacy settings or to explicitly select private or restricted times when no monitoring should occur.

Figure 15:
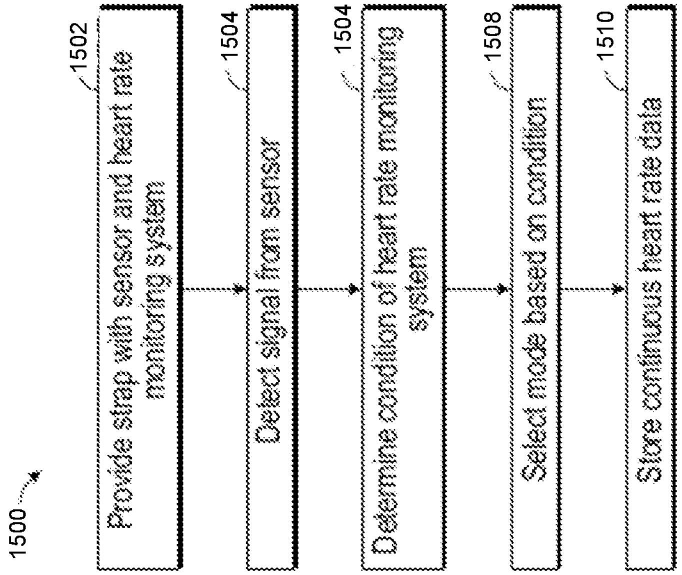
FIG. 15 is a flow chart illustrating a method for selecting modes of acquiring heart rate data.

FIG. 15 is a flow chart illustrating a method for selecting modes of acquiring heart rate data.

As shown in step 1502, the method 1500 may include providing a strap with a sensor and a heart rate monitoring system. The strap may be shaped and sized to fit about an appendage. For example, the strap may be any of the straps described herein, including, without limitation, a bracelet. The heart rate monitoring system may be configured to provide two or more different modes for detecting a heart rate of a wearer of the strap. The modes may include the use of optical detectors (e.g., light detectors), light emitters, motion sensors, a processing module, algorithms, other sensors, a peak detection technique, a frequency domain technique, variable optical characteristics, non-optical techniques, and so on.

As shown in step 1504, the method 1500 may include detecting a signal from the sensor. The signal may be detected by one or more sensors, which may include any of the sensors described herein. The signal may include, without limitation, one or more signals associated with the heart rate of the user, other physiological signals, an optical signal, signals based on movement, signals based on environmental factors, status signals (e.g., battery life), historical information, and so on.

As shown in step 1506, the method 1500 may include determining a condition of the heart rate monitoring system, which may be based upon the signal. The condition may include, without limitation, an accuracy of heart rate detection determined using a statistical analysis to provide a confidence level in the accuracy, a power consumption, a battery charge level, a user activity, a location of the sensor or motion of the sensor, an environmental or contextual condition (e.g., ambient light conditions), a physiological condition, an active condition, an inactive condition, and so on. This may include detecting a change in the condition, responsively selecting a different one of the two or more different modes, and storing additional continuous heart rate data obtained using at least one of the two or more different modes.

As shown in step 1508, the method 1500 may include selecting one of the two or more different modes for detecting the heart rate based on the condition. For example, based on the motion status of the user, the method may automatically and selectively activate one or more light emitters to determine a heart rate of the user. The system may also or instead determine the type of sensor to use at a given time based on the level of motion, skin temperature, heart rate, and the like. Based on a combination of these factors the system may selectively choose which type of sensor to use in monitoring the heart rate of the user. A processor or the like may be configured to select one of the modes. For example, if the condition is the accuracy of heart rate detection determined using a statistical analysis to provide a confidence level in the accuracy, the processor may be configured to select a different one of the modes when the confidence level is below a predetermined threshold.

As shown in step 1510, the method 1500 may include storing continuous heart rate data using one of the two or more different modes. This may include communicating the continuous heart rate data from the strap to a remote data repository. This may also or instead include storing the data locally, e.g., on a memory included on the strap. The memory may be removable, e.g., via a data card or the like, or the memory may be permanently attached/integral with the strap or a component thereof. The stored data (e.g., heart rate data) may be for the user's private use, for example, when in a private setting, or the data may be shared when in a shared setting (e.g., on a social networking site or the like). The method 1500 may further include the use of a privacy switch operable by the user to controllably restrict communication of a portion of the data, e.g., to the remote data repository.

Figure 16:
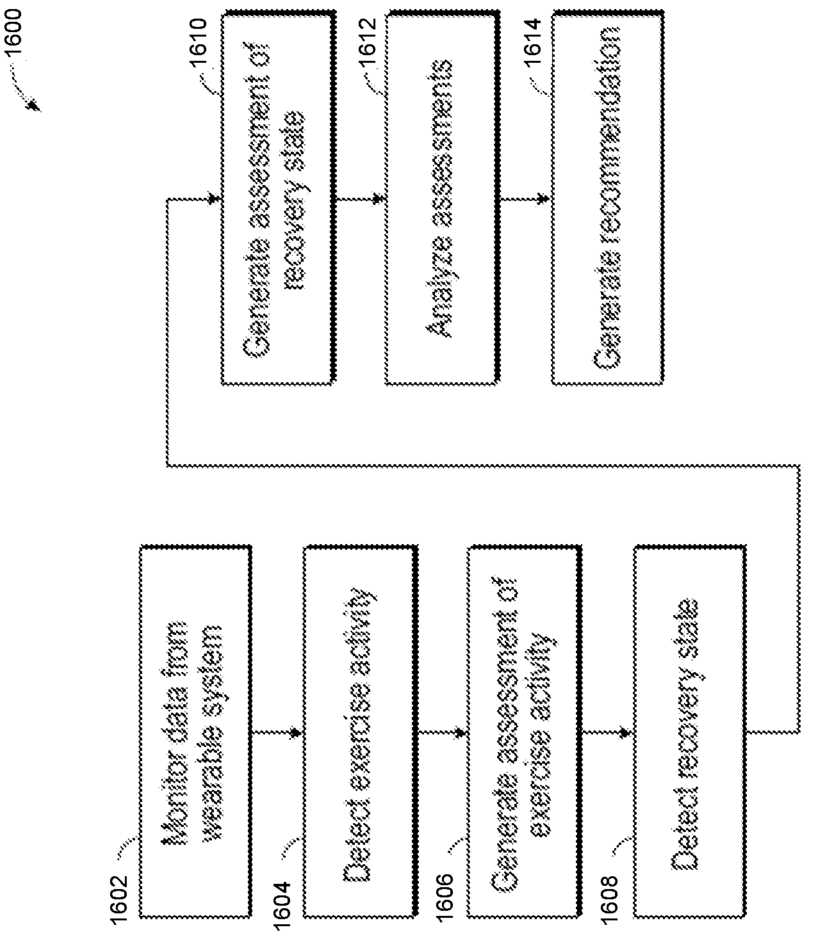
FIG. 16 is a flow chart of a method for assessing recovery and making exercise recommendations.

FIG. 16 is a flow chart of a method for assessing recovery and making exercise recommendations.

As shown in step 1602, the method 1600 may include monitoring data from a wearable system. The wearable system may be a continuous-monitoring, physiological measurement system worn by a user. The data may include heart rate data, other physiological data, summary data, motion data, fitness data, activity data, or any other data described herein or otherwise contemplated by a skilled artisan.

As shown in step 1604, the method 1600 may include detecting exercise activity. This may include automatically detecting exercise activity of the user. The exercise activity may be detected through the use of one or more sensors as described herein. The exercise activity may be sent to a server that, e.g., performs step 1606 described below.

As shown in step 1606, the method 1600 may include generating an assessment of the exercise activity. This may include generating a quantitative assessment of the exercise activity. Generating a quantitative assessment of the exercise activity may include analyzing the exercise activity on a remote server. Generating a quantitative assessment may include the use of the algorithms discussed herein. The method 1600 may also include generating periodic updates to the user concerning the exercise activity. The method 1600 may also include determining a qualitative assessment of the exercise activity and communicating the qualitative assessment to the user.

As shown in step 1608, the method 1600 may include detecting a recovery state. This may include automatically detecting a physical recovery state of the user. The recovery state may be detected through the use of one or more sensors as described herein. The recovery state may be sent to a server that, e.g., performs step 1610 described below.

As shown in step 1610, the method 1600 may include generating an assessment of the recovery state. This may include generating a quantitative assessment of the physical recovery state. Generating a quantitative assessment may include the use of the algorithms discussed herein. Generating a quantitative assessment of the physical recovery state may include analyzing the physical recovery state on a remote server. The method 1600 may also include generating periodic updates to the user concerning the physical recover state. The method 1600 may also include determining a qualitative assessment of the recovery state and communicating the qualitative assessment to the user.

As shown in step 1612, the method 1600 may include analyzing the assessments, i.e., analyzing the quantitative assessment of the exercise activity and the quantitative assessment of the physical recovery. The analysis may include the use of one or more of the algorithms described herein, a statistical analysis, and so on. The analysis may include the use of a remote server.

As shown in step 1614, the method 1600 may include generating a recommendation. This may include automatically generating a recommendation on a change to an exercise routine of the user based on the analysis performed in step 1612. This may also or instead include determining a qualitative assessment of the exercise activity and/or recovery state, and communicating the qualitative assessment(s) to the user. The recommendation may be generated on a remote server. The recommendation may be communicated to the user in an electronic mail, it may be presented to the user in a web page, other communications interface, or the like. Generating the recommendation may be based upon a number of cycles of exercise and rest.

The method 1600 described above, or any of the methods discussed herein, may also or instead be implemented on a computer program product including non-transitory computer executable code embodied in a non-transitory computer-readable medium that executes on one or more computing devices to perform the method steps. For example, code may be provided that performs the various steps of the methods described herein.

Figure 17:
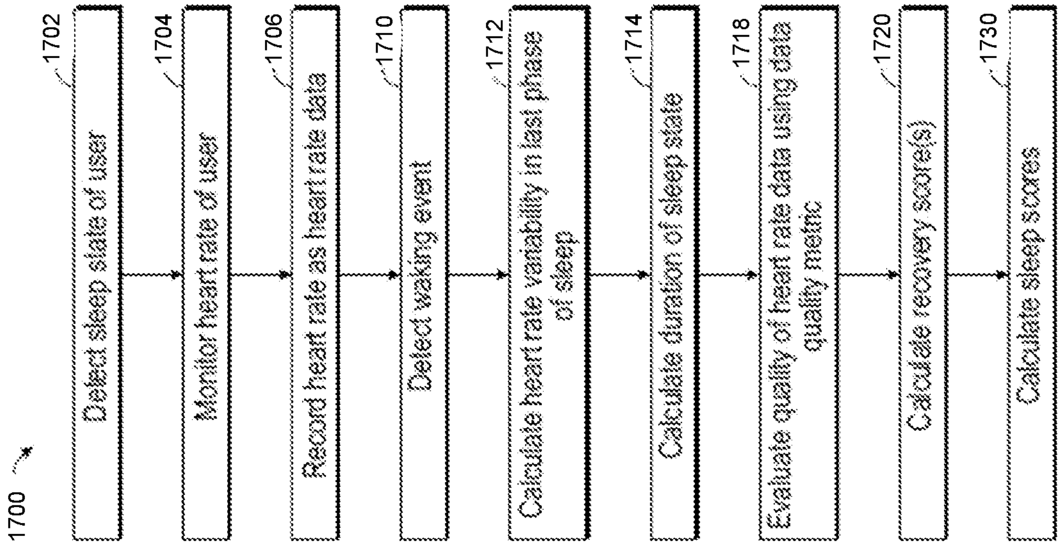
FIG. 17 is a flow chart illustrating a method for detecting heart rate variability in sleep states.

FIG. 17 is a flow chart illustrating a method for detecting heart rate variability in sleep states. The method 1700 may be used in cooperation with any of the devices, systems, and methods described herein, such as by operating a wearable, continuous physiological monitoring device to perform the following steps. The wearable, continuous physiological monitoring system may for example include a processor, one or more light emitting diodes, one or more light detectors configured to obtain heart rate data from a user, and one or more other sensors to assist in detecting stages of sleep. In general, the method 1700 aims to measure heart rate variability in the last phase of sleep before waking in order to provide a consistent and accurate basis for calculating a physical recovery score.

As shown in step 1702, the method 1700 may include detecting a sleep state of a user. This may, for example, include any form of continuous or periodic monitoring of sleep states using any of a variety of sensors or algorithms as generally described herein.

Sleep states (also be referred to as "sleep phases," "sleep cycles," "sleep stages," or the like) may include rapid eye movement (REM) sleep, non-REM sleep, or any states/stages included therein. The sleep states may include different phases of non-REM sleep, including Stages 1-3. Stage 1 of non-REM sleep generally includes a state where a person's eyes are closed, but the person can be easily awakened; Stage 2 of non-REM sleep generally includes a state where a person is in light sleep, i.e., where the person's heart rate slows and their body temperature drops in preparation for deeper sleep; and Stage 3 of non-REM sleep generally includes a state of deep sleep, where a person is not easily awakened. Stage 3 is often referred to as delta sleep, deep sleep, or slow wave sleep (i.e., from the high amplitude but small frequency brain waves typically found in this stage). Slow wave sleep is thought to be the most restful form of sleep, which relieves subjective feelings of sleepiness and restores the body.

REM sleep on the other hand typically occurs 1-2 hours after falling asleep. REM sleep may include different periods, stages, or phases, all of which may be included within the sleep states that are detected as described herein. During REM sleep, breathing may become more rapid, irregular and shallow, eyes may jerk rapidly (thus the term "Rapid Eye Movement" or "REM"), and limb muscles may be temporarily paralyzed. Brain waves during this stage typically increase to levels experienced when a person is awake. Also, heart rate, cardiac pressure, cardiac output, and arterial pressure may become irregular when the body moves into REM sleep. This is the sleep state in which most dreams occur, and, if awoken during REM sleep, a person can typically remember the dreams. Most people experience three to five intervals of REM sleep each night.

Homeostasis is the balance between sleeping and waking, and having proper homeostasis may be beneficial to a person's health. Lack of sleep is commonly referred to as sleep deprivation, which tends to cause slower brain waves, a shorter attention span, heightened anxiety, impaired memory, mood disorders, and general mental, emotional, and physical fatigue. Sleep debt (the effect of not getting enough sleep) may result in the diminished abilities to perform high-level cognitive functions. A person's circadian rhythms (i.e., biological processes that display an endogenous, entrainable oscillation of about 24 hours) may be a factor in a person's optimal amount of sleep. Thus, sleep may in general be usefully monitored as a proxy for physical recovery. However, a person's heart rate variability at a particular moment during sleep—during the last phase of sleep preceding a waking event—can further provide an accurate and consistent basis for objectively calculating a recovery score following a period of sleep.

According to the foregoing, sleep of a user may be monitored to detect various sleep states, transitions, and other sleep-related information. For example, the device may monitor/detect the duration of sleep states, the transitions between sleep states, the number of sleep cycles or particular states, the number of transitions, the number of waking events, the transitions to an awake state, and so forth. Sleep states may be monitored and detected using a variety of strategies and sensor configurations according to the underlying physiological phenomena. For example, body temperature may be usefully correlated to various sleep states and transitions. Similarly, galvanic skin response may be correlated to sweating activity and various sleep states, any of which may also be monitored, e.g., with a galvanic skin response sensor, to determine sleep states. Physical motion can also be easily monitored using accelerometers or the like, which can be used to detect waking or other activity involving physical motion. In another aspect, heart rate activity itself may be used to infer various sleep states and transitions, either alone or in combination with other sensor data. Other sensors may also or instead be used to monitor sleep activity, such as brain wave monitors, pupil monitors, and so forth, although the ability to incorporate these types of detection into a continuously wearable physiological monitoring device may be somewhat limited depending on the contemplated configuration.

As shown in step 1704, the method 1700 may include monitoring a heart rate of the user substantially continuously with the continuous physiological monitoring system. Continuous heart rate monitoring is described above in significant detail, and the description is not repeated here except to note generally that this may include raw sensor data, heart rate data or peak data, and heart rate variability data over some historical period that can be subsequently correlated to various sleep states and activities.

As shown in step 1706, the method 1700 may include recording the heart rate as heart rate data. This may include storing the heart rate data in any raw or processed form on the device, or transmitting the data to a local or remote location for storage. In one aspect, the data may be stored as peak-to-peak data or in some other semi-processed form without calculating heart rate variability. This may be useful as a technique for conserving processing resources in a variety of contexts, for example where only the heart rate variability at a particular time is of interest. Data may be logged in some unprocessed or semi-processed form, and then the heart rate variability at a particular point in time can be calculated once the relevant point in time has been identified.

As shown in step 1710, the method 1700 may include detecting a waking event at a transition from the sleep state of the user to an awake state. It should be appreciated that the waking event may be a result of a natural termination of sleep, e.g., after a full night's rest, or in response to an external stimulus that causes awakening prior to completion of a natural sleep cycle. Regardless of the precipitating event(s), the waking event may be detected via the various physiological changes described above, or using any other suitable techniques. While the emphasis herein is on a wearable, continuous monitoring device, it will be understood that the device may also receive inputs from an external device such as a camera (for motion detection) or an infrared camera (for body temperature detection) that can be used to aid in accurately assessing various sleep states and transitions.

Thus the wearable, continuous physiological monitoring system may generally detect a waking event using one or more sensors including, for example, one or more of an accelerometer, a galvanic skin response sensor, a light sensor, and so forth. For example, in one aspect, the waking event may be detected using a combination of motion data and heart rate data.

As shown in step 1712, the method 1700 may include calculating a heart rate variability of the user at a moment in a last phase of sleep preceding the waking event based upon the heart rate data. While a waking event and a history of sleep states are helpful information for assessing recovery, the method 1700 described herein specifically contemplates use of the heart rate variability in a last phase of sleep as a consistent foundation for calculating recovery scores for a device user. Thus step 1712 may also include detecting a slow wave sleep period immediately prior to the waking event, or otherwise determining the end of a slow wave or deep sleep episode immediately preceding the waking event.

It will be appreciated that the last phase of sleep preceding a natural waking event may be slow wave sleep. However, where a sleeper is awakened prematurely, this may instead include a last recorded episode of REM sleep or some other phase of sleep immediately preceding the waking event. This moment—the end of the last phase of sleep before waking—is the point at which heart rate variability data provides the most accurate and consistent indicator of physical recovery. Thus, with the appropriate point of time identified, the historical heart rate data (in whatever form) may be used with the techniques described above to calculate the corresponding heart rate variability. It will be further noted that the time period for this calculation may be selected with varying degrees of granularity depending on the ability to accurately detect the last phase of sleep and an end of the last phase of sleep. Thus for example, the time may be a predetermined amount of time before waking, or at the end of slow wave sleep, or some predetermined amount of time before the end of slow wave sleep is either detected or inferred. In another aspect, an average heart rate variability or similar metric may be determined for any number of discrete measurements within a window around the time of interest.

As shown in step 1714, the method 1700 may include calculating the duration of the sleep state. The quantity and quality of sleep may be highly relevant to physical recovery, and as such the duration of the sleep state may be used to calculate a recovery score.

As shown in step 1718, the method 1700 may include evaluating a quality of heart rate data using a data quality metric for a slow wave sleep period, e.g., the slow wave sleep period occurring most recently before the waking event. As noted above, the quality of heart rate measurements may vary over time for a variety of reasons. Thus the quality of heart rate data may be evaluated prior to selecting a particular moment or window of heart rate data for calculating heart rate variability, and the method 1700 may include using this quality data to select suitable values for calculating a recovery score. For example, the method 1700 may include calculating the heart rate variability for a window of predetermined duration within the slow wave sleep period having the highest quality of heart rate data according to the data quality metric.

As shown in step 1720, the method 1700 may include calculating a recovery score for the user based upon the heart rate variability from the last phase of sleep. The calculation may be based on other sources of data. For example, the calculation of recovery score may be based on the duration of sleep, the stages of sleep detected or information concerning the stages (e.g., amount of time in certain stages), information regarding the most recent slow wave sleep period or another sleep period/state, information from the GSR sensor or other sensor(s), and so on. The method 1700 may further include calculating additional recovery scores after one or more other waking events of the user for comparison to the previously calculated recovery score. The actual calculation of a discovery score is described in substantial detail above, and this description is not repeated here except to note that the use of a heart rate variability measurement from the last phase of sleep provides an accurate and consistent basis for evaluating the physical recovery state of a user following a period of sleep.

As shown in step 1730, the method 1700 may include calculating a sleep score and communicating this score to a user.

In one aspect, the sleep score may be a measure of prior sleep performance. For example, a sleep performance score may quantify, on a scale of 0-100, the ratio of the hours of sleep during a particular resting period compared to the sleep needed. On this scale, if a user sleeps six hours and needed eight hours of sleep, then the sleep performance may be calculated as 75%. The sleep performance score may begin with one or more assumptions about needed sleep, based on, e.g., age, gender, health, fitness level, habits, genetics, and so forth and may be adapted to actual sleep patterns measured for an individual over time.

The sleep score may also or instead include a sleep need score or other objective metric that estimates an amount of sleep needed by the user of the device in a next sleep period. In general, the score may be any suitable quantitative representation including, e.g., a numerical value over some predetermined scale (e.g., 0-10, 1-100, or any other suitable scale) or a representation of a number of hours of sleep that should be targeted by the user. In another aspect, the sleep score may be calculated as the number of additional hours of sleep needed beyond a normal amount of sleep for the user.

The score may be calculated using any suitable inputs that capture, e.g., a current sleep deficit, a measure of strain or exercise intensity over some predetermined prior interval, an accounting for any naps or other resting, and so forth. A variety of factors may affect the actual sleep need, including physiological attributes such as age, gender, health, genetics and so forth, as well as daytime activities, stress, napping, sleep deficit or deprivation, and so forth. The sleep deficit may itself be based on prior sleep need and actual sleep performance (quality, duration, waking intervals, etc.) over some historical window. In one aspect, an objective scoring function for sleep need may have a model of the form:

$$\text{SleepNeed}=\text{Baseline}+f_1 i(\text{strain})+f_2(\text{debt})-\text{Naps}$$

In general, this calculation aims to estimate the ideal amount of sleep for the best rest and recovery during a next sleep period. When accounting for time falling asleep, periods of brief wakefulness, and so forth, the actual time that should be dedicated to sleep may be somewhat higher, and this may be explicitly incorporated into the sleep need calculation, or left for a user to appropriately manage sleep habits.

In general, the baseline sleep may represent a standard amount of sleep needed by the user on a typical rest day (e.g., with no strenuous exercise or workout). As noted above, this may depend on a variety of factors, and may be estimated or measured for a particular individual in any suitable manner. The strain component, $f_1$(strain), may be assessed based on a previous day's physical intensity, and will typically increase the sleep need. Where intensity or strain is measured on an objective scale from 0 to 21, the strain calculation may take the following form, which yields an additional sleep time needed in minutes for a strain, i:

$$f(i)=\frac{1.7}{1+e^{\frac{17-i}{3.5}}}$$

The sleep debt, $f_2$(debt), may generally measure a carry-over of needed sleep that was not attained in a previous day. This may be scaled, and may be capped at a maximum, according to individual sleep characteristics or general information about long term sleep deficit and recovery. Naps may also be accounted for directly by correcting the sleep need for any naps that have been taken, or by calculating a nap factor that is scaled or otherwise manipulated or calculated to more accurately track the actual effect of naps on prospective sleep need.

However calculated, the sleep need may be communicated to a user, such as by displaying a sleep need on a wrist-worn physiological monitoring device, or by sending an e-mail, text message or other alert to the user for display on any suitable device.

Described herein are physiological monitoring devices, systems, and methods for detecting and analyzing periods in which a user is asleep or resting. However, the actual sleep achieved during sleep opportunities (that is, the time dedicated to sleep) is typically only about 90%-95% of the total available timewise opportunity. The remaining 5%-10% of a sleep opportunity may be lost to brief sleep disruptions lasting anywhere from a few seconds to a few minutes. This presents conflicting challenges for sleep evaluation. On one hand, subjects that review their sleep metrics may prefer to have quantitative analysis performed as quickly as possible so that data is available shortly after waking. On the other hand, initiating computationally expensive, server-side sleep analysis may be wasteful in those instances where the sleep disruption is transient in nature and the subject intends to return to sleep. In order to help minimize computational loads associated with discarded data, while still providing timely sleep analysis for subjects that intend to awake, the techniques described herein may be advantageously employed to predict a subject's sleep intention in order to arrive more quickly at an accurate assessment of whether a waking event reflects a transient sleep disruption or a subject's intention to awaken.

As described herein, a system may be configured to detect sleep intention for a subject in order to determine the likelihood that a given waking event is associated with an intention to remain awake. This analysis may apply empirical rules, and/or rules derived from historical data for a user or population such as the user's prior sleep patterns, other users' sleep patterns, or a combination thereof. In one aspect, sleep intention may be detected using a probabilistic analysis of historical data for a user, including information such as the time of day, the day of the week, seasonal factors, and so on. The detection of sleep intention may also be aided by a probabilistic analysis of data from a broader population, e.g., through look-alike models and whole-population analysis.

Figure 18:
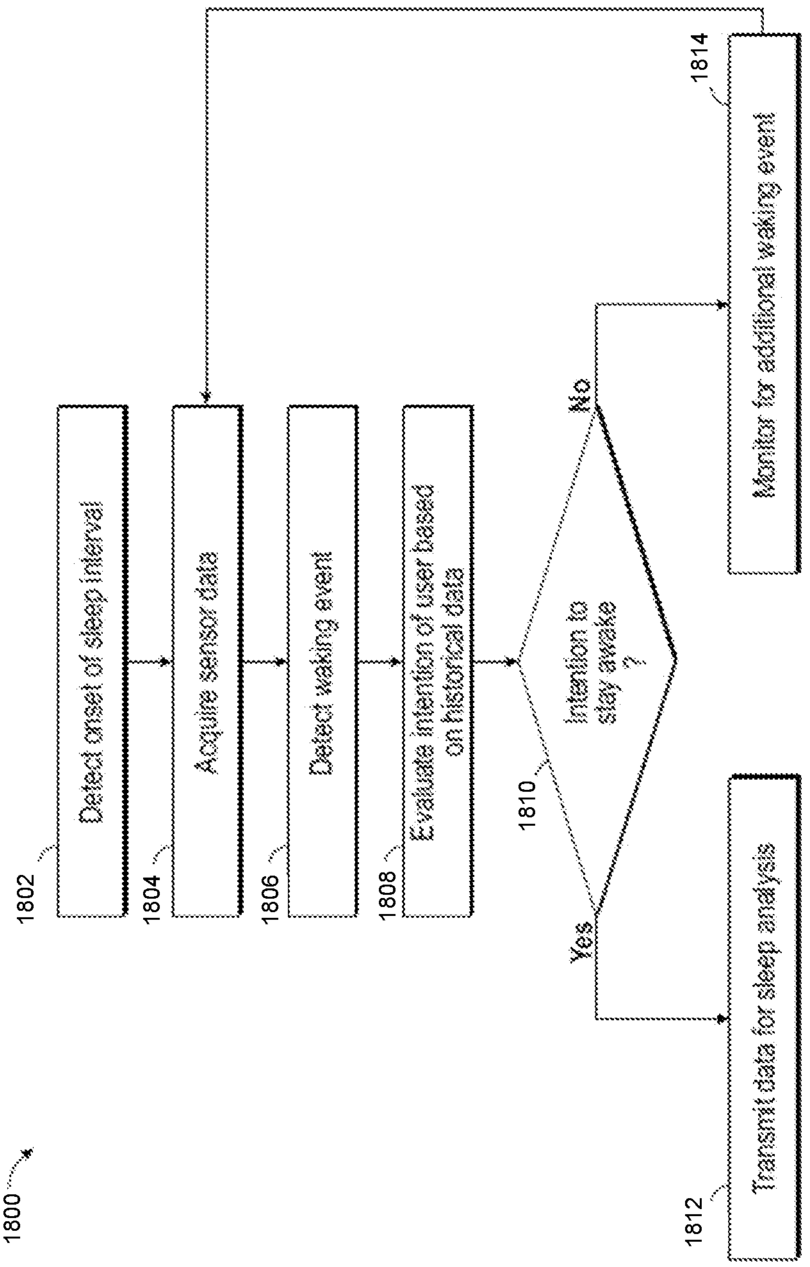
FIG. 18 is a flow chart illustrating a method for detecting sleep intention.

FIG. 18 is a flow chart illustrating a method for detecting sleep intention. The method 1800 may be used in any of the methods or systems described herein to improve sleep scoring. In general, the techniques described below seek to quickly and accurately differentiate between users that intend to arise and users that will return to sleep, more specifically in order to conserve processing resources that are used to evaluate sleep quality for those instances where a user is likely to remain awake and review sleep metrics. This may have particular advantage in systems where, e.g., sleep processing is computationally expensive, and/or where sleep processing is performed by remote processing resources.

As shown in step 1802, the method 1800 may include detecting an onset of a sleep interval. In general, a device such as any of the devices described herein may continuously, substantially continuously, or intermittently acquire data such as heart rate data, and analyze this data to detect the onset of a sleep interval. In this context, the sleep interval may include an interval over which a user desires an analysis (such as sleep quality or duration), or an interval otherwise suitable for evaluation and amenable to automatic detection. For example, the sleep interval may include an entire night's sleep, e.g., measured from when a user gets into bed and falls asleep until when the user rises from bed to begin the following day. The interval may also or instead include any substantial interval of inactivity or sleep detected for a user. In another aspect, the sleep interval may include other sleep sessions such as naps and the like. The sleep interval may include a sleep opportunity (the time dedicated to sleep) for a user, e.g., where the onset of the sleep interval begins when a user positions oneself for sleep (e.g., lays down in bed) before the user begins to fall asleep for the first time.

It will be understood that a sleep interval may include subsequent, intermittent events such as when the user briefly awakes and falls back asleep after waking. Thus, a sleep interval may include one or more sub-intervals, e.g., where a user falls back asleep after awakening, where a user is in different modes of sleep, and so on. To this end, the method 1800 may also or instead include detecting an onset and conclusion of such sub-intervals, particularly where such information is relevant to evaluating the quality or quantity of sleep, and/or where such information assists in accurately identifying the onset of a sleep interval to be analyzed, and/or for use in an analysis of historical data.

It will be understood that numerous sleep detection techniques are known in the art based on the physiology of sleep. Thus, for example, changes in body temperature, perspiration, movement, heart rate, respiratory rate, eye movement, blood pressure, blood oxygen levels, brain waves, and the like may all be used, either individually or in combination, to detect an onset of sleep, as well as transitions among various stages of sleep (e.g., light sleep, deep sleep, REM sleep, etc.), each of which has objectively measurable physical characteristics. Some or all of these physical characteristics may be detected by a wearable physiological monitoring device such as any of the devices described herein and used to detect an onset of sleep at the beginning of a sleep interval, as well as multiple subintervals within a sleep cycle and transitions among different stages of sleep.

As shown in step 1804, the method 1800 may include acquiring sensor data, e.g., with a physiological monitor worn by a user during a sleep interval. The physiological monitor may be a wearable physiological monitor such as any of the devices described herein, including without limitation a bracelet or other wearable strap that includes one or more sensors for acquiring physiological data. By way of example, the sensors may include light emitting diodes and light sensors (e.g., for acquiring photoplethysmography data), accelerometers (for acquiring motion data), thermocouples (for acquiring temperature data), microphones (for acquiring acoustic data), capacitive sensors or the like (for acquiring galvanic skin response data), and so forth. However, it should be understood that the techniques described herein are more generally applicable to any physiological monitoring system in which computing resources might advantageously be conserved by accurately identifying sleep intention, or more specifically, identifying when a user awakes and intends to stay awake after an interval of sleep.

As shown in step 1806, the method 1800 may include detecting a waking event with the physiological monitor. The waking event may be any event that objectively and measurably signals the user waking from the sleep interval. The waking event may include a single event such as a change in heart rate or a detection of motion, or the waking event may include a compound event based on numerous measurable events that collectively indicate arousal from a sleeping state.

Numerous techniques may be used, either alone or in combination, to detect a waking event. For example, detecting the waking event may include detecting physical movement inconsistent with sleep—e.g., sitting up or getting out of bed, raising an extremity above a predetermined height, movements of body parts above or below predetermined speed or acceleration thresholds, and so on. Detecting the waking event may also or instead include detecting heart rate activity inconsistent with sleep—e.g., a change in heart rate variability or a heart rate above or below a predetermined threshold that indicates a waking event, or any other change(s) in heart activity generally inconsistent with sleep. Detecting the waking event may also or instead include detecting a body temperature inconsistent with sleep—e.g., a body temperature above or below a predetermined threshold. Other techniques or criteria for detecting the waking event are also or instead possible as will be understood by a skilled artisan. For example, a machine learning system may be trained to recognize a waking event based on any available data from the device or the device context, including external data such as a time of sunrise or a day of the week, as well as locally sensed data such as increased light or sudden sounds in an area around the user.

However detected, the waking event may be associated with a user intention to return to sleep or a user intention to remain awake. For example, in one aspect a user may intend to awake, as evidenced by subsequent activity and a sustained, wakeful state. The waking event may instead include an event where the intention of the user is to return to sleep, as evidenced by a return to a motionless, prone position and subsequent sleep activity. These types of waking events may include, for example, general restlessness, a user response to an audio disturbance, and so on. Thus, it may be advantageous to determine the user's sleep intention prior to performing sleep analysis or other computationally expensive processing of acquired physiological data.

As shown in step 1808, the method 1800 may include, in response to the waking event, evaluating sleep intention, e.g., whether an intention of the user is to stay awake or return to sleep.

The evaluation of sleep intention may be based on historical sleep data. For example, historical sleep data may be obtained from a sleep history for the user, or otherwise customized for or adapted to a specific user. The historical sleep data may also or instead include data derived from other users, such as users of a platform or system for analyzing sleep, users having similar hardware or software for physiological monitoring, and so on. It will be understood that the historical sleep data may further be filtered, categorized, weighted, or selected to increase accuracy for the evaluation regarding the intention of the user to stay awake or return to sleep. For example, the historical sleep data for a population may be filtered to provide data for similarly situated users—this can be based on physiological, biological, or demographic data such as age, height, weight, physical condition, diet, medical history, and so forth.

The intention of the user may be evaluated using a probabilistic analysis of historical sleep data to calculate or otherwise estimate a probability of the intention of the user to stay awake or return to sleep according to one or more variables including categorical variables and quantitative variables. For example, useful categorical variables may include the day of the week, a season, and/or a geographical location. Useful quantitative variables may include the duration of the waking event, a duration of the preceding sleep interval, an amount of time away from a typical waking time, a duration of physical after waking movement, and/or an amount of physical movement. Certain variables such as the time of day may be used as a quantitative variable (e.g., when calculating temporal distance from a normal waking time) and/or a categorical variable (e.g., whether waking time is within an ordinary waking interval).

In one aspect, thresholds may be applied to quantitative variables in order to derive rules for evaluating sleep intention. For example, if the duration or amount of physical movement of the user after waking exceeds a predetermined threshold for movement (which threshold can be based on the user's historical data, other historical data, or a default threshold set by an administrator or the like), then a determination may be made that the user intends to stay awake. In another aspect, the fact of exceeding the threshold, or the amount in excess of the threshold, may be used as a basis for increasing the probability that the intention of the user is to stay awake.

The variables used in a probabilistic analysis of the historical sleep data to determine a probability of the intention of the user to stay awake or return to sleep may be weighted, where such weights may be default weights for certain variables or customized weights for a particular user or set of users. By way of example, for certain users with sporadic sleep patterns, one or more quantitative variables may be weighted more than one or more categorical variables. Specific variables, such as the duration of a preceding sleep interval and the amount or duration of movement after waking may provide good initial indicators of sleep intention, and may be used either exclusively or in a heavily weighted manner to evaluate sleep intention.

In one aspect, evaluating user sleep intention may include training a machine learning algorithm to estimate a likelihood of sleep intention outcomes based on one or more characteristics of the preceding sleep interval and/or the waking event, such as any of the variables or sensed conditions described herein. This machine learning algorithm may be applied to current data for a waking user to determine a probability distribution for sleep intention outcomes, or more generally to determine whether it is more likely that a user intends to arise or return to sleep. Other probabilistic models such as a stochastic model or the like may also or instead be used to evaluate the likelihood that a user intends to remain awake.

As shown in step 1810, the method 1800 may include determining a sleep intention for a user, or as illustrated, by determining whether the user sleep intention is to stay awake. This may include applying any of the analyses described above, or any other suitable probabilistic analyses, machine learning algorithms, rule-based evaluation, or other analyses, as well as combinations of the foregoing, to determine whether it is more likely that the user intends to stay awake or return to sleep. Evaluating sleep intention may advantageously be performed locally, e.g., on a wearable physiological monitor or the like, in order to conserve network communication resources (including bandwidth and power consumption) for those circumstances where the user is likely to request sleep metrics in the near future. A compact machine learning model or other algorithms may usefully be deployed on the wearable physiological monitoring device for this purpose.

As shown in step 1812, when it is determined that the intention of the user is to stay awake, the method 1800 may include transmitting data from a physiological monitor to a remote server for sleep analysis. It will be understood, however, that the sleep analysis, or a portion thereof, may also or instead be conducted locally, e.g., using a processor and memory of a local computing device or the physiological monitoring device that acquired the data. This may include any form of preprocessing, signal conditioning, compression, encryption, or other data processing that might usefully be performed in a local computing context before transmitting to a remote resource. The sleep analysis may include any of the sleep analysis described herein, or any other sleep analysis known in the art, and may usefully be presented to the user on a local device as one or more sleep metrics that evaluate the quality and/or duration of the entire sleep interval, and/or individual sleep stages or sleep cycles within the entire sleep interval.

As shown in step 1814, when it is determined that the intention of the user is to return to sleep, the method 1800 may include monitoring for an additional waking event upon which to evaluate the intention of the user, such as by returning to step 1804 and acquiring additional sensor data.

It will be understood that the method 1800 described above may be performed in whole or in part by a computer program product. For example, a computer program product comprising computer executable code embodied on a non-transitory computer readable medium that, when executing on a wearable physiological monitor, may perform the steps of: acquiring sensor data with the wearable physiological monitor worn by a user during a sleep interval, the sensor data including photoplethysmography data and accelerometer data; detecting a waking event with the wearable physiological monitor by analyzing the accelerometer data to locate physical movement inconsistent with sleep; in response to the waking event, evaluating whether an intention of the user is to stay awake or return to sleep using a probabilistic analysis based on historical sleep data to evaluate a probability that the intention of the user is to stay awake based on at least one of a duration of the sleep interval and a duration of the physical movement inconsistent with sleep; when it is more likely that the intention of the user is to stay awake, transmitting data from the wearable physiological monitor to a remote server for sleep analysis; and, when it is more likely that the intention of the user is to return to sleep, monitoring for an additional waking event upon which to evaluate the intention of the user.

It will be understood that one or more of the steps related to any of the methods described herein, or sub-steps, calculations, functions, and the like related thereto, can be performed locally, remotely, or some combination of these. Thus, the one or more of the steps of the method 1800 of FIG. 18 may be performed locally on a wearable device, remotely on a server or other remote resource, on an intermediate device such as a local computer used by the user to access the remote resource, or any combination of these. For example, using the example system 200 of FIG. 2, one or more steps of a technique for detecting sleep intention may, wholly or partially, be performed locally on one or more of the physiological monitor 206 and the user device 220, such as by training a machine learning model to distinguish intention to awake from intention to return to sleep, and then pruning or otherwise optimizing the machine learning model for deployment on the wearable device. Also, or instead, one or more steps of a technique for detecting sleep intention may, wholly or partially, be performed remotely on one or more of the remote server 230 and the other resource(s) 250. Thus, for example, wear a wearable monitor is positioned near a smartphone of the user during sleep, heart rate data may be continuously or periodically transmitted to the remote server 230, which may monitor received data to identify potential and actual intentions to awaken. Other combinations are also possible. For example, certain movement activity locally detected on a wearable device may be used to trigger the remote server 230 to evaluate sleep intention, and to request an update to heart rate data and the like if/when necessary. Any of these techniques may be used to advantageously permit the remote server 230 to defer computationally expensive sleep analyses until an intent to awaken is identified.

Phase-based coaching will now be described. This may include using physiological parameters measured over time from a wearable physiological monitoring device, such as respiratory rate, heart rate variability, temperature, and so forth from any of the wearable sensors and devices described herein, in order to identify a reproductive or physiological phase such as a pregnancy trimester, and then to provide adjustments to recommendations for activities such as sleep and exercise according to that identification.

It will be understood that any suitable physiological and/or hormonal phase may be detected and used to adjust activity recommendations as described herein. In some embodiments, reproductive phases such as menstrual cycle phases, a pregnancy trimester, postpartum periods, menopause, and perimenopause may be detected and/or measured to adjust recommendations for a user. Periodic variations in human physiology may also respond to seasonal changes, length of daylight, weekly behavioral patterns, and so forth. More generally, physiological rhythms may be generally categorized as ultradian (more than one day), circadian (about one day), and infradian (less than one day), and any such rhythms, patterns, cycles, or the like that can be measured or otherwise detected may be used to adjust recommendations for a user in a synchronized manner. Therefore, unless explicitly stated to the contrary or otherwise made clear by the context of this disclosure, when the disclosure uses a particular phase as an example, it will be understood that any suitable phase may also or instead be used in its place.

The physiological rhythms found in reproductive phases can cause significant physiological changes, and may impact sleep, strain, and/or recovery. At the same time, the rhythms may manifest themselves in measurable changes to heart rate variability (HRV), resting heart rate (RHR), respiration, the RR interval, temperature, and so forth, which lends itself to automatic detection and synchronized recommendations related to an individual's sleep, strain, and/or recovery. By way of example, an early follicular phase of the menstrual cycle may provide opportunities for increased strain during exercise relative to other phases of the menstrual cycle. Conversely, the later luteal phase of the menstrual cycle may adversely affect recovery and the overall effectiveness of exercise, and may thus be a phase where strain might be advantageously decreased relative to other phases of the menstrual cycle. Thus, by detecting the menstrual cycle, activity recommendations may automatically and responsively adjust to optimize a user's strain, recovery, and/or sleep so that a user can achieve improved health and fitness goals.

Against this backdrop, activity recommendations for a user can advantageously be tailored for a user based on identification of a reproductive phase. By way of example, if it is deduced that one can achieve the same next-day recovery level with less cardiovascular strain during the follicular phase of the menstrual cycle (relative to the luteal phase), a recommendation for strain can take this into account, e.g., by encouraging more strenuous training earlier in the menstrual cycle. More generally, a coaching algorithm for sleep, strain, and/or recovery can adjust recommendations according to any reproductive phase, such as by increasing or decreasing the recommended workout intensity based on a current phase.

In one aspect, the reproductive phase may be automatically detected based on correlations of phases to measurable physiological parameters, e.g., measured from a wearable physiological sensor that is substantially continuously worn by a user. However, phase information may also or instead be entered manually by a user, either as a technique for a coaching algorithm to acquire phase information, or as a way to verify automatically detected phases. In general, the reproductive phase may be automatically detected based on resting heart rate, heart rate variability, respiration rate, temperature, or some combination of these. It will also be understood that the phase may be used to adjust activity recommendations for different activity regimens such as rest, sleep, nutrition, exercise strain, and so forth.

Figure 19:
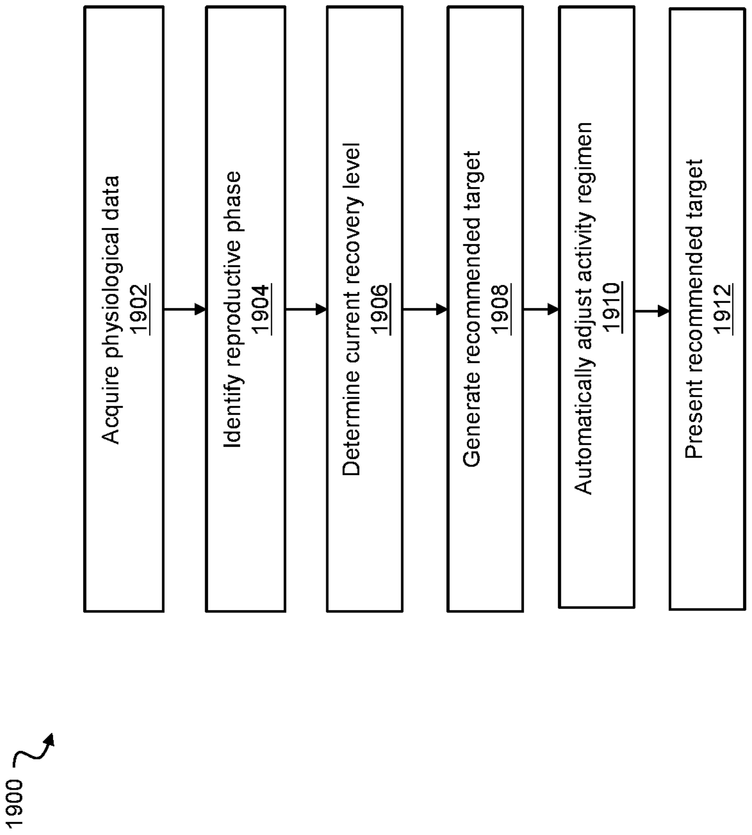
FIG. 19 is a flow chart illustrating a method for recommending adjustments to an activity regimen based on reproductive phases.

FIG. 19 is a flow chart illustrating a method 1900 for recommending adjustments to an activity regimen based on reproductive phases. While the disclosure focuses on reproductive phases, it is to be appreciated that the method 1900 may be applied to other suitable physiological and/or hormonal phases.

As shown in step 1902, the method 1900 may include acquiring physiological data for a user from a wearable physiological monitoring device. The user may be the wearer of the wearable physiological monitoring device, which may be any one or more of the devices described herein.

The physiological data may include heart rate data, such as heart rate variability (HRV), resting heart rate (RHR), RR intervals, peak-to-peak data, ECG data, and the like. The heart rate data may be obtained, at least in part, using photoplethysmography (PPG) from one or more sensors of the wearable device. The physiological data may also or instead include other physiological data such as data related to oxygen levels, skin temperature, body temperature, sweat levels, sweat content, and so on. Furthermore, data from the wearable device may be processed to infer other physiological data, for example by inferring respiration rate from heart rate variability. Moreover, the data may include other data such as summary data, motion data, fitness data, activity data, galvanic skin response data, or any other data described herein or otherwise contemplated by a skilled artisan. In general, source data may be acquired at the wearable device, preprocessed in any desired manner, and transmitted to a remote resource for processing using any of the techniques described herein.

The physiological data may be captured substantially continuously by the wearable physiological monitoring device and may be stored on the wearable device until a suitable connection to a remote processing unit is available. In this manner, acquiring the physiological data may include monitoring the user substantially continuously with a continuous physiological monitoring system and recording or calculating the physiological data as described herein. Continuous physiological monitoring is described above in significant detail, and the description is not repeated here except to note generally that this may include raw sensor data, processed data, or some combination of these that can be subsequently correlated to a reproductive cycle such as the menstrual cycle. Further, the method 1900 may include storing physiological data in any raw or processed form on the wearable physiological monitoring device, and/or transmitting the data to a local or remote location for storage, retrieval, and processing.

As shown in step 1904, the method 1900 may include identifying a reproductive phase for the user based on the physiological data. The reproductive phase may include one or more of a pregnancy trimester, a postpartum period (e.g., the first three months after childbirth), a phase of the menstrual cycle, a menopause phase, a perimenopause phase, and the like. However, it is to be appreciated that the reproductive phase may be any physiological phase based on reproductive hormones. In some embodiments, identifying the phase may include identifying the phase based on a pattern of change in a heart rate variability for the user over a period of time. For example, in exemplary data from over 3,000 wearers of physiological monitoring devices, on average heart rate variability (HRV) was about 8% higher than baseline in the early to mid-follicular phase of the menstrual cycle and about 4% lower than baseline in the mid to late-luteal phase of the menstrual cycle. Moreover, calculated recovery scores were about 10% higher during menstruation (i.e., during the early follicular phase) and dipped to slightly above 5% lower than baseline during the luteal phase. Moreover, when studying the relationship between strain and next-day recovery for females with natural cycles, it was shown that this effect holds even when there is a control for strain. This same effect was not seen for females using birth control with estrogen, however. Thus, from this experimental data, wearers with natural menstrual cycles tended to see their highest recovery scores in the first week of their cycles. Specifically, recovery scores in the early follicular phase were about 7 points higher (on average) than in the early luteal phase, when controlling for strain.

Also, or instead, identifying the reproductive phase for the user may be based on a resting heart rate, or a pattern of the resting heart rate, derived from user heart rate data. A number of techniques may be used to calculate the resting heart rate. For example, the resting heart rate may be calculated once per day, e.g., based on a measurement at a predetermined absolute time (e.g., 0100 hours) or relative time (e.g., shortly before waking). In another aspect, a summary statistic such as an average, median, or minimum may be calculated over some time period and used as the resting heart rate. This may be during sleep, or during one or more specific phases of sleep such as all slow wave sleep periods. This may instead be calculated (e.g., averaged) over the day during one or more periods when motion data or other data suggests that the wearer is at rest. Other techniques may also or instead be used.

In some embodiments, identifying the reproductive phase may include determining supplemental information about the reproductive phase, such as a duration of the phase, an onset date of the phase, and a probability that the identification is accurate. For example, in the case where the identified reproductive phase is a pregnancy trimester, the supplemental information may include a gestational age of a fetus.

The pattern of change in the resting heart rate over time may be used to determine the reproductive phase. This may include simple pattern recognition or extraction of periodic characteristics of the change (e.g., a frequency analysis or the like). In another aspect, the phase can be determined using machine learning or statistical methods. For example, a machine learning model may be trained to determine the reproductive phase based on one or more of a respiratory rate and a resting heart rate for the user. It will also be appreciated that phase determination may generally be fully automatic (e.g., using the techniques described herein), fully manual (e.g., based on explicit user reporting), or some combination of these. In a semi-automatic mode, a user may report specific events such as the beginning of menstruation, and other phase transitions may be automatically determined based on a model derived from, e.g., a user's prior manually entered phase history, population-level data, or some combination of these. Other user data such as body mass index and age may also or instead be relevant to phase prediction, and may be used to develop physiologically similar cohorts for training.

Similarly, the respiratory rate of the user, or a pattern of change in the respiratory heart rate, may be calculated using the heart rate variability of user heart rate data. For example, the heart rate generally increases during inhalation and decreases during exhalation. This general phenomenon may be algorithmically mapped to continuous heart rate variability data to determine when a user is inhaling and exhaling, and in turn to derive a respiratory rate. By calculating a daily respiratory rate (e.g., as an average of respiratory rates measured during the day, or as measured at a predetermined absolute or relative time), a pattern of change over time may be determined and used to determine the reproductive phase. In another aspect, the respiratory rate may be refined by first using peaks to identify respiratory patterns as described above, and then deriving a second estimate of respiratory rate using a frequency domain analysis to identify peaks in the power spectrum (for the underlying, time-based heart rate data) within a physiologically plausible range for respiratory rates. The first (time-based) estimate may be used to interpret the frequency domain estimate (which may otherwise exhibit multiple, plausible peaks) and to report the combined estimate (e.g., frequency domain estimate closest to the time domain estimate) as the current respiratory rate. A number of overlapping window functions may be used to average measurements over some time period (e.g., one or two minutes) in order to avoid potentially misleading point estimates of respiration.

While continuous heart rate data may be used to identify the reproductive phase, e.g., using the techniques described above, other techniques may also or instead be used. For example, in one aspect the reproductive phase may be identified based on user input such as an explicit demarcation of one or more reproductive phases. In another aspect, a physiological parameter such as skin temperature measured for the user—e.g., using the wearable physiological monitoring device, and mapped to a history of change in skin temperature over time—may be used to identify the reproductive phase.

In one aspect, identifying the reproductive phase may include training a machine learning model to detect the reproductive phase, e.g., based on a respiratory rate and/or a resting heart rate for the user, or any of the other data sources described herein, as well as combinations of the foregoing. That is, certain patterns may be known, or may become known, and a machine learning model may be trained to identify these patterns and thus to identify a reproductive phase.

As shown in step 1906, the method 1900 may include determining a current recovery level for the user based on a prior sleep activity for the user. A variety of techniques are described herein for calculating an objective recovery score for the current recovery level, e.g., based on the prior sleep activity and prior strain for the user. However, other techniques for estimating physical recovery may also or instead be used. The current recovery level may, for example, be based on estimates of strain using a heart rate variability, a resting heart rate, a respiratory rate, and the like.

The prior sleep activity may be based on the physiological data and/or other data using any of the techniques described herein, or any other technique based on, e.g., motion data, brain wave data, eye movement data, body temperature data, respiratory rate data, and so forth. Alternatively or in addition, the prior sleep activity may be based on user input such as a survey of the user's prior sleep activity. The prior sleep activity may include a duration of sleep for a prior sleep event, such as the previous night's sleep and/or intermittent sleep activity such as naps or the like.

As shown in step 1908, the method 1900 may include generating a recommended target for an activity regimen by the user, e.g., based on the current recovery level. In general, the recommended target may be based on data and/or metrics before taking into account the reproductive phase. In this manner, the recommended target may be determined in the same or similar manner to other activity regimen calculations described above. By way of example, the recommended target may be at least in part based on sleep quality (e.g., indicated by a sleep score as described herein), recent physiological strain (indicated by an intensity score as described herein), heart rate data, activity data, combinations thereof, and the like. The recommended target may provide an objective measure for the activity regimen, such as a calculated target number or amount for a user. The activity regimen may include any regimen that the user may engage in, such as sports (e.g., football, soccer, golf, tennis, etc.), exercise routines, recreational activities (e.g., biking, hiking, running, walking, meditation, etc.), sleep, rest, diet, hydration, and the like. Thus, for example, the recommended target may be a caloric target (e.g., 500 calories), a strain target (which will be understood to include a recommendation related to an activity volume and/or intensity, such as a training volume and/or intensity, e.g., using a calculated strain score on a scale between 0 and 21 or some other range), an output target (e.g., a distance, a number of stairs, a number of steps, etc.), a sleep target (e.g., duration of sleep, timing of sleep, and the like), or the like. The recommended target may also or instead include an activity target such as twenty minutes of running or thirty minutes of swimming. The recommended target may also or instead include more user-specific, compound recommendations such as running at least eight miles per hour for an interval of fifteen minutes, or swimming until 750 calories have been used. More generally, any recommendation suitable for coaching a user to engage in an activity regimen may be used for the recommended target as contemplated herein.

As shown in step 1910, the method 1900 may include automatically adjusting the activity regimen for the user by adjusting the recommended target based on the reproductive phase. For example, when the reproductive phase is a phase of the menstrual cycle, this step 1910 may include automatically adjusting the recommended target for the user by increasing a strain of the activity regimen during an early follicular phase of the menstrual cycle and decreasing the strain of the activity regimen during a late luteal phase of the menstrual cycle. In another aspect, in the case that the recommended target is a duration of sleep, adjusting the recommended target may include adjusting the duration. In another aspect, in the case that the reproductive phase is a pregnancy trimester, this step 1910 may include automatically adjusting the recommended target for the user by increasing a caloric target of a diet for the user during a second pregnancy trimester and a third pregnancy trimester.

As shown in step 1912, the method 1900 may include presenting the recommended target to the user on a user interface. The recommended target, or other adjusted recommendations or the like, may be communicated to the user on a user interface for any of a variety of mediums such as within a fitness application for a smart phone or other computing device associated with the wearable monitor, or within a fitness website accessible to the user that provides information and activity recommendations based on the user's data from the wearable device. In some embodiments, the user interface may present the reproductive phase to the user. Alternatively or in addition, the user interface may present supplemental information, such as alternative recommendations, health and fitness changes predicted to occur if the recommended target is taken, a confidence level of the identification of the reproductive level, a warning if the confidence level is below a predetermined threshold, a duration of the reproductive phase, and the like.

Figure 20A:
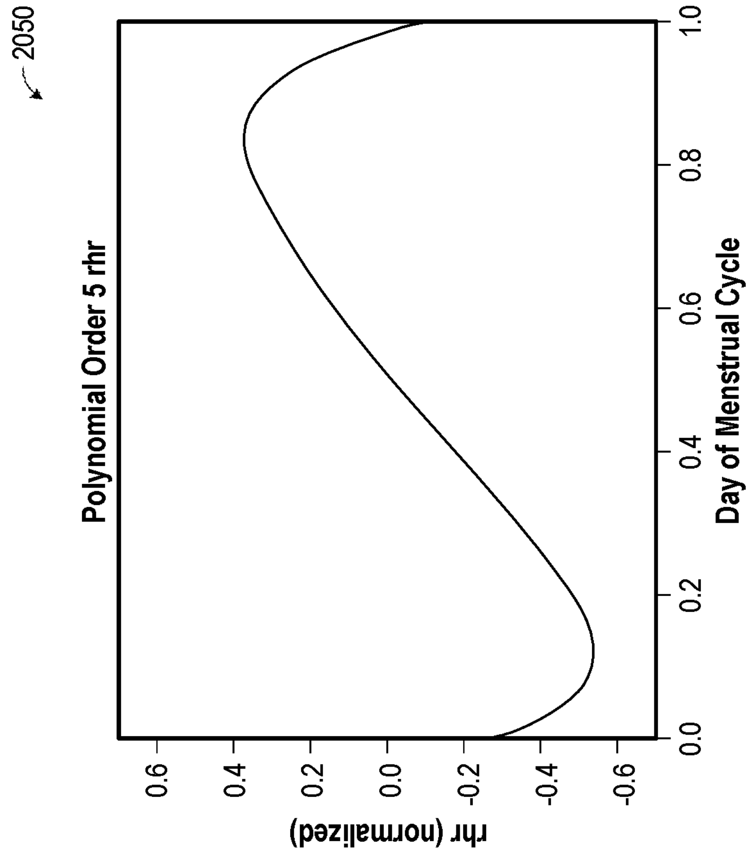
FIG. 20A illustrates a correlation useful for automatically detecting menstrual cycles.
Figure 20B:
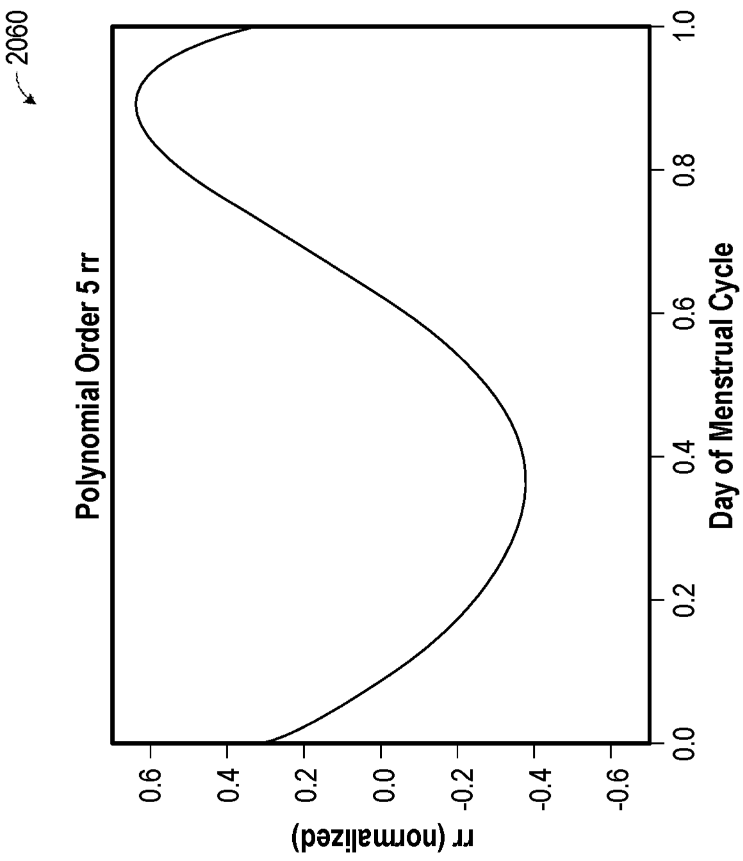
FIG. 20B illustrates a correlation useful for automatically detecting menstrual cycles.

FIGS. 20A-20B illustrates correlations useful for automatically detecting menstrual cycles. As describe above, phases in the menstrual cycle may be used for recommending adjustments to an activity regimen. While the menstrual cycle is used for exemplary purposes, it is to be appreciated that correlations can be detected for any suitable reproductive phase.

FIG. 20A illustrates a polynomial fit 2050 of actual resting heart rate data to days of the menstrual cycle. Resting heart rate can be correlated to the menstrual cycle and the resting heart rate has a pattern of variation over the course of menstrual cycle amenable to automatic detection of the cycle. Continuing with the experimental data gathered from wearers of physiological monitoring devices noted above, the resting heart rate (RHR) was nearly 5% lower during the mid-follicular phase and rose to about 3% higher in the luteal phase. This shift in RHR represents a substantial change of a nearly one standard deviation (when the data is normalized relative to individual baselines). Moreover, it was found that the respiratory rate was lowest during the mid-follicular phase and highest during the luteal phase.

FIG. 20B illustrates a polynomial fit 2060 of respiratory rate to days of the menstrual cycle for the same group of users. In general, the respiratory rate is lowest during the mid-follicular phase and highest during the luteal phase. Further, the change represents a shift of about one standard deviation and is suitable for use in automatically detecting phases within the menstrual cycle.

Several examples of recommending adjustments to activity regimens will now be described with reference to FIGS. 21-25. While these examples are related to specific reproductive phases, similar techniques may be employed for any other physiological phase that can be manually and/or automatically tracked, and based on which adjustments to activity regimens can be advantageously made over the course of the phase. Further, while the feedback in these examples generally pertains to adjustments for health and fitness (e.g., exercise, diet, sleep, recovery, and the like), other feedback may also or instead usefully be provided.

Figure 21:
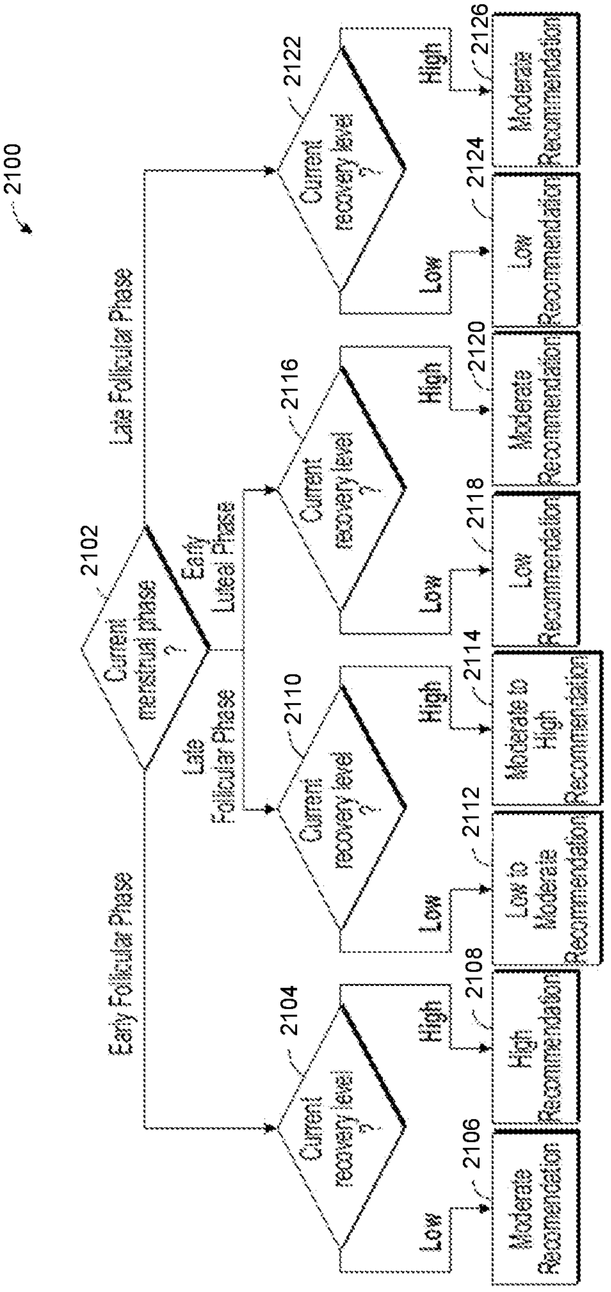
FIG. 21 is a flow chart illustrating a method for recommending an adjustment related to strain.

FIG. 21 is a flow chart illustrating a method for recommending an adjustment related to strain for an activity regimen based on a phase within a menstrual cycle. The user in this example may be the wearer of a wearable physiological monitoring device and user of a platform or system for physiological monitoring such as any of those described herein. The method 2100 may use any of the data and data sources described herein.

As shown in step 2102, the method 2100 may begin with determining a phase within a menstrual cycle for a user. The phase may be determined, e.g., using any of the techniques described herein. For example, the phase may be determined using heart rate data (e.g., HRV, RHR, RR, and so on), respiratory data (e.g., respiratory rate, one or more oxygen levels, and so on), temperature data, and so forth, and/or phase data may be received manually. For a menstrual cycle, the phase may be identified as one of the early follicular phase, the late follicular phase, the early luteal phase, or the late luteal phase. In the event that a phase cannot accurately be determined, the user may be notified and, where appropriate, queried for explicit phase identification. For each of the four phases identified in FIG. 21, activity recommendations concerning upcoming exercise may be tailored according to a current recovery level.

As shown in step 2104, the method 2100 may include determining the current recovery level when the phase is identified as the early follicular phase. In this case, when the current recovery level is 'low' and the user is in the early follicular phase of their menstrual cycle as shown in step 2106, the method 2100 may include providing a recommendation of a moderate level of strain for the user. Also, under these conditions, when the current recovery level is 'high' and the user is in the early follicular phase of their menstrual cycle, the method 2100 may include a recommendation of a high level of strain for the user, as shown in step 2108.

As shown in step 2110, the method 2100 may include determining the current recovery level when the phase is identified as the late follicular phase. In this case, as shown in step 2112, when the current recovery level is 'low' and the user is in the late follicular phase of their menstrual cycle, the method 2100 may include generating a recommendation of a low to moderate level of strain for the user. As shown in step 2114, when the current recovery level is 'high' and the user is in the late follicular phase of their menstrual cycle, the method 2100 may include a generating a recommendation of a moderate to high level of strain for the user.

As shown in step 2116, the method 2100 may include determining the current recovery level when the phase is identified as the early luteal phase. In this case, as shown in step 2118, when the current recovery level is 'low' and the user is in the early luteal phase of their menstrual cycle, the method 2100 may include generating a recommendation of a low level of strain for the user. As shown in step 2120, when the current recovery level is 'high' and the user is in the early luteal phase of their menstrual cycle, the method 2100 may include generating a recommendation of a moderate level of strain for the user.

As shown in step 2122, the method 2100 may include determining the current recovery level when the phase is identified as the late luteal phase. In this case, as shown in step 2124, when the current recovery level is 'low' and the user is in the late luteal phase of their menstrual cycle, the method 2100 may include generating a recommendation of a low level of strain for the user. As shown in step 2126, when the current recovery level is 'high' and the user is in the late luteal phase of their menstrual cycle, the method 2100 may include a recommendation of a moderate level of strain for the user.

Figure 22:
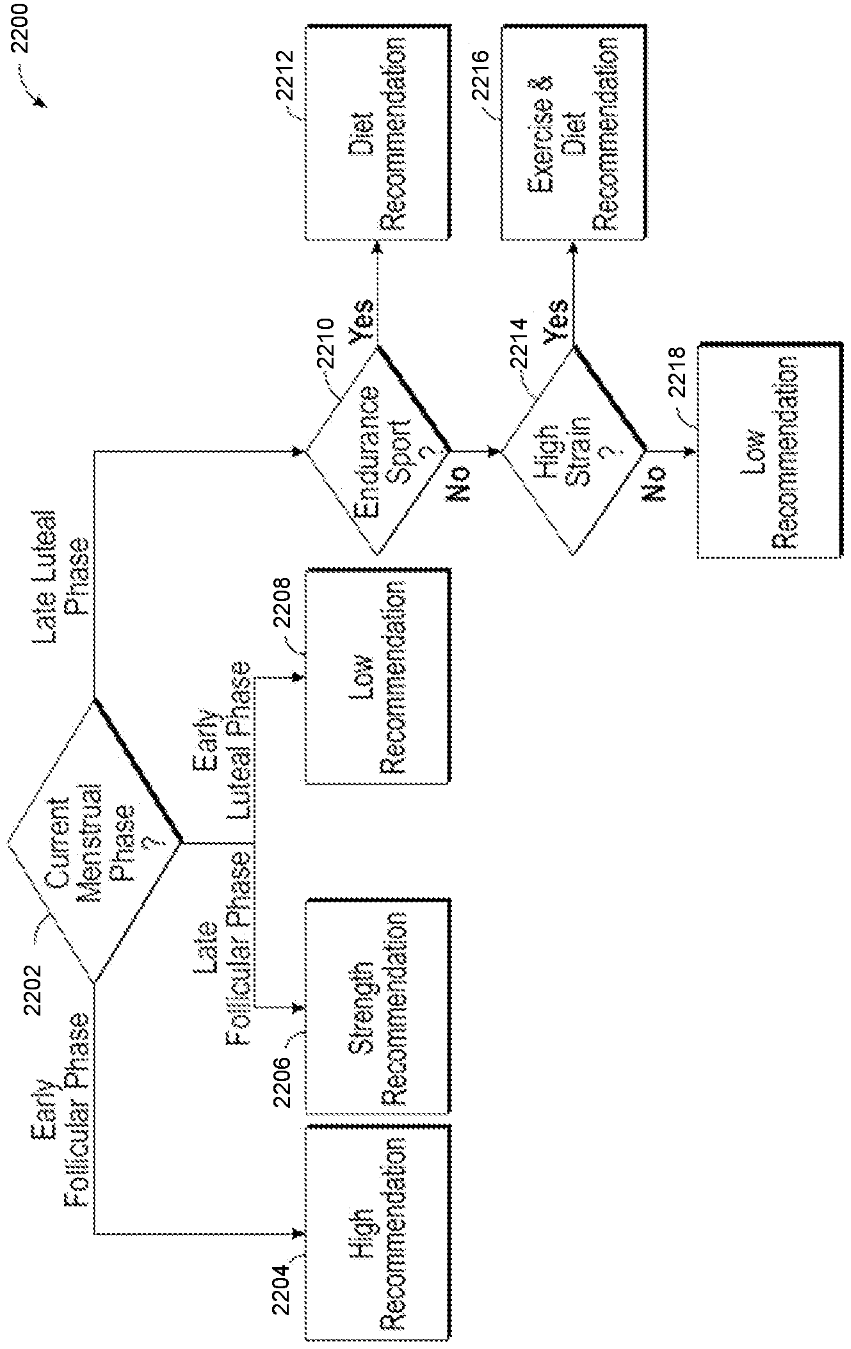
FIG. 22 is a flow chart illustrating a method for recommending an adjustment related to fitness and nutrition.

FIG. 22 is a flow chart illustrating a method for recommending an adjustment related to fitness and nutrition for an activity regimen based on a phase within a menstrual cycle. The user in this example may be the wearer of a wearable physiological monitoring device and user of a platform or system for physiological monitoring such as any of those described herein. The method 2200 may use any of the data and data sources described herein. In general, the type and intensity of exercise, as well as a user's diet may be coached with various cycle-specific recommendations to generally improve user outcomes.

As shown in step 2202, the method 2200 may begin with determining a phase within a menstrual cycle for a user. The phase may be determined, e.g., using any of the techniques described herein. For example, phase may be determined using heart rate data (e.g., HRV, RHR, RR, and so on), respiratory data (e.g., respiratory rate, one or more oxygen levels, and so on), temperature data, and so forth, or phase data may be received manually. For a menstrual cycle, the phase may be identified as one of the early follicular phase, the late follicular phase, the early luteal phase, or the late luteal phase. In the event that a phase cannot accurately be determined, the user may be notified and, where appropriate, queried for explicit phase identification.

As shown in step 2204, the method 2200 may include generating a recommendation for high intensity training when the phase is identified as the early follicular phase. This may, for example, include a general recommendation to engage in high-intensity activity, and/or this may include one or more explicit targets for intensity such as targets for heart rate, distance, rate of travel, weight usage, calories, duration, etc. This may also or instead include explicit exercise recommendations including, e.g., types and intervals of various activities.

As shown in step 2206, the method 2200 may include, when the phase is identified as the late follicular phase, generating a recommendation for strength-based training and/or longer warm-ups. This recommendation may be made as a measure to mitigate against injury for the user, because a user may be more susceptible to injury in the late follicular phase of the menstrual cycle.

As shown in step 2208, the method 2200 may include, when the phase is identified as the early luteal phase, generating a recommendation for low intensity training. As with other intensity-based recommendations, this may include a recommendation for a specific type, intensity, or duration of activity, or other objective metrics for intensity, as well as combinations of the foregoing. In another aspect, this may include a general recommendation to engage in low intensity activities, and/or an alert when intensity is exceeding recommended ranges.

As shown in step 2210, the method 2200 may include, when the phase is identified as the late luteal phase, determining whether the user has recently completed an endurance-based sport or training session. This determination may be based on data from sensors and/or from user input.

As shown in step 2212, the method 2200 may include, when the phase is identified as the late luteal phase and the user has recently completed an endurance-based sport or training session, providing a diet recommendation. For example, this may include recommending to the user to consume a relative high amount of carbohydrates as a way to replenish energy and speed recovery.

As shown in step 2214, the method 2200 may include, when the phase is identified as the late luteal phase and the user has not recently completed an endurance-based sport or training session, determining whether the user has recently completed a relatively high-strain workout. This determination may be based on data from sensors and/or from user input.

As shown in step 2216, the method 2200 may include, when the phase is identified as the late luteal phase and the user has recently completed a relatively high-strain workout, providing one or more of a diet and fitness recommendation. For example, this may include recommending to the user to hydrate before exercising, and/or to consume foods with a relatively high amount of sodium.

As shown in step 2218, the method 2200 may include, when the phase is identified as the late luteal phase and the user has not recently completed a relatively high-strain workout, recommending that the user engage in relatively low intensity training.

Figure 23:
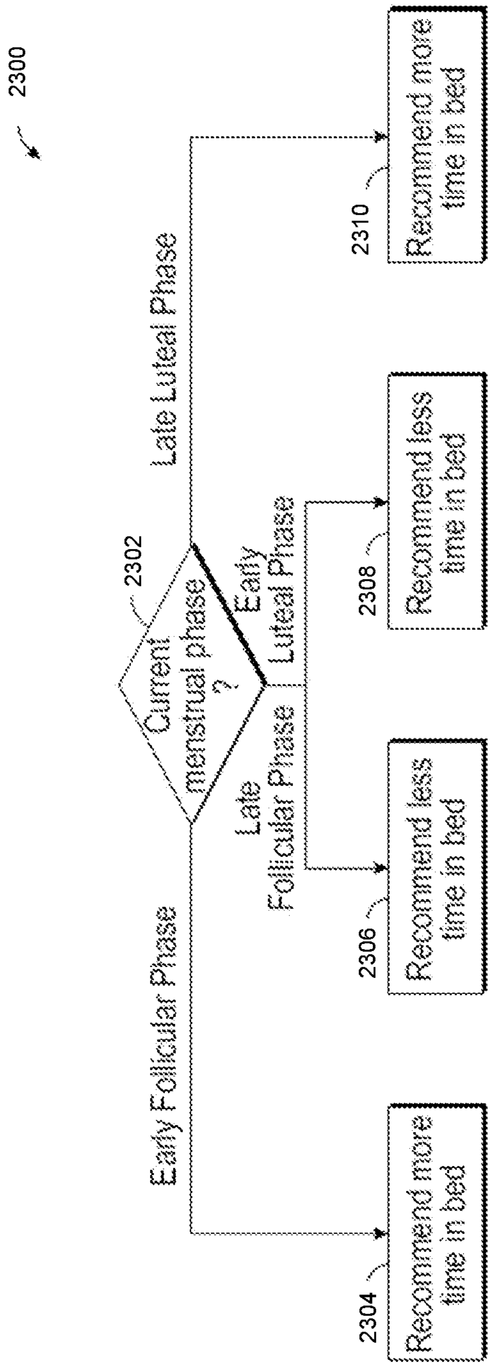
FIG. 23 is a flow chart illustrating a method for recommending an adjustment related to sleep based on a phase within a menstrual cycle.

FIG. 23 is a flow chart illustrating a method for recommending an adjustment related to sleep based on a phase within a menstrual cycle. The user in this example may be the wearer of a wearable physiological monitoring device and user of a platform or system for physiological monitoring such as any of those described herein. The method 2300 may use any of the data and data sources described above. In general, sleep recommendations for the user may be adjusted based on reproductive phases to generally improve user outcomes.

As shown in step 2302, the method 2300 may begin with determining a phase within a menstrual cycle for a user. The phase may be determined, e.g., using any of the techniques described herein. For example, phase may be determined using heart rate data (e.g., HRV, RHR, RR, and so on), respiratory data (e.g., respiratory rate, one or more oxygen levels, and so on), temperature data, and so forth, or phase data may be received manually. For a menstrual cycle, the phase may be identified as one of the early follicular phase, the late follicular phase, the early luteal phase, or the late luteal phase. In the event that a phase cannot accurately be determined, the user may be notified and, where appropriate, queried for explicit phase identification.

As shown in step 2304, the method 2300 may include generating a recommendation for more time in bed when the phase is identified as the early follicular phase. Generating the recommendation for more time in bed may include recommending a longer sleep session at night, more frequent naps during the day, an earlier bedtime, or the like. However, it is to be appreciated that any suitable recommendation related to sleep may be generated.

As shown in step 2306, the method 2300 may include generating a recommendation for less time in bed when the phase is identified as the late follicular phase. Generating the recommendation for less time in bed may include recommending a shorter sleep session at night, less frequent naps during the day, a later bedtime, or the like. However, it is to be appreciated that any suitable recommendation related to sleep may be generated.

As shown in step 2308, the method 2300 may include generating a recommendation for less time in bed when the phase is identified as the early luteal phase.

As shown in step 2310, the method 2300 may include generating a recommendation for more time in bed when the phase is identified as the late luteal phase.

While useful coaching recommendations and adjustments may be made according to a hormonal cycle such as the menstrual cycle, it will be understood that other human hormonal cycles may also or instead be used as the basis for adjusting recommendations for sleep (or other rest/recovery), exercise (or other activity), and/or nutrition. By way of example, reproductive phases such as pregnancy and menopause may result in substantial hormonal cycles and changes for individuals, with predictable physiological results that may be used as a basis for refining recommendations over the course of the hormonal cycle. A number of examples are provided below.

Figure 24:
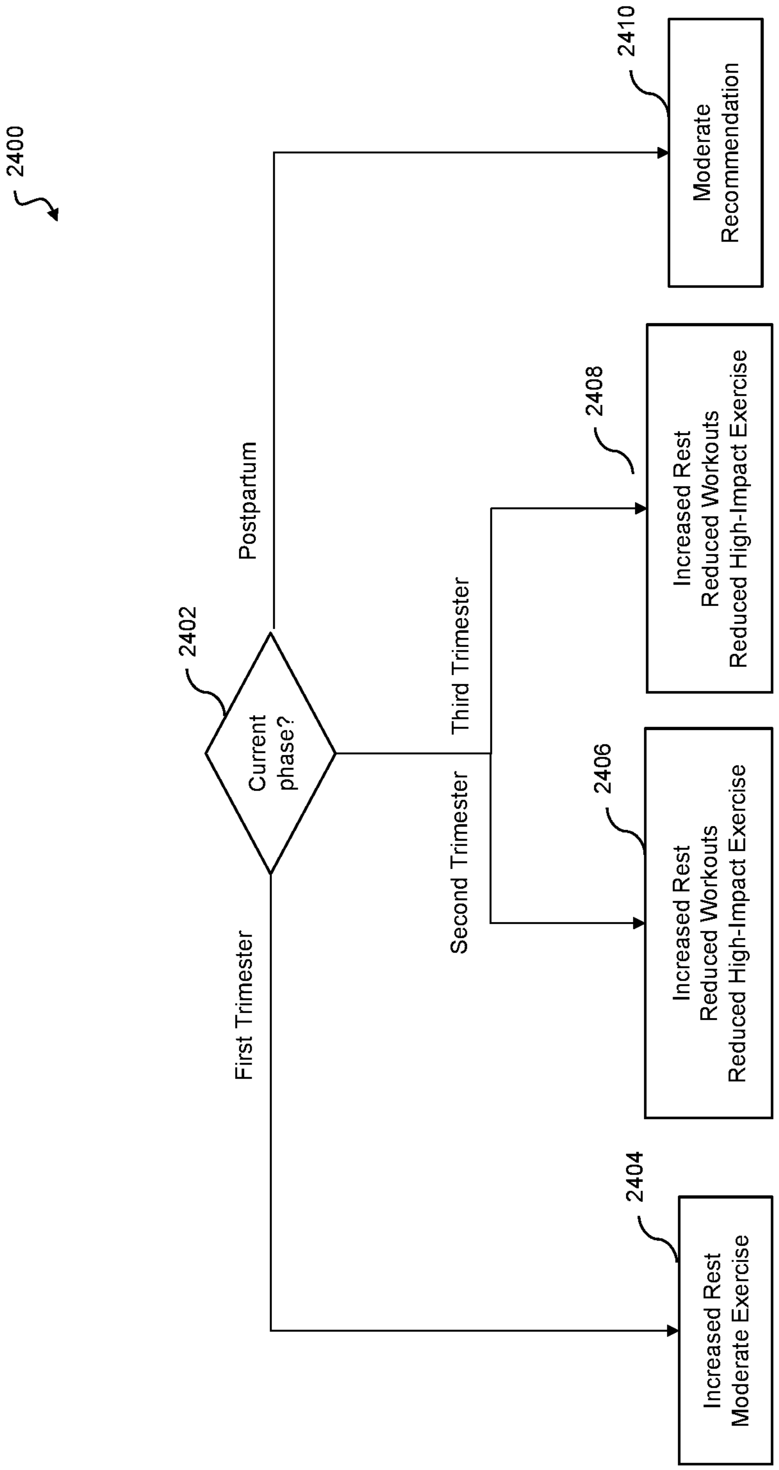
FIG. 24 is a flow chart illustrating a method for recommending an adjustment related to sleep based on a pregnancy trimester.

FIG. 24 is a flow chart illustrating a method for recommending an adjustment related to sleep based on a pregnancy trimester. The user in this example may be the wearer of a wearable physiological monitoring device and user of a platform or system for physiological monitoring such as any of those described herein. The method 2400 may use any of the data and data sources described above. In general, sleep recommendations for the user may be adjusted based on reproductive phases to generally improve user outcomes.

As shown in step 2402, the method 2400 may begin with determining a hormonal phase of a user such as a trimester of pregnancy. Pregnancy can be automatically detected by using continuous vital sign monitoring because it creates unique patterns in nightly heart rate, heart rate variability, skin temperature, and pulse oximetry, as well as in physiological metrics that can be derived from those inputs such as respiratory rate and sleep architecture. When these data are combined, pregnancy can be determined with high statistical confidence by week 5 to 6. Not only can the presence of a pregnancy be detected, but the approximate gestational age of the fetus can also be determined because the digital biomarkers used to identify pregnancy evolve as the pregnancy progresses. Thus, the trimester may be determined, e.g., using any of the techniques described herein. For example, phase may be determined using heart rate data (e.g., HRV, RHR, RR, and so on), respiratory data (e.g., respiratory rate, one or more oxygen levels, and so on), temperature data, and so forth; and/or phase data may be received manually. Alternatively or in addition, the phase may be determined from user reports (e.g., from a home pregnancy test). In some embodiments, determining the pregnancy trimester may include determining a gestational age of a fetus. In the event that a pregnancy trimester cannot accurately be determined, the user may be notified and, where appropriate, queried for explicit phase identification.

As shown in step 2404, the method 2400 may include generating a recommendation for a moderate time in bed when the phase is identified as the first trimester. This may also include coaching recommendations for, e.g., periodic moderate-intensity aerobic activity sufficient to elevate the heart rate, but not above about 140 beats per minute, such as brisk walking for 30 minutes at least five days per week.

As shown in step 2406, the method 2400 may include generating a recommendation for a moderate to high time in bed when the phase is identified as the second trimester. This may also or instead include reducing a recovery score, and/or reducing a recommended workout for a particular user recovery score. This may also or instead include recommendations, e.g., to reduce high-impact exercises that might carry an increased risk of injury due to relaxed ligaments.

As shown in step 2408, the method 2400 may include generating a recommendation for a moderate to high time in bed when the phase is identified as the third trimester. This may also or instead include reducing a recovery score, and/or reducing a recommended workout for a particular user with a particular recovery score. Similarly, strain scores may be adjusted upward to reflect aspects of increased strain due to pregnancy that might not be reflected in a strain calculation based on HRV. This may also or instead include recommendations to reduce high-impact or highly strenuous activities such as distance running.

As shown in step 2410, the method 2400 may include generating a recommendation for a moderate or increased time in bed when the phase is identified as the postpartum period (i.e., the "fourth" trimester). Recommendations may also or instead include reduced physical activity, and sleep scores may be adjusted to encourage greater rest and recovery. The postpartum period may be a period of three months after childbirth, although it is to be appreciated that any suitable length of time may be used instead.

Figure 25:
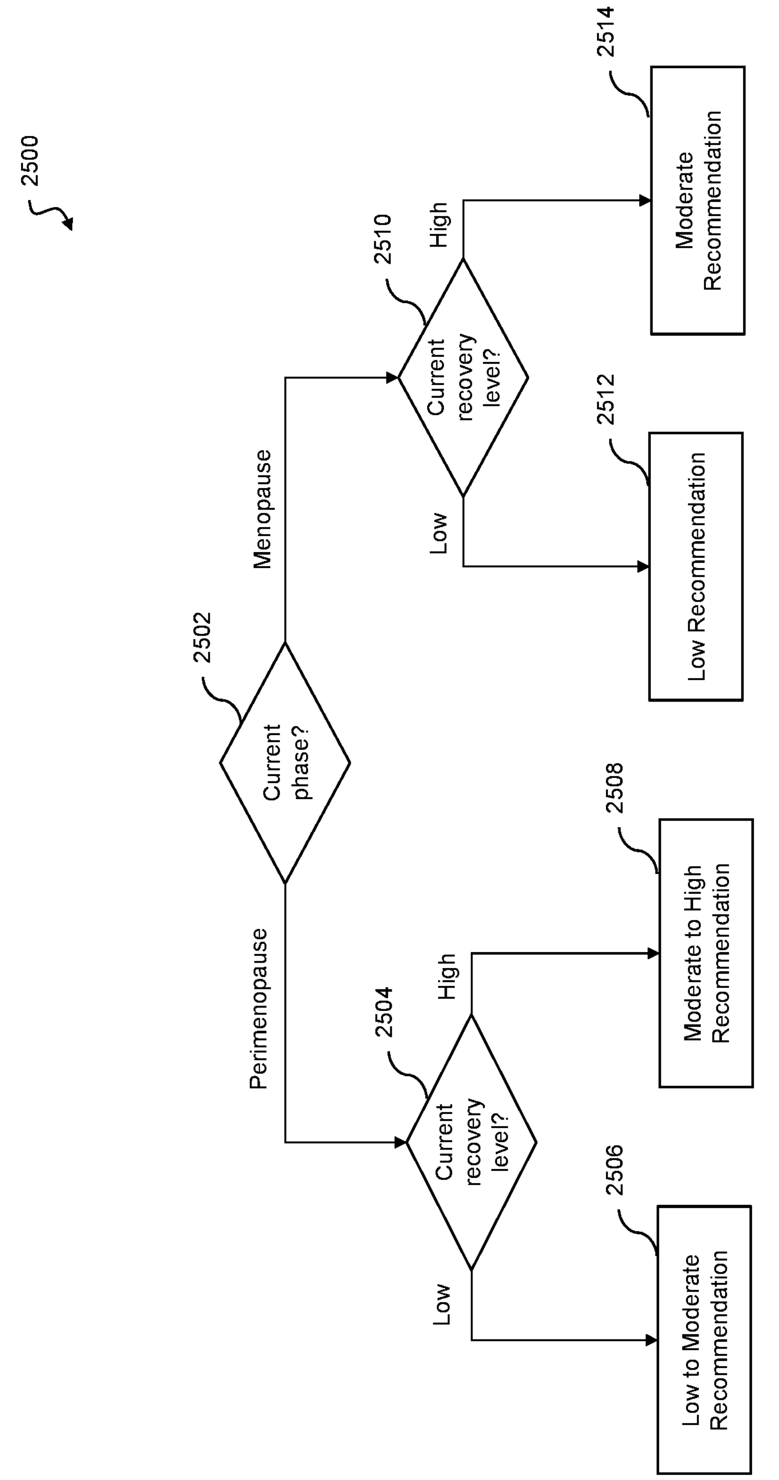
FIG. 25 is a flow chart illustrating a method for recommending an adjustment related to sleep based on a menopause phase or a perimenopause phase.

FIG. 25 is a flow chart illustrating a method for recommending an adjustment related to sleep based on a menopause phase or a perimenopause phase. The user in this example may be the wearer of a wearable physiological monitoring device and user of a platform or system for physiological monitoring such as any of those described herein. The method 2500 may use any of the data and data sources described herein.

As shown in step 2502, the method 2500 may begin with determining a hormonal phase for the user, such as a menopause phase or a perimenopause phase. The phase may be determined, e.g., using any of the techniques described herein. For example, the phase may be determined using heart rate data (e.g., HRV, RHR, RR, and so on), respiratory data (e.g., respiratory rate, one or more oxygen levels, and so on), temperature data, and so forth, or phase data may be received manually. Alternatively or in addition, the phase may be determined from user reports. In some embodiments, the menopause phase may be determined by determining an absence of a menstrual cycle or an absence of a regularity of the menstrual cycle. In some embodiments, the perimenopause phase may be determined by determining an increased irregularity of the menstrual cycle. In the event that a phase cannot accurately be determined, the user may be notified and, where appropriate, queried for explicit phase identification.

As shown in step 2504, the method 2500 may include determining the current recovery level when the phase is identified as the perimenopause phase. In this case, when the current recovery level is 'low' the method 2500 may include providing a recommendation of a low to moderate level of strain for the user, as shown in step 2506. Also, under these conditions, when the current recovery level is 'high' the method 2500 may include a recommendation of a moderate to high level of strain for the user, as shown in step 2508.

As shown in step 2510, the method 2500 may include determining the current recovery level when the phase is identified as the menopause phase. In this case, when the current recovery level is 'low' the method 2500 may include providing a recommendation of a low level of strain for the user, as shown in step 2512. Also, under these conditions, when the current recovery level is 'high' the method 2500 may include a recommendation of a moderate level of strain for the user, as shown in step 2514.

Figure 26:
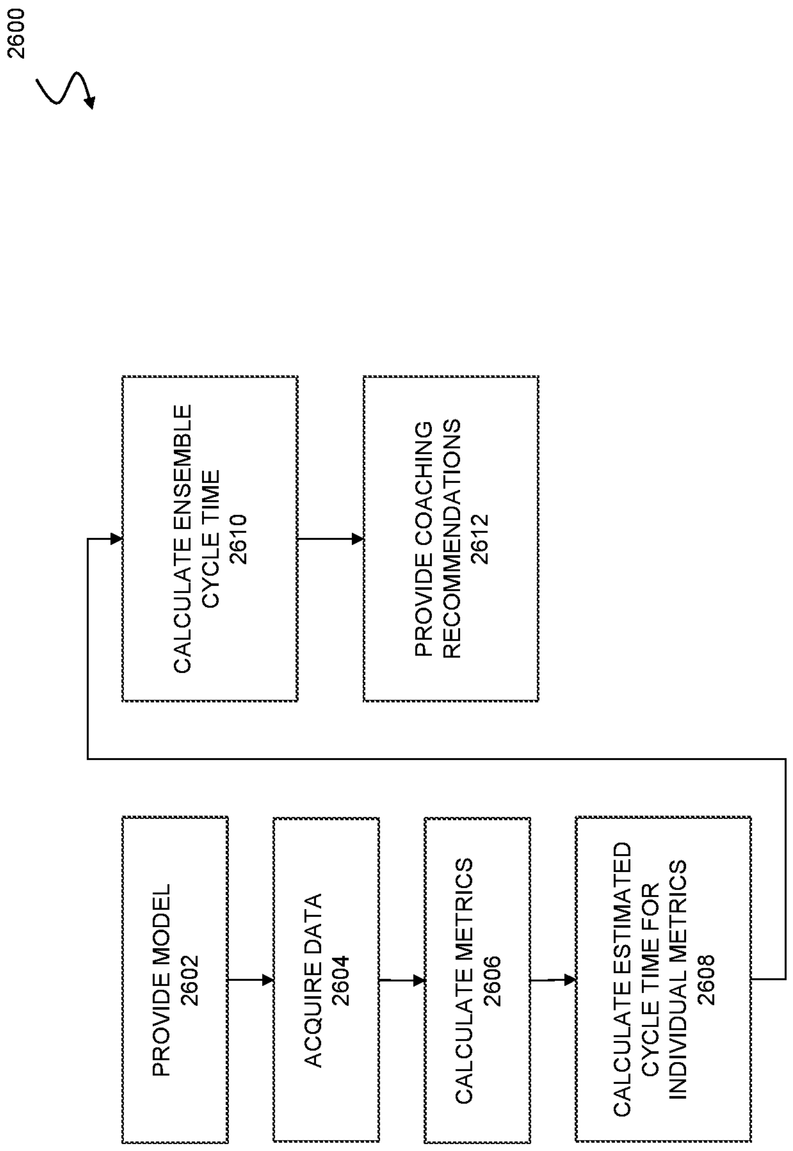
FIG. 26 is a flow chart of a method for providing coaching recommendations based on hormonal cycles.

FIG. 26 is a flow chart of a method for providing coaching recommendations based on hormonal cycles. In general, variations in hormone levels over the course of a hormonal cycle such as a menstrual cycle will result in measurable changes to various physiological metrics that can be measured with a wearable monitor. By tracking these observable metrics over time and comparing them to expected values for a cycle, a position of a user within the cycle can be determined. As a significant advantage, performing this monitoring automatically in the background can permit timely delivery of appropriate coaching recommendations to the user.

As shown in step 2602, the method 2600 may include providing a model for a hormonal cycle. In this context, providing a model may include storing the model where it can be applied in subsequent processing, or creating the model, e.g., by deriving a model hormonal cycle from a population of users, from a history of a particular user, or some combination of these. In general, the model may characterize timewise changes to each of a number of physiological metrics during a model hormonal cycle. For example, the physiological metrics may include a heart rate variability, a resting heart rate, a body temperature, a respiration rate, and so forth. The hormonal cycle may, for example, include a menstrual cycle for the user, a pregnancy of the user, or an onset of menopause for the user. While these are cycles of different frequency and duration, all such cycles are intended to fall within the meaning of a hormonal cycle as that phrase is used herein.

The model may include any suitable data structure for estimating cycle position based on the corresponding acquired physiological data. For example, this may include a timewise representation of changes in value, which can facilitate comparison of a measured pattern to the expected pattern to identify where a user is in the relevant hormonal cycle. In another aspect, data may be used to create a machine learning model, regression model, or other model that permits a calculation of a predicted time within a hormonal cycle based on a number of measurements of the underlying physiological metrics. For example, this may include a regression model or other predictive model for each of the physiological metrics of interest, which can be used to generate predicted values for comparison to measured values as a cycle progresses. In another aspect, an analytical model or an empirical model may be developed to generate a time-varying description that can be compared to current measurements, or against which a sequence of current measurements can be compared to determine a current time within the cycle. For example, a cycle may be modeled with a composite of sinusoidal functions, as a dynamic system with differential equations, with a machine learning model (such as a recurrent neural network, long short-term memory model, and so forth), or using any other model or the like that can suitably represent a cyclical, recurring pattern.

It will also be understood that, while generally described as similar, certain hormonal cycles may have different characteristics for which different types of modeling and analysis are appropriate. For example, where a cycle like pregnancy is a single-cycle phenomenon modeled as an end date prediction, the focus may be on estimating the duration until completion, and may involve a linear or time-series data set where the task is determining patterns or trends that will help to anticipate when an event will end. On the other hand, for a repeating cycle such as a menstrual cycle, the relevant inquiry is typically the current phase or position within a known repeating pattern. In this case, the expected duration may be of less interest than the current timing or phase. Thus, the analytical tools applied, and/or model used, may be different when addressing timing within a pregnancy term versus timing within a menstrual cycle. At the same time, where physiological metrics are providing timing information that relates to specific hormone levels, physiological states, and so forth, any related coaching strategies may advantageously benefit from the modeling techniques described herein.

In general, the physiological data may be sampled on some intermittent basis that provides consistency and reliability to the data for subsequent use in modeling and analysis. For example, data may be measured once per day, e.g., at a particular time of day, or at a particular time in a sleep cycle for the user. Data may also or instead be averaged over a number of measurements during a day or over a number of days. For example, in one aspect, multiple measurements may be taken during sleep, and the resulting stream of measurements may be weighted, e.g., based on recency, quality, sleep stage, and so forth to provide a single, derived measurement for the day. In another aspect, the metric may be created as a moving average over a number of days in order to smooth inter-day variations in the data. More generally, any repeatable technique that facilitates comparison of multiple measurements may be used to acquire data for the uses contemplated herein.

As shown in step 2604, the method 2600 may include acquiring data. This may include acquiring physiological data for a user from a wearable monitor such as any of the monitors described herein. The physiological data may include, e.g., heart rate data and body temperature data, and may be acquired during the course of a hormonal cycle for a user. In one aspect, heart rate data may be readily acquired, e.g., where the wearable monitor is a photoplethysmography device, and may be converted into other physiological metrics such as resting heart rate, heart rate variability, and respiration rate. In another aspect, the wearable monitor may include a temperature monitor, and the method 2600 may include acquiring temperature data from the temperature sensor and calculating a body and/or skin temperature (at least daily, or at the rate of acquisition of other physiological metrics) for the user.

As shown in step 2606, the method 2600 may include calculating a number of metrics for the user at some predetermined interval. For example, this may include acquiring data at least daily during the hormonal cycle. A number of factors unrelated to hormonal changes may cause timewise changes in one of the metrics. For example, an illness may cause an increase in body temperature, or one or more days of high physical strain may cause a temporary decrease in heart rate variability. By acquiring multiple metrics that have been separately modeled, such as two or more of physiological metrics described herein, an ensemble approach may advantageously be employed to improve the accuracy of detection and avoid undue influence of unrelated fluctuations in a single metric.

Calculating the number of metrics may, for example, include calculating a heart rate variability, a resting heart rate, a body temperature, and/or a respiration rate. In one aspect, these metrics may be acquired directly from the wearable monitor, in which case, little or no calculation may be required, except as desired for averaging, smoothing, filtering, and the like. In another aspect, the wearable monitor may provide a stream of raw pulse data, which may be converted by calculations into the metrics of interest. In either case, the method 2600 will generally include obtaining these physiological metrics for further processing as described herein.

As shown in step 2608, the method 2600 may include calculating an estimated cycle time for the user relative to the model hormonal cycle based on each of the number of (calculated) metrics independently. This may generally include applying each of the physiological metrics obtained above to the model in order to calculate the corresponding cycle time suggested by that physiological metric. The details of this calculation will depend on the nature of the model, and may include, e.g., applying data to a regression model, identifying matching timewise patterns (e.g., using any suitable time domain and/or frequency domain techniques), performing a lookup, or any other technique.

As shown in step 2610, the method 2600 may include calculating a cycle time within the hormonal cycle based on an ensemble of the estimated cycle times. A variety of ensemble techniques are known in the art, and may be used to process a group of estimated cycle times.

For example, in one aspect, the ensemble may include a weighted average of the estimated cycle time for each of the number of metrics such as physiological metrics or other metrics used to detect timing for hormonal cycles. The ensemble may also or instead include a combination of the estimated cycle time for each of the number of metrics based on a probability of accurately estimating the cycle time. In another aspect, the ensemble may include a Bayesian model average of the estimated cycle times, or an average of at least two of the estimated cycle times.

In another aspect, rules may be applied to the ensemble. For example, a predicted time may be withheld until two or more of the physiological metrics appear to agree on the timing within a predetermined threshold of probability (e.g., based on probability estimators or the like). In another aspect, a single outlier metric may be excluded when the remaining physiological metrics agree on a predicted timing. In this case, a user may be notified of the deviation from expected values, and/or related recommendations may be provided. More generally, a variety of techniques are known for processing data from multiple sources, such as machine learning models, regression models, and so forth. All such models are intended to fall within the scope of ensemble techniques as that phrase is used herein.

As shown in step 2612, the method 2600 may include providing coaching recommendations. In general, this may include any of the coaching recommendations described herein. As a significant advantage, the recommendations may be provided based on a reliable determination of the cycle time, and may be adapted to the particular user as the cycle timing accelerates or lags during particular cycles.

For example, elevated progesterone in the luteal phase may cause an increase metabolism and hunger. In this situation, additional dietary intake may be recommended. As another example, carbohydrates are preferentially used for energy during the follicular phase, while fat is more easily accessible for energy during the luteal phase. In view of this, where weight loss is a goal, a correspondingly lean diet may preferentially be used during the luteal phase. More generally, a diet may be recommended with more carbohydrates during the follicular phase and more fats during the luteal phase in order to match macronutrient intake to metabolic tendencies. As another example, because carbohydrates can be more difficult to access for energy during the luteal phase and fatigue can occur more quickly, lower intensity workouts may be recommended. Conversely, the enhanced ability to access carbohydrates for energy, along with decreased sensitivity to pain, during the follicular phase can make this a good time for intense workouts, and heavy strength training or the like may be preferentially recommended at these times. As another example, progesterone produced during the late luteal phase may increase catabolism, so additional protein may be recommended in the late luteal phase.

More generally, any of the coaching strategies or recommendations described herein may be deployed in a manner synchronized to hormonal cycle timing that has been calculated based on measured or calculated physiological metrics.

According to the foregoing, in one aspect, there is disclosed herein a wearable monitor, a model, and a processor configured to generate recommendations for the user. The wearable monitor may be configured to acquire heart rate data from a user. The model may be stored in a memory, and may characterize timewise changes during a model hormonal cycle for each of two or more physiological metrics. The processor may be configured to generate a recommendation for the user by performing the steps of: receiving the heart rate data from the wearable monitor; calculating the two or more physiological metrics for the user on a periodic basis based on the heart rate data; calculating a cycle time within a hormonal cycle for the user based on an ensemble of estimated cycle times, each of the estimated cycle times derived by applying one of the physiological metrics to the model; and providing coaching information to the user based on the cycle time. In one aspect, the processor may execute on a personal computing device of the user. In another aspect, the processor may execute on a remote server coupled to the wearable monitor through a data network. In another aspect, the processor may include multiple processors distributed across these and/or other resources to perform these steps.

Figure 27:
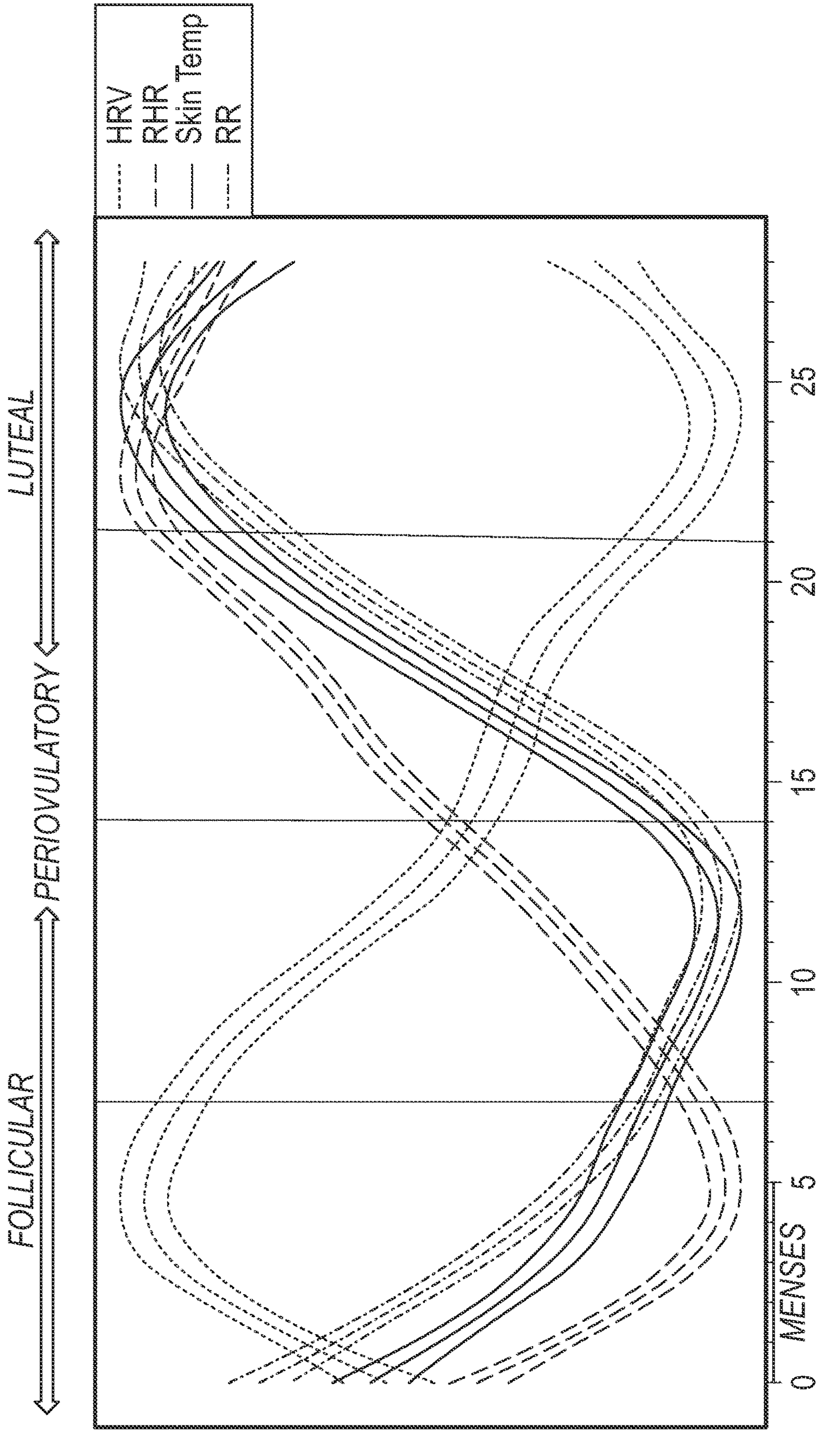
FIG. 27 shows a model for a menstrual cycle.

FIG. 27 shows a model for a menstrual cycle. In general, the model 2700 may include timewise data for a number of physiological metrics, such as heart rate variability, resting heart rate, skin temperature, and/or respiration rate, based on historical data for a user or a population of users, e.g., using the techniques described herein to establish consistency among measurements. As shown in FIG. 27, each of the physiological metrics has a characteristic shape of a mean, as well as a characteristic variability, which may be a percentile range, standard deviation, or other metric for variability, over the course of a twenty eight day menstrual cycle. This model may be used to predict timing, e.g., by acquiring data and performing an ensemble analysis to evaluate which point during the cycle a particular data set indicates.

Figure 28:
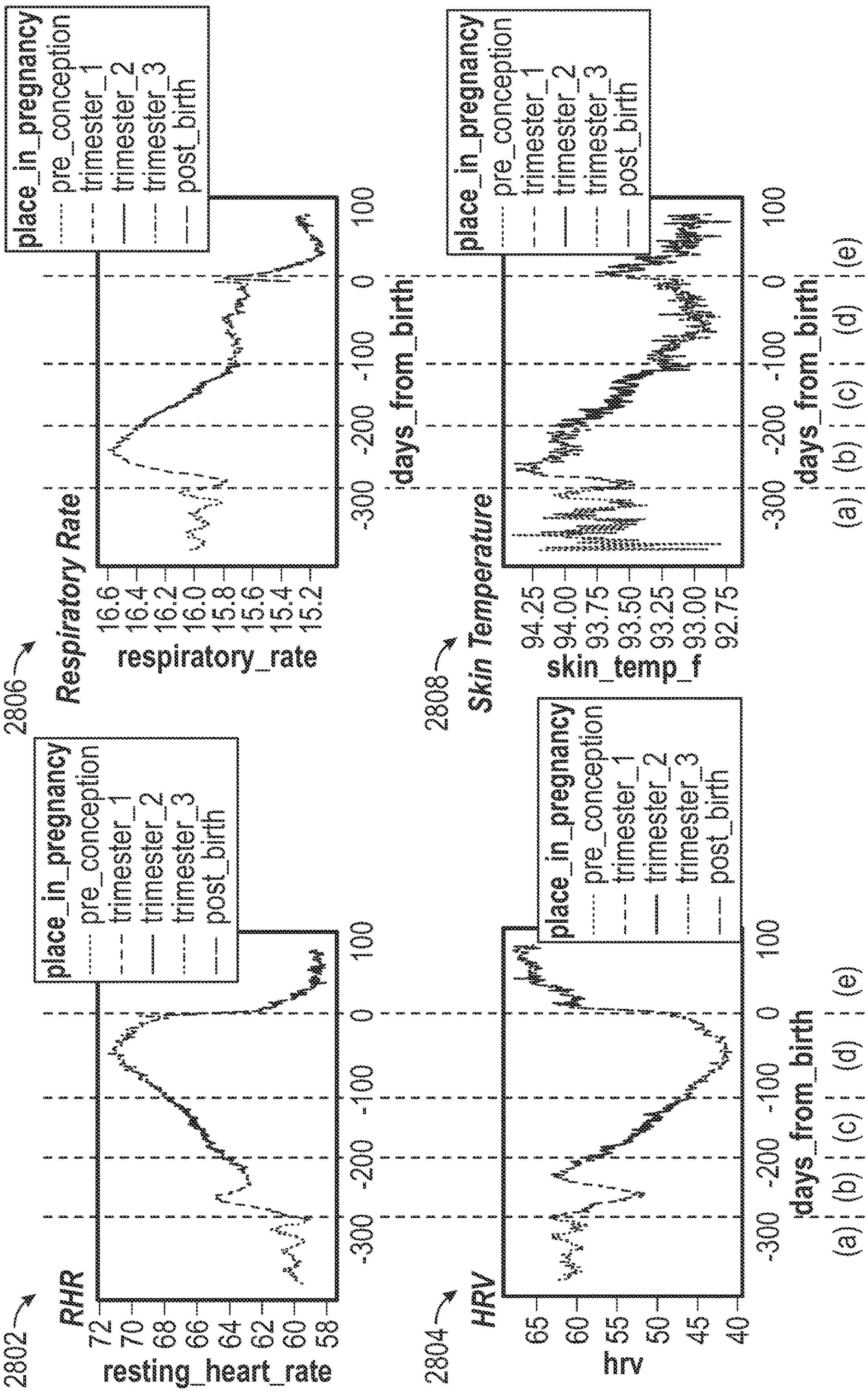
FIG. 28 shows a model for a pregnancy cycle.

FIG. 28 shows a model for a pregnancy cycle. In general, the model may include a separate timewise model for each physiological metric, such as a resting heart rate model 2802, a heart rate variability model 2804, a respiratory rate model 2806, and a skin temperature model 2808, each modeling the expected timewise change in the corresponding metric based on a time during a pregnancy. The model may, for example, be based on a population of users, a history of a particular user, or some combination of these. In general, a pregnancy may be divided into several discrete stages, such as (a) pre-pregnancy, (b) first trimester, (c) second trimester, (d) third trimester, and (e) post birth. While the techniques described herein may usefully be employed to identify which of these discrete stages a user is in, a multi-metric ensemble may advantageously permit more accurate timing estimations, e.g., by identifying the day or week within the pregnancy. This can advantageously facilitate coaching recommendations that are better synchronized to the state of pregnancy, and/or the specific hormonal levels for the user. This also permits the identification of contrary trends for one or more metrics, which may be flagged for a user along with recommendations for additional actions.

Figure 29:
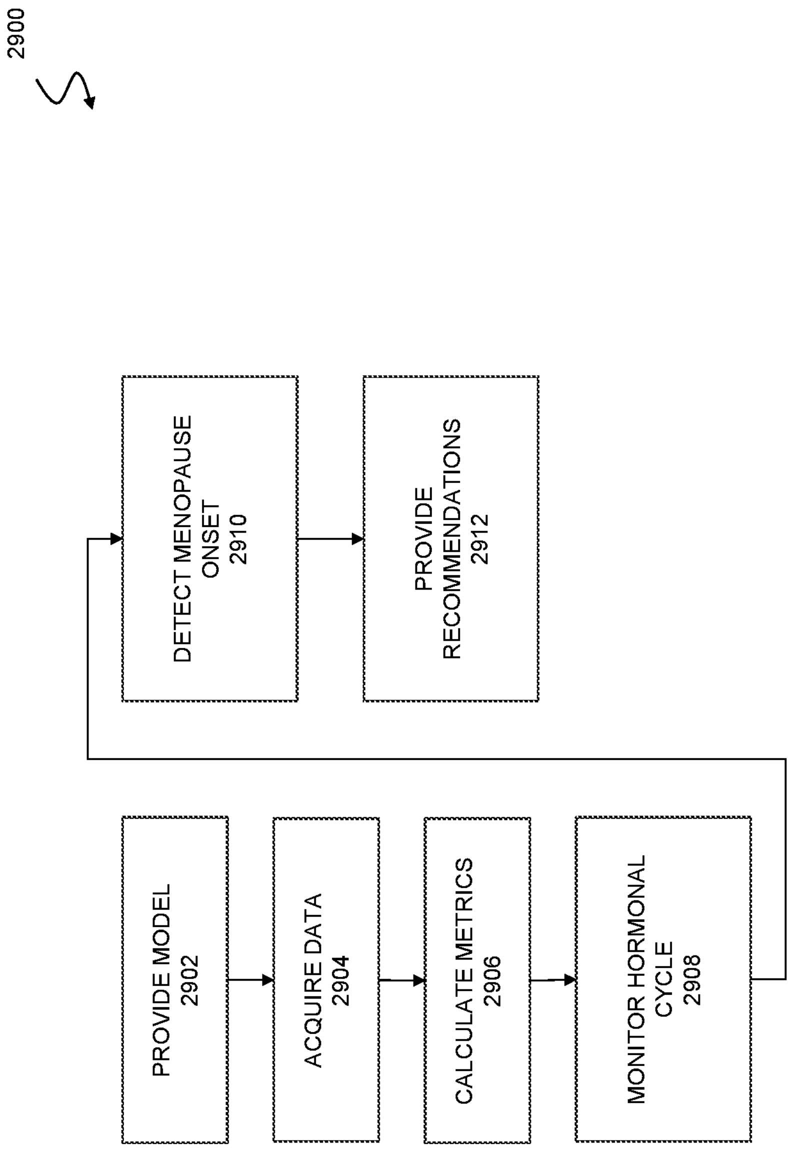
FIG. 29 is a flow chart of a method for detecting an onset of menopause.

FIG. 29 shows a method for detecting an onset of menopause. In general, the method 2900 may include providing a model as shown in step 2902, acquiring data as shown in step 2904, calculating metrics as shown in step 2906, and monitoring a hormonal cycle as shown in step 2908, all as described, for example, with reference to the method 2600 of FIG. 26.

As shown in step 2910, the method 2900 may include detecting an onset of menopause. A variety of techniques may be employed to detect an onset of menopause in this context. In general, the onset of menopause is accompanied by changes in the hormone levels associated with the menstrual cycle, leading to corresponding changes (typically decreases) in the variation of physiological metrics associated with the levels of hormones. At the same time, these changes may result in increased variations in the frequency and duration of menstrual activity. This variability may be used to detect the onset of menopause, and to better coordinate any related coaching recommendations with the accompanying physiological changes.

In one aspect, detecting the onset of menopause may be based on timewise irregularities in the observed hormonal cycle. Thus, detecting the onset of menopause may include identifying one or more timewise irregularities in the hormonal cycle relative to the model hormonal cycle, calculating a likelihood that the one or more timewise irregularities indicate an onset of menopause, and in response to calculating a likelihood above a predetermined threshold of an onset of menopause based on the one or more timewise irregularities, providing a predicted onset of menopause for the user. In one aspect, identifying the one or more timewise irregularities includes detecting a deviation in at least one of the physiological metrics from the model. In another aspect, identifying the timewise irregularities includes detecting a deviation in an ensemble of the two or more physiological metrics from the model. In another aspect, identifying the one or more timewise irregularities includes detecting a change in an expected duration of the hormonal cycle.

In another aspect, detecting the onset of menopause may be based on a decrease in variations of the physiological metrics that are related to the hormone levels for a user. In this case, detecting the onset of menopause may include identifying a series of peaks in the hormonal cycle for each of the two or more physiological metrics, identifying a timewise decrease in magnitude of each of the two or more physiological metrics for the series of peaks, and in response to the timewise decrease in magnitude, providing a predicted onset of menopause for the user.

As shown in step 2912, the method 2900 may include providing recommendations such as any of the coaching or other recommendations described herein. By way of non-limiting examples, providing recommendations may include providing a recommendation to the user based on the predicted onset of menopause, the recommendation including at least one of a diet recommendation, a sleep recommendation, and an activity recommendation (e.g., an exercise recommendation, or a recommendation related to activities other than exercise). In one aspect, these recommendations may be coordinated with a timing of the user within the onset of menopause, e.g., to provide appropriate support and health guidance. In one aspect, providing recommendations may include notifying the user of the predicted onset of menopause, e.g., so that the user can consider appropriate actions.

According to the foregoing, there is disclosed herein a system including a wearable monitor configured to acquire heart rate data from a user, and a processor configured to perform the steps of: receiving the heart rate data from the wearable monitor; calculating two or more physiological metrics for the user on a periodic basis based on the heart rate data, the two or more physiological metrics having a value influenced by one or more hormones associated with a hormonal cycle of the user; generating a predicted onset of menopause for the user based on a predetermined pattern in the two or more physiological metrics over time; and providing coaching information to the user based on the predicted onset of menopause.

In one aspect, the hormonal cycle may be identified by applying the two or more physiological metrics to a hormonal cycle model, and the predetermined pattern may include one or more timewise irregularities in the hormonal cycle. In another aspect, the hormonal cycle may be identified by applying the two or more physiological metrics to a hormonal cycle model, and the predetermined pattern may include a timewise decrease in magnitude of each of the two or more physiological metrics for a series of peaks in the hormonal cycle. In another aspect, both predetermined patterns may advantageously be used together to more accurately assess the onset and timing of menopause.

The above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above, and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same. In another aspect, means for performing the steps associated with the processes described above may include any of the hardware and/or software described above. All such permutations and combinations are intended to fall within the scope of the present disclosure.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y, and Z may include any method of directing or controlling any combination of such other individuals or resources to perform steps X, Y, and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. A computer program product comprising computer executable code embodied in a non-transitory computer readable medium that, when executing on one or more computing devices, performs the steps of:

providing a model that characterizes timewise changes during a model hormonal cycle for each of a heart rate variability, a resting heart rate, a body temperature, and a respiration rate;

acquiring physiological data for a user from a wearable monitor, wherein the physiological data includes at least heart rate data and body temperature data, and wherein the physiological data is acquired during a hormonal cycle for the user;

calculating a number of metrics for the user at least daily during the hormonal cycle, the number of metrics including at least the heart rate variability, the resting heart rate, the body temperature, and the respiration rate;

calculating an ensemble of estimated cycle times for the user relative to the model hormonal cycle, wherein each estimated cycle time in the ensemble of estimated cycle times is a separate estimate of cycle time based on one of the number of metrics independently;

calculating a probability of accurately estimating a metric-dependent cycle time for each separate estimate of cycle time for one of the number of metrics;

calculating a cycle time within the hormonal cycle for the user based on a combination of each separate estimate of cycle time in the ensemble of the estimated cycle times and the probability of each separate estimate of cycle time in the ensemble of cycle times accurately estimating the metric-dependent cycle time for one of the number of metrics; and providing coaching information to the user based on the cycle time.

2. The computer program product of claim 1, wherein the hormonal cycle includes a menstrual cycle for the user.

3. The computer program product of claim 1, wherein the hormonal cycle includes a pregnancy of the user.

4. The computer program product of claim 1, wherein the ensemble includes a weighted average of the estimated cycle time for each of the number of metrics.

5. The computer program product of claim 1, wherein the two or more physiological metrics include at least one of a heart rate variability, a resting heart rate, and a respiration rate.

6. A method comprising:

providing a model that characterizes timewise changes during a model hormonal cycle for each of two or more physiological metrics;

acquiring heart rate data from a wearable monitor worn by a user;

calculating the two or more physiological metrics for the user at least daily based on the heart rate data;

calculating an ensemble of estimated cycle times for the user relative to the model hormonal cycle, wherein each estimated cycle time in the ensemble of estimated cycle times is a separate estimate of cycle time based on one of the two or more physiological metrics independently;

calculating a probability of accurately estimating a metric-dependent cycle time for each separate estimate of cycle time for one of the two or more physiological metrics;

calculating a cycle time within a hormonal cycle for the user based on a combination of each separate estimate of cycle times in the ensemble of estimated cycle times and the probability of accurately estimating the metric-dependent cycle time for the each separate estimate of cycle time for one of the two or more physiological metrics, each estimated cycle time in the ensemble derived by applying one of the two or more physiological metrics to the model; and providing coaching information to the user based on the cycle time.

7. The method of claim 6, wherein the hormonal cycle includes a menstrual cycle for the user.

8. The method of claim 6, wherein the hormonal cycle includes a pregnancy of the user.

9. The method of claim 6, wherein the ensemble includes a weighted average of an estimated cycle time for each of the physiological metrics.

10. The method of claim 6, wherein the ensemble includes a combination of the estimated cycle times based on a probability of accurately estimating the cycle time.

11. The method of claim 6, wherein the ensemble includes a Bayesian model average of the estimated cycle times.

12. The method of claim 6, wherein the ensemble includes an average of at least two of the estimated cycle times.

13. The method of claim 6, wherein the wearable monitor includes a photoplethysmography monitor.

14. The method of claim 13, wherein the two or more physiological metrics include at least one of a heart rate variability, a resting heart rate, and a respiration rate.

15. The method of claim 6, wherein:

the two or more physiological metrics include a body temperature, the wearable monitor includes a temperature sensor, and the method includes acquiring temperature data from the temperature sensor and calculating the body temperature at least daily for the user.

16. The method of claim 6, wherein the model hormonal cycle is derived from a population of users.

17. The method of claim 6, wherein the model hormonal cycle is derived from a history of the user.

18. A system comprising:

a wearable monitor configured to acquire heart rate data from a user;

a model stored in a memory, the model characterizing timewise changes during a model hormonal cycle for each of two or more physiological metrics; and a processor configured to generate a recommendation for the user by performing the steps of:

receiving the heart rate data from the wearable monitor;

calculating the two or more physiological metrics for the user on a periodic basis based on the heart rate data;

calculating an ensemble of estimated cycle times for the user relative to the model hormonal cycle, wherein each estimated cycle time in the ensemble of estimated cycle times is a separate estimate of cycle time based on one of the two or more metrics independently;

calculating a probability of accurately estimating a metric-dependent cycle time for each separate estimate of cycle time based on one of the two or more physiological metrics;

calculating a cycle time within a hormonal cycle for the user based on a combination of each separate estimate of cycle time in the ensemble of estimated cycle times and the probability of each separate estimate of cycle time in the ensemble of cycle times accurately estimating the metric-dependent cycle time for each of the two or more physiological metrics, each of the estimated cycle times derived by applying one of the two or more physiological metrics to the model; and providing coaching information to the user based on the cycle time.

19. The system of claim 18, wherein the processor executes on a personal computing device of the user.

20. The system of claim 18, wherein the processor executes on a remote server coupled to the wearable monitor through a data network.

* * * * *